United States Patent
Li et al.

(10) Patent No.: US 12,005,270 B2
(45) Date of Patent: Jun. 11, 2024

(54) SYSTEMS AND METHODS FOR ACCELERATED ONLINE ADAPTIVE RADIATION THERAPY

(71) Applicant: The Medical College of Wisconsin, Inc., Milwaukee, WI (US)

(72) Inventors: X. Allen Li, Milwaukee, WI (US); Ying Zhang, Milwaukee, WI (US); Sara Lim, Milwaukee, WI (US); Jingqiao Zhang, Milwaukee, WI (US); Ergun Ahunbay, Milwaukee, WI (US); Ranjeeta Thapa, Milwaukee, WI (US); Haidy Nasief, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 623 days.

(21) Appl. No.: 17/256,339

(22) PCT Filed: Jun. 26, 2019

(86) PCT No.: PCT/US2019/039159
§ 371 (c)(1),
(2) Date: Dec. 28, 2020

(87) PCT Pub. No.: WO2020/006032
PCT Pub. Date: Jan. 2, 2020

(65) Prior Publication Data
US 2021/0220670 A1    Jul. 22, 2021

Related U.S. Application Data

(60) Provisional application No. 62/690,289, filed on Jun. 26, 2018.

(51) Int. Cl.
*A61N 5/10* (2006.01)
*G06N 20/00* (2019.01)
(Continued)

(52) U.S. Cl.
CPC ......... *A61N 5/1031* (2013.01); *A61N 5/1038* (2013.01); *G06N 20/00* (2019.01);
(Continued)

(58) Field of Classification Search
CPC .... A61B 6/032; A61B 6/5217; A61N 5/1031; A61N 5/1038; G06N 20/00;
(Continued)

(56) References Cited

U.S. PATENT DOCUMENTS

2011/0118588 A1* 5/2011 Komblau .............. A61N 5/1049
600/411
2011/0257545 A1* 10/2011 Suri ...................... A61B 8/5223
600/508

(Continued)

OTHER PUBLICATIONS

Julia Schwaab, "Computer-aided image quality assessment in automated 3D breast ultrasound images," Jan. 22, 2016, Dissertation submitted to the Faculty of Physics University of Bremen, Germany for the degree of Doctor of Natural Sciences , pp. 19-23,33-49.*

(Continued)

*Primary Examiner* — Omar S Ismail
(74) *Attorney, Agent, or Firm* — Quarles & Brady LLP

(57) ABSTRACT

Systems and methods for accelerated online adaptive radiation therapy ("ART") are described. The improvements to online ART are generally provided based on the use of textural analysis and machine learning algorithms implemented with a hardware processor and a memory. The described systems and methods enable more efficient and accurate online adaptive replanning ("OLAR"), which can also be implemented in clinically acceptable timeframes. For example, OLAR can be reduced from taking 10-30 minutes down to 5-10 minutes.

27 Claims, 26 Drawing Sheets

(51) Int. Cl.
  *G06T 5/40* (2006.01)
  *G06T 7/11* (2017.01)
  *G06T 7/149* (2017.01)
  *G06T 7/174* (2017.01)
  *G16H 20/40* (2018.01)
  *G16H 30/40* (2018.01)

(52) U.S. Cl.
  CPC .................. *G06T 5/40* (2013.01); *G06T 7/11* (2017.01); *G06T 7/149* (2017.01); *G06T 7/174* (2017.01); *G16H 20/40* (2018.01); *G16H 30/40* (2018.01); *G06T 2207/10081* (2013.01); *G06T 2207/10088* (2013.01); *G06T 2207/20081* (2013.01); *G06T 2207/30008* (2013.01); *G06T 2207/30096* (2013.01)

(58) Field of Classification Search
  CPC . G06T 2207/10081; G06T 2207/10088; G06T 2207/20081; G06T 2207/30008; G06T 2207/30096; G06T 5/40; G06T 7/11; G06T 7/12; G06T 7/149; G06T 7/174; G06T 7/33; G16H 10/60; G16H 20/40; G16H 30/40; G16H 50/20
  See application file for complete search history.

(56) References Cited

U.S. PATENT DOCUMENTS

| | | | |
|---|---|---|---|
| 2013/0294671 A1 | 11/2013 | Iida et al. | |
| 2015/0055849 A1* | 2/2015 | Galavis | G06T 7/0012 382/132 |
| 2015/0297916 A1* | 10/2015 | Chen | G06T 7/13 600/1 |
| 2016/0213278 A1* | 7/2016 | Urish | A61B 5/055 |
| 2017/0193662 A1 | 7/2017 | Zhou et al. | |
| 2018/0099152 A1 | 4/2018 | Nioutsikou | |
| 2018/0188392 A1* | 7/2018 | Polf | A61N 5/1049 |
| 2019/0094390 A1* | 3/2019 | Polf | A61N 5/1071 |
| 2019/0192880 A1* | 6/2019 | Hibbard | A61N 5/1039 |
| 2020/0107756 A1* | 4/2020 | El Naqa | G01T 1/2008 |
| 2020/0214119 A1* | 7/2020 | He | H05H 9/044 |
| 2020/0268330 A1* | 8/2020 | Altunbas | A61B 6/4035 |

OTHER PUBLICATIONS

Dipl.-Ing. Martin Buschmann, "Image guided adaptive radiation therapy for pelvic malignancies: from conceptual developments towards clinical implementation," Feb. 2018, Doctoral thesis at the Medical University of Vienna for obtaining the academic degree, pp. 26-45.*

T. Lustberg et al., Radiotherapy and Oncology, 126 (2018), 312-317.

D. Nguyen et al., Dose Prediction with U-net: A Feasibility Study for Predicting Dose Distributions from Contours using Deep Learning on Prostate IMRT Patients, May 23, 2018, https://arxiv.org/vc/arxiv/papers/1709/1709.09233v3.pdf? [retrieved on Oct. 2, 2019].

Li, A. Allen et al., Radiotherapy and Oncology 100 (2011) 370-374.

Ates, O. et al., Medical Physics, vol. 43, No. 6, Jun. 2016, 2756-2764.

Ahunbay, E. et at., Medical Physics, vol. 43, No. 8, Aug. 2016, 4575-4584.

* cited by examiner

Ground Truth
Auto-generated Contour

Ground Truth
Before Correction
After Correction
Contour Evolution

Adaptive Plan

Repositioning Plan

SYSTEMS AND METHODS FOR ACCELERATED ONLINE ADAPTIVE RADIATION THERAPY

CROSS-REFERENCE TO RELATED APPLICATIONS

This application is a 371 U.S. National Phase application of PCT/US2019/039159, filed Jun. 26, 2019, which claims the benefit of U.S. Provisional Patent Application Ser. No. 62/690,289, filed on Jun. 26, 2018, and entitled "SYSTEMS AND METHODS FOR ACCELERATED ONLINE ADAPTIVE RADIATION THERAPY," which is herein incorporated by reference in its entirety.

BACKGROUND

The anatomy, biology, or both, of a tumor or an organ-at-risk ("OAR") can be substantially and randomly changed during radiation therapy ("RT") delivery. Online adaptive radiation therapy ("ART") is a state-of-the-art approach that generally includes imaging patient-specific anatomy and/or biology the day before each RT delivery (i.e., fraction), creating a new RT plan adaptive to the changes of anatomy/biology of the tumor and OARs, and delivering the new adaptive RT plan to the patient. These steps should be completed within a practical time frame because the patient is lying on the table and waiting to be treated during the online adaptive replanning.

The lengthy, and perhaps clinically impractical, time required to segment anatomy in images acquired on the day of treatment and to evaluate the plan are bottle-necks for practicing online ART. It would therefore be desirable to provide faster and more robust methods for segmenting anatomy and evaluating the RT plan within an online ART framework. It would also be desirable to provide a robust technique to quickly identify the need of online ART.

SUMMARY OF THE DISCLOSURE

The present disclosure addresses the aforementioned drawbacks by providing methods for improved online adaptive radiation treatment ("ART") and online adaptive replanning ("OLAR").

In one aspect of the present disclosure, a method for controlling a radiation treatment planning system to identify whether it would be advantageous to perform OLAR, and to optionally initiate an OLAR procedure, is provided.

In another aspect of the present disclosure, a method for correcting radiation treatment plan contours and thereby generate corrected radiation treatment plan contour data is provided.

In still another aspect of the present disclosure, a method for validating an accuracy of radiation treatment plan contour data is provided.

In yet another aspect of the present disclosure, a method for assessing a quality of a radiation treatment plan is provided.

In another aspect of the present disclosure, a method for producing a synthetic computed tomography (CT) image from a magnetic resonance image is provided.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIGS. 10A and 10B show transverse and coronal views, respectively, of the daily CT images. FIGS. 10C and 10D show different feature values for various shell volume inward and outward the original duodenum (FIG. 10C) and pancreas head (FIG. 10D) contours. The X-axis in FIGS. 10C and 10D is the interval of the contour expansion (positive) or contraction (negative). All feature values are normalized to the one from the original organ volume.

DETAILED DESCRIPTION

Figure 1:
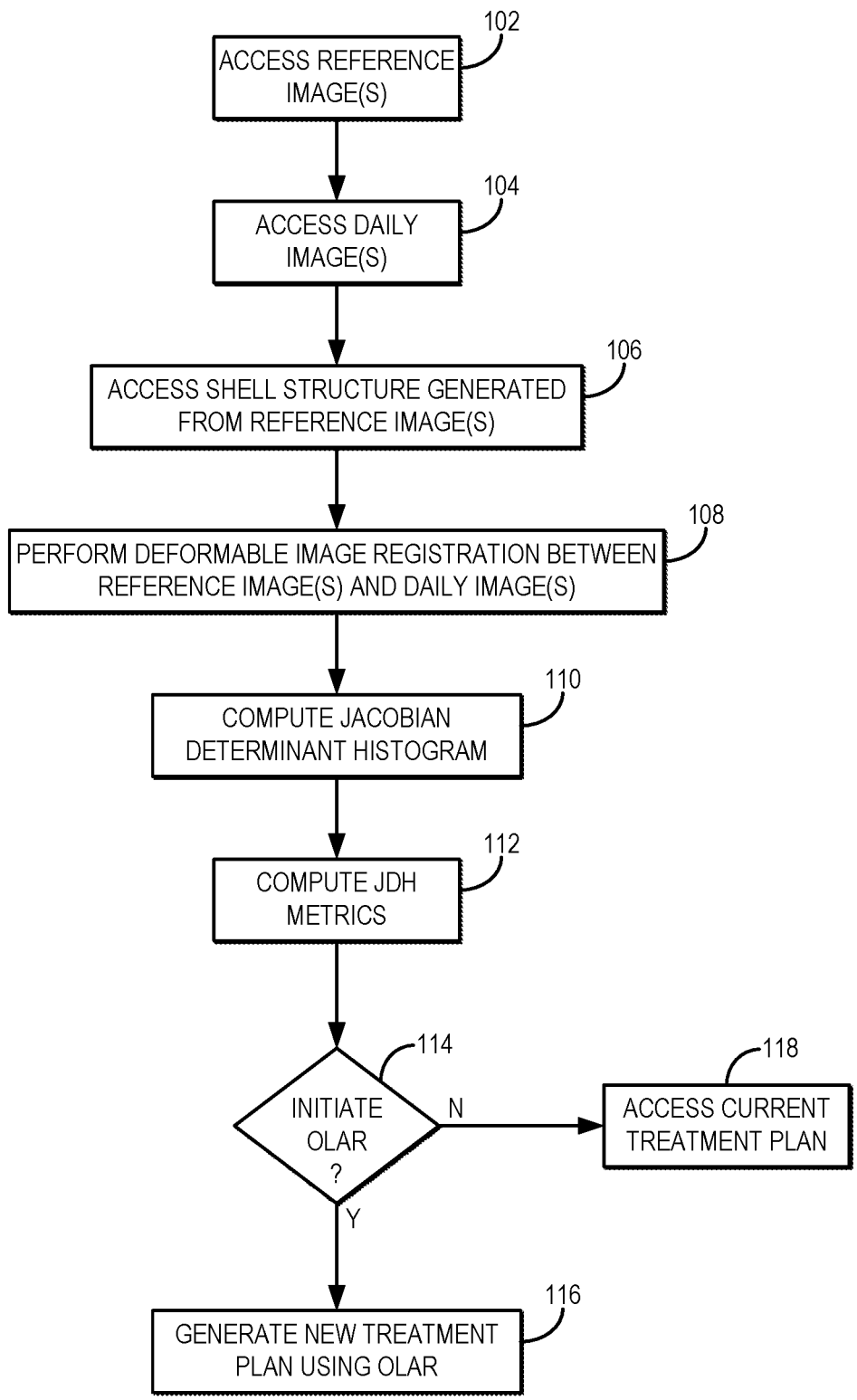
FIG. 1 is a flowchart setting forth the steps of a method for generating an indication of whether to initiate an online adaptive replanning ("OLAR") based on an analysis of metrics computed from a Jacobian determinant histogram generated from a deformable image registration between reference images and daily images of a patient.

Described here are systems and methods for improved online adaptive radiation therapy ("ART"). The improvements to online ART are generally provided based on the use of textural analysis and machine learning algorithms implemented with a hardware processor and a memory. The systems and methods described in the present disclosure enable significant improvements to existing online ART technology and the development of improved online ART planning systems. Particularly, the systems and methods significantly improve the efficiency and accuracy of online ART, thereby improving radiation therapy delivery. As a result, safer and more effective radiation treatment plans can be produced and used to deliver treatment to patients. Moreover, the systems and methods described in the present disclosure enable OLAR to be implemented in clinically acceptable timeframes. For example, OLAR can be reduced from taking 10-30 minutes down to 5-10 minutes.

For instance the systems and methods described in the present disclosure can rapidly identify the necessity of online adaptive replanning ("OLAR"). In an example implementation, this can be done by analyzing Jacobian determinant histogram features or other metrics from the deformable registration of a reference image and the image of the day. The systems and methods described in the present disclosure can also automatically and rapidly identify good-quality contours generated by auto-segmentation using image texture analysis, and can automatically correct contours that have been identified as being inaccurate. The systems and methods described in the present disclosure also provide for automated plan quality evaluation based on 3D dose texture features. The systems and methods described in the present disclosure can also rapidly create synthetic computed tomography ("CT") images from magnetic resonance images. As one example, this process can be implemented by automatically segmenting air and bone regions in the magnetic resonance images.

Thus, in some aspects, the systems and methods described in the present disclosure provide for rapidly identifying those instances where online ART are needed or otherwise beneficial. As mentioned above and described in detail below, this evaluation can be based on analyzing Jacobian determinant histogram features or other metrics from the deformable registration of a reference image with an image of the patient obtained on the day of treatment.

In some other aspects, the systems and methods described in the present disclosure provide for contour correction, contour verification, or both. As mentioned above, and described in detail below, contours can be automatically identified as being good quality, and those contours identified as being inaccurate can be automatically corrected.

In still other aspects, the systems and methods described in the present disclosure provide for automatic radiation treatment plan evaluation. As mentioned above and described in detail below, the radiation treatment plan evaluation can be implemented based on an analysis of 3D dose texture features.

As another example, in some aspects, the systems and methods described in the present disclosure provide for synthetic CT. As mentioned above and described in detail below, synthetic CT images can be generated from magnetic resonance images. As an example, the synthetic CT images can be generated from magnetic resonance images that have been processed to accurately segment air and bone regions.

OLAR can account for inter-fractional variations during RT, but is a generally time-consuming and labor-intensive process when compared to other methods, such as the repositioning method. Repositioning is enough for minimal inter-fractional deformations. Therefore, determining indications for when OLAR is desirable. Described here is a method to rapidly determine whether OLAR is needed, or would otherwise be beneficial. In an example, the technique includes analyzing the Jacobian determinant histogram obtained from deformable image registration between reference images (e.g., planning images) and daily images (e.g., images obtained on the day of treatment).

Referring now to FIG. 1, a flowchart is illustrated as setting forth the steps for determining an indication of whether to initiate OLAR to generate a new radiation treatment plan. The method includes accessing with a computer system, reference images, as indicated at step 102, and daily images, as indicated at step 104. As noted above, the reference images may also be referred to as planning images, and are generally images of the patient that were acquired before the day of treatment. The daily images are generally images of the patient that are acquired on the day of treatment. Accessing these images can include retrieving previously acquired images from a memory or other data storage, or in the instance of the daily images, can include acquiring the daily images with a suitable medical imaging system, such as a CT system or an MRI system.

As indicated at step 106, a shell structure is generated from the reference images and is also accessed with the computer system. The shell structure may be, for example, a shell structure having a particular thickness that has been, or is, created surrounding a tumor, an OAR, or another critical structure depicted in one or more of the reference images. As one example, the shell structure can have a thickness of 10 mm. As another example, the shell structure can have a thickness of 5 mm. More generally, the shell structure can have a thickness greater than, or less than, 10 mm.

As indicated at step 108, a deformable image registration ("DIR") between the reference images and the daily images is performed. The DIR may be performed, for instance, based in part on the shell structure generated from the reference images. A Jacobian determinant histogram ("JDH") is computed based on the deformable image registration, as indicated at step 110. For instance, the JDH can be computed based on the determinant of the Jacobian matrix of the deformation field estimated in the DIR. One or more metrics of the JDH are computed, as indicated at step 112. As an example, the metrics can include minimum values ("min"), maximum values ("max"), full width at half maximum ("FWHM"), peak, standard deviation, skewness, or combinations thereof. An indication whether OLAR should be initiated is generated at step 114 based on the one or more JDH metrics. For example, if one of the JDH metrics fails to satisfy pre-established criteria, then an indication that OLAR should be initiated is produced. The indication can be produced and provided to a user, such as by generating a display element that is displayed to a user on a graphical user interface ("GUI"). In other implementations, the indication can prompt a user to initiate OLAR.

As one example for prostate cancer, if the min JDH is less than 0.47, then an indication that OLAR is advantageous, and optionally should be initiated, can be generated. As another example, if the min JDH is greater than 0.47 and skewness is greater than 1.45, but FWHM is less than 0.037, then an indication that repositioning is sufficient for the fraction during radiation therapy for prostate cancer can be generated.

When an indication that OLAR should be initiated is generated at decision block 114 a new treatment plan is generated using OLAR and the new treatment plan is used to provide radiation therapy to the patient, as indicated at step 116. Otherwise, the current treatment plan is accessed and used to provide radiation therapy to the patient, as indicated at step 118.

Figure 2:
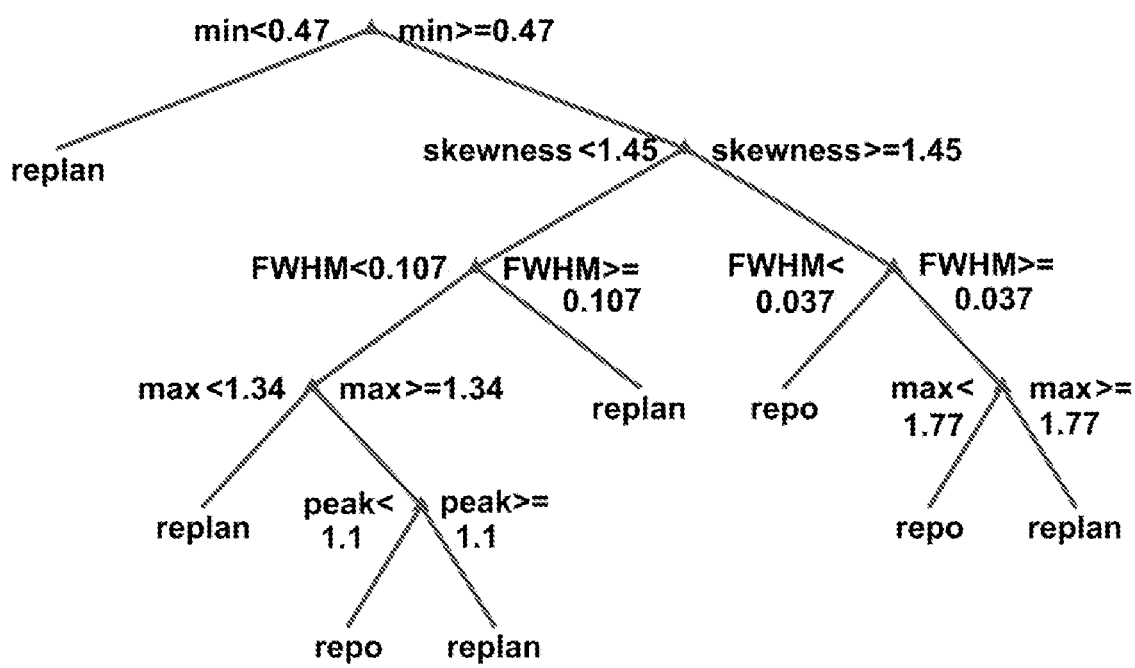
FIG. 2 is an example of a decision tree that can be obtained from using a machine learning algorithm to determine JDH metrics and criteria for generating an indication of whether it is advantageous to initiate OLAR. In this example, the decision tree has been obtained for identifying whether it would be advantageous to perform OLAR during radiation treatment for prostate cancer.

In some instances, a machine learning algorithm can be implemented with a hardware processor and memory of the computer system in order to identify metrics of the JDH, criteria for the metrics, or both, which can be used to provide the indication of whether OLAR is advantageous, and optionally can be used to provide an indication that OLAR should be initiated. As one example, the machine learning algorithm can be used to train a complex decision tree with appropriate JDH metrics, which can predict the indication of whether OLAR would be advantageous and optionally whether to initiate OLAR. An example of such a decision tree is shown in FIG. 2.

In one example study, the method described above was demonstrated on daily CTs acquired using an in-room CT during CT-guided RT for prostate cancer. DIR between daily and reference CTs was performed. JDHs were extracted from prostate and a uniform 10 mm expansion around. Using a machine learning algorithm, which may include a supervised machine learning algorithm, a complex decision tree was trained with appropriate JDH metrics that can predict the need for OLAR for a daily CT set. Sixty daily CTs from 12 randomly selected prostate cases were used as the training dataset for the classifier, with dosimetric plans for both OLAR and repositioning used to determine the classes. The resulting classification tree was tested using an independent dataset of 45 daily CTs from nine other patients with 5 CTs each. Accumulated doses from 5 fraction plans of different strategies were compared. Accumulated doses with hybrid OLAR and repositioning (using a classification tree) were comparable to all OLAR fractions.

Figure 3:
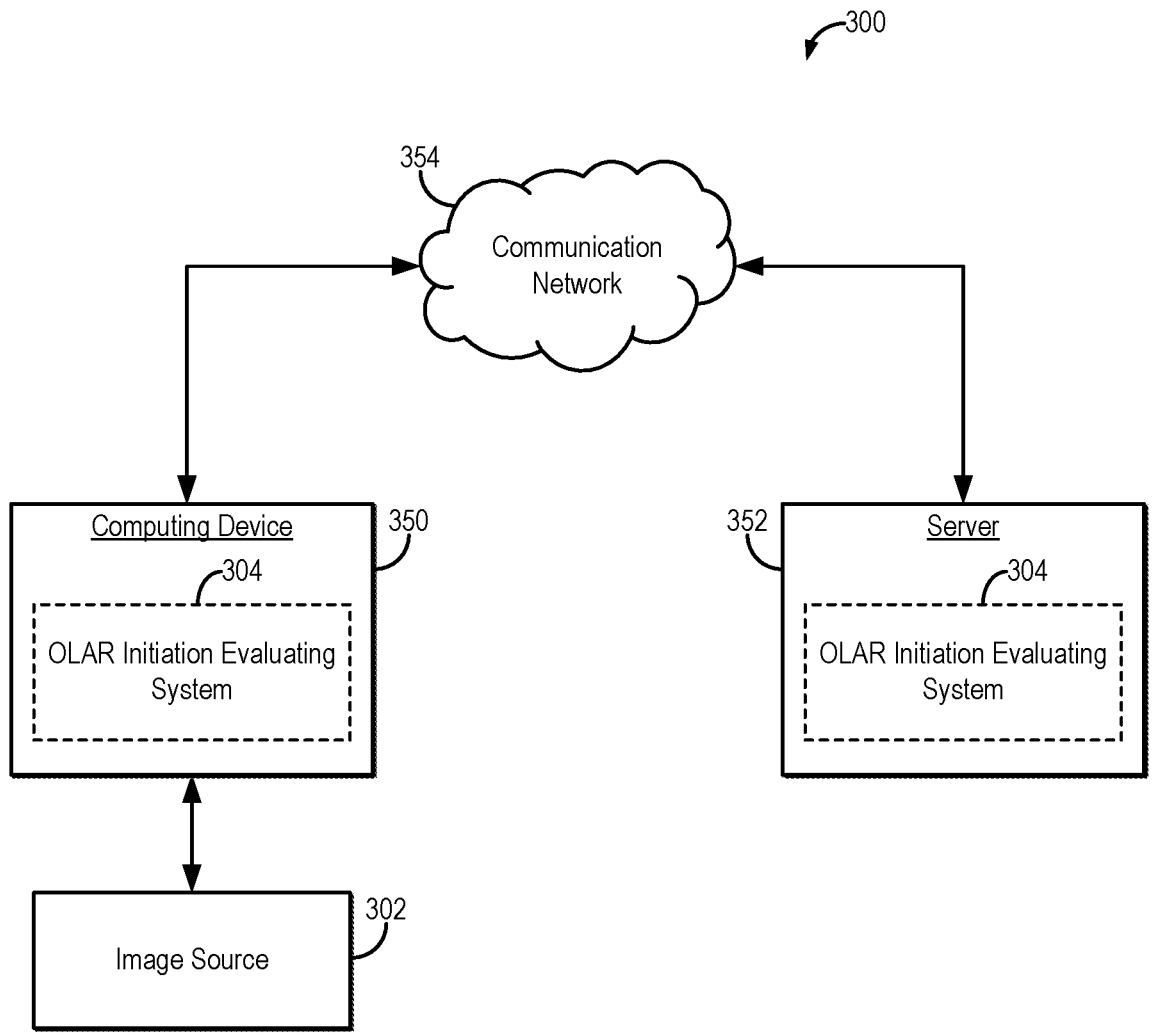
FIG. 3 is a block diagram of an example system analyzing medical image data to assess whether to initiate or otherwise implement OLAR in accordance with embodiments described in the present disclosure.

Referring now to FIG. 3, an example of a system 300 for analyzing medical image data to assess whether to implement OLAR in accordance with some embodiments of the systems and methods described in the present disclosure is shown. As shown in FIG. 3, a computing device 350 can receive one or more types of data (e.g., medical image data) from image source 302, which may be a medical image source. In some embodiments, computing device 350 can execute at least a portion of an OLAR initiation evaluating system 304 to determine whether to initiate OLAR to generate an updated radiation treatment plan from data received from the image source 302.

Additionally or alternatively, in some embodiments, the computing device 350 can communicate information about data received from the image source 302 to a server 352 over a communication network 354, which can execute at least a portion of the OLAR initiation evaluating system 304. In such embodiments, the server 352 can return information to the computing device 350 (and/or any other suitable computing device) indicative of an output of the OLAR initiation evaluating system 304.

In some embodiments, computing device 350 and/or server 352 can be any suitable computing device or combination of devices, such as a desktop computer, a laptop computer, a smartphone, a tablet computer, a wearable computer, a server computer, a virtual machine being executed by a physical computing device, and so on. The computing device 350 and/or server 352 can also reconstruct images from the data.

In some embodiments, image source 302 can be any suitable source of image data (e.g., measurement data, images reconstructed from measurement data), such as a CT system, an MRI system, another computing device (e.g., a server storing image data), and so on. In some embodiments, image source 302 can be local to computing device 350. For example, image source 302 can be incorporated with computing device 350 (e.g., computing device 350 can be configured as part of a device for capturing, scanning, and/or storing images). As another example, image source 302 can be connected to computing device 350 by a cable, a direct wireless link, and so on. Additionally or alternatively, in some embodiments, image source 302 can be located locally and/or remotely from computing device 350, and can communicate data to computing device 350 (and/or server 352) via a communication network (e.g., communication network 354).

In some embodiments, communication network 354 can be any suitable communication network or combination of communication networks. For example, communication network 354 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 3 can each be any suitable communications link or combination of communications links, such as wired links, fiber optic links, Wi-Fi links, Bluetooth links, cellular links, and so on.

Figure 4:
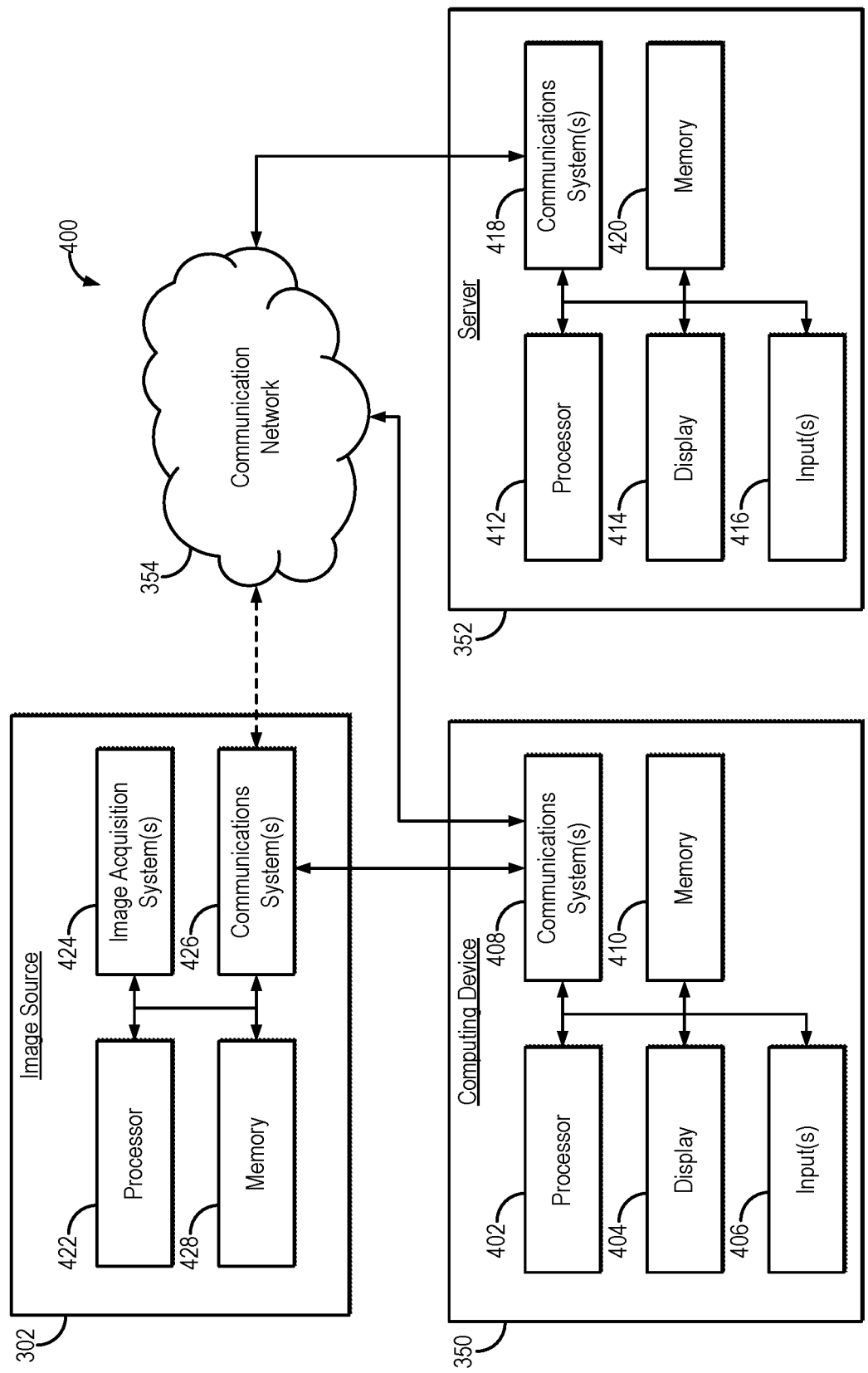
FIG. 4 is a block diagram of example components that can implement the OLAR initiation evaluating system of FIG. 3.

Referring now to FIG. 4, an example of hardware 400 that can be used to implement image source 302, computing device 350, and server 354 in accordance with some embodiments of the systems and methods described in the present disclosure is shown. As shown in FIG. 4, in some embodiments, computing device 350 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, and so on. In some embodiments, inputs 406 can include any suitable input devices and/or sensors that can be used to receive user input, such as a keyboard, a mouse, a touchscreen, a microphone, and so on.

In some embodiments, communications systems 408 can include any suitable hardware, firmware, and/or software for communicating information over communication network 354 and/or any other suitable communication networks. For example, communications systems 408 can include one or more transceivers, one or more communication chips and/or chip sets, and so on. In a more particular example, communications systems 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, data, or the like, that can be used, for example, by processor 402 to present content using display 404, to communicate with server 352 via communications system(s) 408, and so on. Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, and so on. In some embodiments, memory 410 can have encoded thereon, or otherwise stored therein, a computer program for controlling operation of computing device 350. In such embodiments, processor 402 can execute at least a portion of the computer program to present content (e.g., images, user interfaces, graphics, tables), receive content from server 352, transmit information to server 352, and so on.

In some embodiments, server 352 can include a processor 412, a display 414, one or more inputs 416, one or more communications systems 418, and/or memory 420. In some embodiments, processor 412 can be any suitable hardware processor or combination of processors, such as a CPU, a GPU, and so on. In some embodiments, display 414 can include any suitable display devices, such as a computer monitor, a touchscreen, a television, and so on. In some embodiments, inputs 416 can include any suitable input devices and/or sensors that can be used to receive user input, such as a keyboard, a mouse, a touchscreen, a microphone, and so on.

In some embodiments, communications systems 418 can include any suitable hardware, firmware, and/or software for communicating information over communication network 354 and/or any other suitable communication networks. For example, communications systems 418 can include one or more transceivers, one or more communication chips and/or chip sets, and so on. In a more particular example, communications systems 418 can include hardware, firmware and/or software that can be used to establish a Wi-Fi connection, a Bluetooth connection, a cellular connection, an Ethernet connection, and so on.

In some embodiments, memory 420 can include any suitable storage device or devices that can be used to store instructions, values, data, or the like, that can be used, for example, by processor 412 to present content using display 414, to communicate with one or more computing devices 350, and so on. Memory 420 can include any suitable volatile memory, non-volatile memory, storage, or any suitable combination thereof. For example, memory 420 can include RAM, ROM, EEPROM, one or more flash drives, one or more hard disks, one or more solid state drives, one or more optical drives, and so on. In some embodiments, memory 420 can have encoded thereon a server program for controlling operation of server 352. In such embodiments, processor 412 can execute at least a portion of the server program to transmit information and/or content (e.g., data, images, a user interface) to one or more computing devices 350, receive information and/or content from one or more computing devices 350, receive instructions from one or more devices (e.g., a personal computer, a laptop computer, a tablet computer, a smartphone), and so on.

In some embodiments, image source 302 can include a processor 422, one or more image acquisition systems 424, one or more communications systems 426, and/or memory 428. In some embodiments, processor 422 can be any suitable hardware processor or combination of processors, such as a CPU, a GPU, and so on. In some embodiments, the one or more image acquisition systems 424 are generally configured to acquire data, images, or both, and can include a CT system, and MRI system, or both. Additionally or alternatively, in some embodiments, one or more image acquisition systems 424 can include any suitable hardware, firmware, and/or software for coupling to and/or controlling operations of a CT system, and MRI system, or both. In some embodiments, one or more portions of the one or more image acquisition systems 424 can be removable and/or replaceable.

Note that, although not shown, image source 302 can include any suitable inputs and/or outputs. For example, image source 302 can include input devices and/or sensors that can be used to receive user input, such as a keyboard, a mouse, a touchscreen, a microphone, a trackpad, a trackball, and so on. As another example, image source 302 can include any suitable display devices, such as a computer monitor, a touchscreen, a television, etc., one or more speakers, and so on.

In some embodiments, communications systems 426 can include any suitable hardware, firmware, and/or software for communicating information to computing device 350 (and, in some embodiments, over communication network 354 and/or any other suitable communication networks). For example, communications systems 426 can include one or more transceivers, one or more communication chips and/or chip sets, and so on. In a more particular example, communications systems 426 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 428 can include any suitable storage device or devices that can be used to store instructions, values, data, or the like, that can be used, for example, by processor 422 to control the one or more image acquisition systems 424, and/or receive data from the one or more image acquisition systems 424; to images from data; present content (e.g., images, a user interface) using a display; communicate with one or more computing devices 350; and so on. Memory 428 can include any suitable volatile memory, non-volatile memory, storage, or any suitable combination thereof. For example, memory 428 can include RAM, ROM, EEPROM, one or more flash drives, one or more hard disks, one or more solid state drives, one or more optical drives, and so on. In some embodiments, memory 428 can have encoded thereon, or otherwise stored therein, a program for controlling operation of image source 302. In such embodiments, processor 422 can execute at least a portion of the program to generate images, transmit information and/or content (e.g., data, images) to one or more computing devices 350, receive information and/or content from one or more computing devices 350, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

As noted above, accurate segmentation based on daily images of a patient (i.e., images obtained on the day of radiation treatment, such as immediately before radiation delivery) is a significant challenge for online ART replanning. Available auto-segmentation technologies cannot always generate accurate contours. The systems and methods described in the present disclosure provide for automatically correcting inaccurate contours generated from auto-segmentation using image texture information.

In general, initial contours generated by auto-segmentation are evaluated on a slice basis against ground truth contours (e.g., contours delineated by an experienced radiation oncologist). The initial contours are regarded as inaccurate based on one or more similarity criteria compared with the ground truth. The inaccurate contours are re-processed using a texture-based automatic contour correction method. The procedure generally includes two steps: calculating voxel-based texture feature map (e.g., a GLCM-cluster shade texture feature map using 3×3 block size inside a region-of-interest ("ROI") created from the initial contour), and incorporating the texture feature map into an active contour algorithm as an external force to find correct structure boundaries.

The integration of MRI and radiation therapy (e.g., with an integrated linear accelerator, or linac) can provide high contrast real-time MRI images for daily online treatment adaption. Image of the day (i.e., images obtained on the day of treatment) can help to account for inter-fractional anatomy changes and thus deliver the radiation dose more precisely. Among the whole chain of online adaptive replanning, tumor and normal tissue contouring on the daily images is one of the most time-consuming procedures, which restricts the clinical application of online ART.

In current radiology practice, the interpretation of clinical images mainly relies on visual assessment or some qualitative metrics based on image intensities. More quantitative pathophysiological information is still unrevealed within the images. Quantitative texture feature analysis has been introduced into the radiation oncology domain for comprehensive disease characterization and early prediction of treatment response. Recently, texture information has been employed for automatic segmentation algorithms. An active contour model, also called the "snake" model is one such algorithms. The adaptation process of the snake model attracts the active shape (e.g., a 2D contour or a 3D surface) to desired image features, such as specific intensity, image edge, or texture patterns.

One known difficulty of the snake model is the determination of initial shape and position of the active curve. If the snake is initialized too far from the actual boundary, the results may not be able to cover the object boundary. On the other hand, if the initial contour is close and of similar shape to the actual contour, the performance of the snake model can be greatly improved in terms of both accuracy and efficiency.

The systems and methods described in the present disclosure address this problem by providing a fast and semi-automatic contour correction method that incorporates quantitative image texture features into an active contour model. As an example, auto-generated contours through inter-fractional deformable registration can be used as initial curves for a contouring algorithm, such as the snake model. In doing so, the prior structure knowledge is used to help guide the segmentation of new images.

Figure 5:
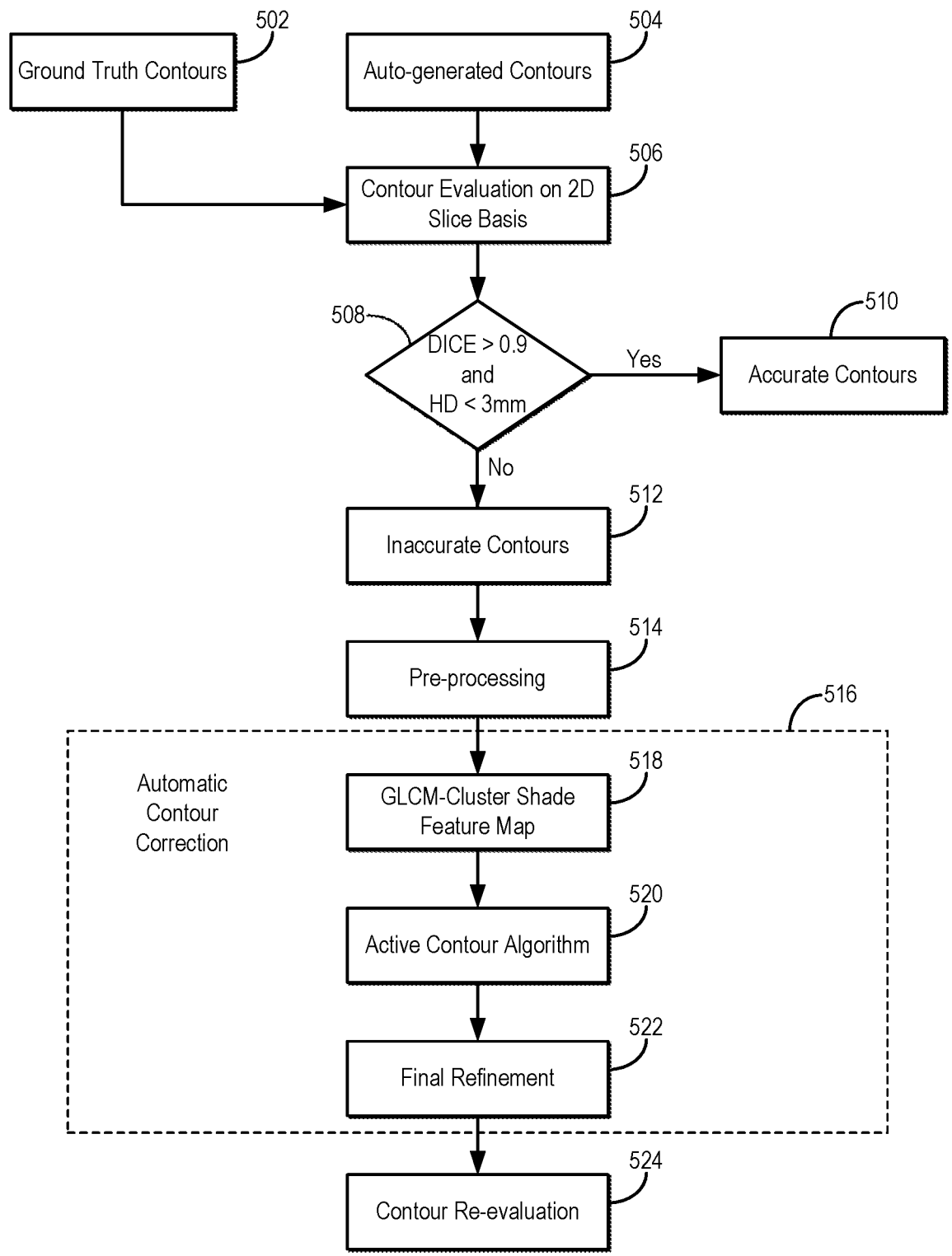
FIG. 5 is a flowchart of a texture feature-based automatic contour correction method.

The workflow of an example texture-based automatic contour correction method is shown in FIG. 5. Ground truth contours are accessed with a computer system at step 502, and auto-generated initial contours are accessed with the computer system at step 504. The initial contours are evaluated on a 2D slice basis against the ground truth contours at step 506. The contours are evaluated at decision block 508 and regarded as inaccurate if a similarity criterion is not satisfied. As one example, a Dice Coefficient ("DICE") greater than 0.9, or a Hausdorff Distance ("HD") less than 3 mm as compared with the ground truth can be used as the similarity criterion. If the contours are identified as accurate they are stored for use at step 510. If the contours are identified as inaccurate they are stored for additional processing at step 512.

The identified inaccurate slices are then pre-processed at step 514 to prepare the input images and contours for further procedures. The input images may be magnetic resonance images, CT images, ultrasound images, or any image acquired with a suitable imaging modality. For example, the inhomogeneities in the magnetic fields of the MRI machine may cause a bias field that will corrupt the images, such as by causing inhomogeneous gray level distribution across the image and blurred edges and boundaries. A preprocessing step can be performed to correct for effect of bias field. In addition, a non-linear bilateral filtering can be applied to smooth MRI images so as to reduce noise while preserving the edges.

The automatic contour correction method 516 starts with the GLCM texture feature map calculation, which may be calculated for an ROI created from initial contour at step 518. In some implementations, efficiency can be accelerated by extracting texture features for an ROI that is created by adding a margin (e.g., a 10 mm margin) to the bounding box of the initial contour. For each voxel within the ROI, each voxel value was replaced by a GLCM texture feature derived from a block (e.g., a 3×3 block) around the voxel-of-interest. The GLCM feature may be in some instances a GLCM cluster shade feature, which is advantageous due to its ability to enhance the tissue boundary contrast. The block units with gray level variance across the voxels will have higher GLCM cluster shade feature values, while the homogenous blocks will have smaller feature values. Depending on the number of gray levels used for the GLCM calculation, shape edges can have extremely high magnitude due to the third power on its calculation equation.

$$P_{CLS}(\theta, d) = \sum_{i=0}^{N-1}\sum_{j=0}^{N-1}(i+j-\mu_x(\theta,d)-\mu_y(\theta,d))^3 p(i,j,\theta,d); \quad (1)$$

$$\mu_x(\theta, d) = \sum_{i=0}^{N-1} ip_x(i, \theta, d) \quad (2)$$
$$= \sum_{i=0}^{N-1}\sum_{j=0}^{N-1} ip(i,j,\theta,d); \mu_y(\theta,d)$$
$$= \sum_{j=0}^{N-1} jp_y(j,\theta,d)$$
$$= \sum_{i=0}^{N-1}\sum_{j=0}^{N-1} jp(i,j,\theta,d)$$

where $p(i,j,\theta,d)$ is the GLCM matrix element, which contains the statistical probability for a pair of pixels of gray levels i and j at a particular displacement distance d and at a particular angle ($\theta$). In some implementations, the original images can first be rescaled to reduce the number of gray levels. The size of GLCM matrix can be determined by the number of gray levels. To avoid direction dependency, the matrix can be accumulated along 4 angles, i.e., $\theta$=0, 45, 90, 135. The distance d between two pixels can be chosen as 1.

The feature map is then integrated into an active contour algorithm as external force to find correct structure boundaries as indicated at step 520. The active contour model can generally include three phases: initialization, deformation, and termination. As one example, the auto-generated contours through inter-fractional deformable registration can be used as initial curves for the snake model. During the deformation stage, the snake model moves the contour points by minimizing an energy function. As shown in Eqn. (3), the energy function ($E_{snake}$) is composed of two terms: internal energy ($E_{int}$) and external energy ($E_{ext}$).

$$E_{Snake} = \sum_{s=1}^{N} [E_{int}(v(s)) + E_{ext}(v(s))]; \quad (3)$$

where v(s) is the contour point, and N is the total number of contour points.

As shown in Eqn. (4), the internal energy can be further divided into two energy components: elasticity and ending forces, which are the first and second derivatives of the contour, respectively.

$$E_{int} = \frac{1}{2}\left\{\alpha \times \left|\frac{dv(s)}{ds}\right|^2 + \beta \times \left|\frac{dv(s)^2}{ds^2}\right|^2\right\}; \quad (4)$$

The $\alpha$ and $\beta$ represents weighting factor for each term. The elasticity force controls the tension of the snake, while the bending force controls the rigidity of the snake. During the deformation process, the weighting factors can be tuned to adjust the smoothness of the curve to better match the shape of the subject boundary. The internal force is only related to the shape of the curve during iteration, it is independent of image features.

The calculated GLCM Cluster Shade feature map was used as external force to guide the active curve to find the actual boundary, the feature value of which is relatively high compared with homogeneous regions. The traditional snake model has a problem that external force only exists at the edge. For points located inside the homogeneous region of the organ, the active contour may not be able to converge to the boundary. To solve this problem, a "balloon force" can be added to the external energy function, as shown in Eqn. (5). The balloon force, as shown in Eqn. (6), is calculated along the normal direction of the curve, where is the weighting factor of balloon force. During the snake evaluation, the parameter can be regarded as step size for snake movement.

$$E_{ext} = -\gamma \times |E_{CLS}(v(s))| - E_{balloon}(v(s)) \quad (5);$$

$$E_{balloon}(v(s)) = \zeta(v(s)) \times \mu \times \overrightarrow{n(s)}; \quad (6)$$
$$\zeta(v(s)) = \begin{cases} 1 & E_{CLS}(v(s)) \geq Tre \\ 0 & E_{CLS}(v(s)) < Tre \end{cases}$$

where n(s) is the normal unitary vector of the curve at v(s). To avoid the contour leakage caused by the balloon force, a binary threshold function ((v(s)) can be applied. The balloon force is only activated for contour points with feature values lower than the pre-determined threshold. For high feature value points, the balloon force equals zero. As one example, the threshold can be selected as a constant, such as a constant of 50.

As described above, there are a total of four weighting factors for each term of the snake model. Those factors have a significant impact in the snake's behaviors and the performance of the deformation process. Moreover, the inherent characteristic of the MRI images cause large inter-patient and even intra-patient variance. Each image set is benefitted by a different set of parameter values for the snake to perform well. To solve this problem, a user interface can be used to interactively tune the key parameters for each image set. The parameters can be tuned based on the contour correction performance of a sample slice. The values can be applied to the remaining slices to improve the efficiency. They can also be tuned for each slice as desired.

A default maximum number of iterations executed in the deformation process can be set, such as using a value of 300 total iterations. In other implementations, an overlap area change ratio ("CR") can also be computed and stored for each iteration. If the CR is smaller than 0.01 for a successive number of iterations (e.g., five iterations), which means the snake converged to a stable status, the iteration process can also be terminated.

After active contouring, morphological operations are performed to refine the contours at step 522. In the end, DSC and HD were re-calculated on the corrected contours to evaluate the performance of the proposed method at step 524. The updated contours can be stored and used for later use.

Figures 6A, 6B, 6C:
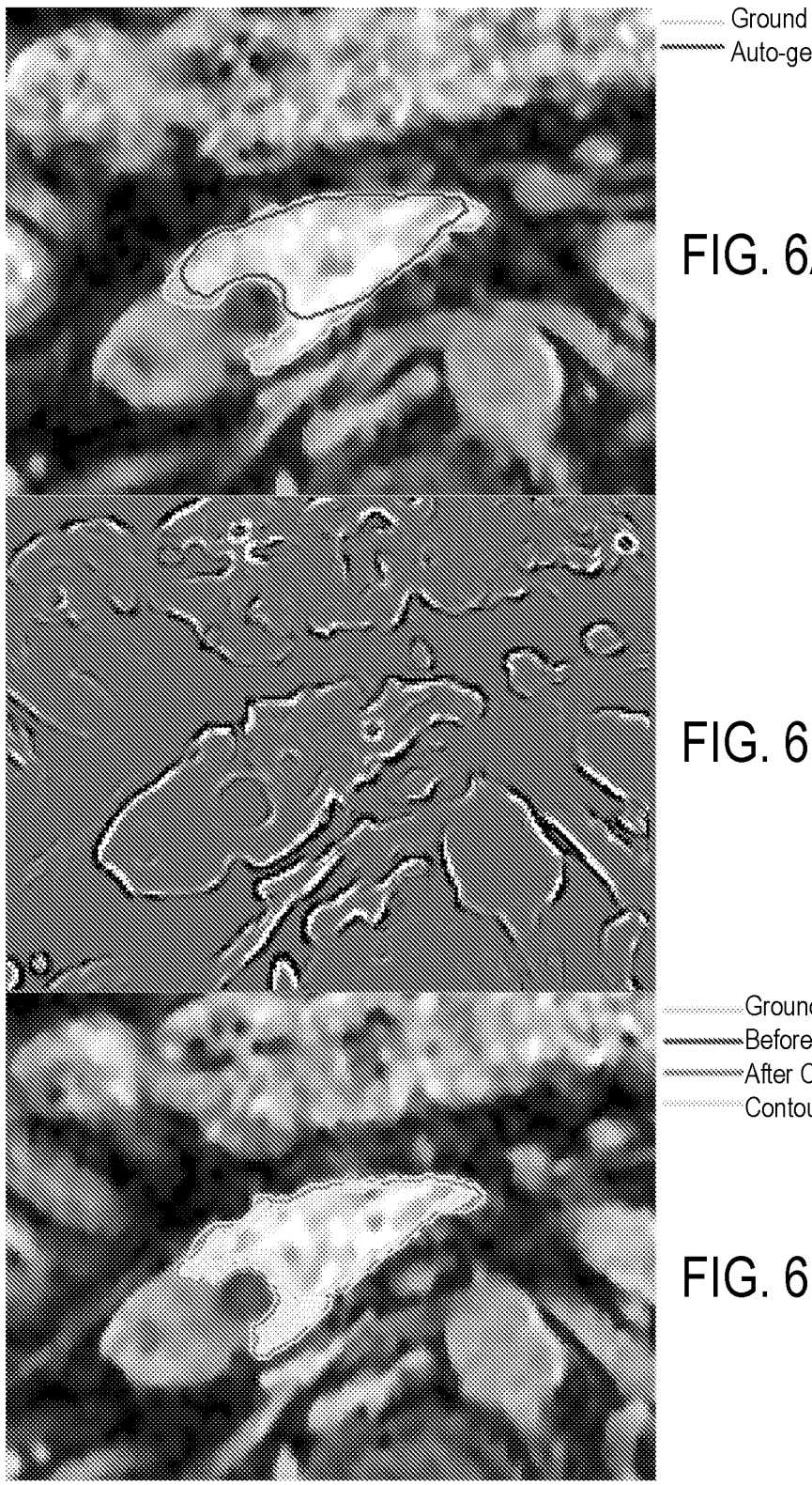
FIGS. 6A-6C show representative examples for texture based active contour model. Ground truth (green) and auto-generated contours are shown in FIG. 6A. A GLCM-cluster shade feature map is shown in FIG. 6B. Contour evolvement plots are shown in FIG. 6C. The evolving contours are illustrated with cyan lines, while ground truth contour, initial contour, and corrected contour are highlighted with different colors (i.e., green, blue, and red).

A representative example is shown in FIGS. 6A-6C to illustrate the texture based contour correction method described above. FIG. 6A shows the ground truth contour as well as the contour generated from intra-fractional deformable registration. Due to the large deformation between the different fractions, the contour algorithm used in this example failed to generate accurate pancreatic head contour for this slice. FIG. 6B shows the calculated GLCM-cluster shade feature map, in which the boundary between pancreatic head and the surrounding tissue is enhanced compared with original MRI image. The evolving contours are illustrated with cyan lines, while ground truth contour, initial contour, and corrected contour are highlighted with different colors (i.e., green, blue, and red) in FIG. 6C. The contour successfully converged to the ground truth after correction.

The image-texture based automatic contour correction approach described above can be used to improve the overall contour accuracy and the efficiency of contour modification. The method may be used as a part of the segmentation process for MRI-guided online replanning.

As noted above, there is a desire to robustly validate the auto-segmented contours in online adaptive replanning ("OLAR"). The systems and methods described in the present disclosure provide a fast and automated patient-specific contour validation approach using quantitative image features (e.g., image texture features) of medical image. The medical images may be daily images (i.e., images of a patient obtained on the day of treatment) or previously acquired images of the subject, and may be CT images, MRI images, or any other suitable medical image.

The accuracy of auto-segmentations based on medical images, such as the image of the day, is a challenge for OLAR. Validation of auto-segmented contours is traditionally performed through a time-consuming manual review procedure. The systems and methods described in the present disclosure provide a fast and automated patient-specific contour validation approach using quantitative image texture features.

In fractionated RT, treatment plans generated using planning CTs ("pCTs") prior to treatment may not be optimal for a given fraction due to the inter-fraction variations. The introduction of in-room imagers, such as MRI, CT-on-rail, and cone beam CT ("CBCT"), has made visualizing patient anatomy possible on a daily basis. OLAR can be used to adapt the radiation plan in response to inter-fractional anatomy changes during the course of the treatment. The efficiency of OLAR remains a challenge because the replanning procedure needs to be done within a practical time frame while the patient is lying and waiting on the couch. Different kinds of computerized tools have been developed to increase the speed of the replanning procedure. One identified bottle-neck is the time for the delineation of target and critical organs on the image of the day.

In recent years, new techniques such as machine-learning based image auto-segmentation and deformable image registration ("DIR") based contour propagation methods have been developed and used to generate contours on the daily images. The introduction of daily MRI images is particularly useful in terms of improving quality of daily contours. As the automatically generated contours are not perfect with the currently available methods, validation and manual editing of the daily contours are generally needed in the OLAR process. Currently, the validation of contours is performed through a manual review procedure, which is time-consuming and thus impractical for OLAR. More efficient and robust automatic contour evaluation and validation methods are desired to facilitate the application of OLAR.

Medical images contain not only a visual depiction of human anatomy, but also minable data, such as quantitative pathophysiology information. Texture analysis can be a very useful image attribute in image analyses and computer vision applications. Texture features are typically computed from the statistical distribution of pixel intensity in the image. Depending on the number of intensity points (i.e., pixels) in the statistical calculation, texture features can be classified into first-order, second-order, and higher-order statistics. Those higher-order texture features have the potentials to reveal information that is hard to be visualized from the original images.

For head-and-neck cases, the shape and relative position of organs are typically stable with small variance, which makes them good candidates for applying geometric based contour assessment. In contrast, due to comprehensive reasons, such as the respiratory and bowel movements, and different filling status, abdomen and pelvis organs may present large shift and deformation. Thus, it is difficult to apply geometric based contour assessment on those organs. However, texture features can be invariable for specific organs, even with shape and location changes.

It is contemplated that each anatomic structure has distinct, quantitative image texture features that may not be visible by a human user. It is also contemplated that the differences of these image textures between the structure and the surrounding tissues can be used to identify if the contour is valid or not.

The systems and methods described in the present disclosure provide a fast and automated patient-specific contour validation approach using quantitative image texture features of the image of the day, or other medical images of a subject. As an example, for each test contour, inner and outer shells can be generated. For instance, the inner and outer shells can be generated by eroding and expanding the contour, respectively, by a set amount (e.g., 3 mm). Second-order gray level co-occurrence matrix ("GLCM") based texture features can be calculated for these inner and outer shells, and then normalized to a central region (e.g., 20% in volume) in corresponding contours. Accurate contours can be identified based on whether or not the texture values are consistent for volumes enclosed by the inner shell and significantly different for the volumes enclosed by the outer shell. Otherwise, a contour will be identified as inaccurate. An artificial intelligence ("AI")-based model can be constructed and trained to access the texture attributes for the core regions, inner shell regions, and outer shell regions. As an example, the AI-based model may be a machine learning ("ML")-based model that is constructed and trained based on supervised learning. As another example, the AI-based model can be a decision tree model. For instance, the ML-based model can implement a recursive random forest classification algorithm to rank image features and to select top-ranked features. Supervised classification models can also be implemented for contour validation. A multi-feature criterion can be derived from an accurate contours database to validate the core region. Appropriate texture features are identified as those with large different feature values between organ and surrounding tissues for the inner and outer shells evaluation. Receiver operating characteristic ("ROC") curves can be used to determine thresholds for the chosen features to discern accurate and inaccurate contours.

Contours classified as accurate can be directly used for adaptive replanning and treatment with confidence, while inaccurate contours require an additional review procedure by clinicians or correction using the methods described in the present disclosure. The contour validation methods described in the present disclosure can replace the time-consuming manual process of checking contours during online adaptation, facilitating the routine practice of OLAR.

Figure 7:
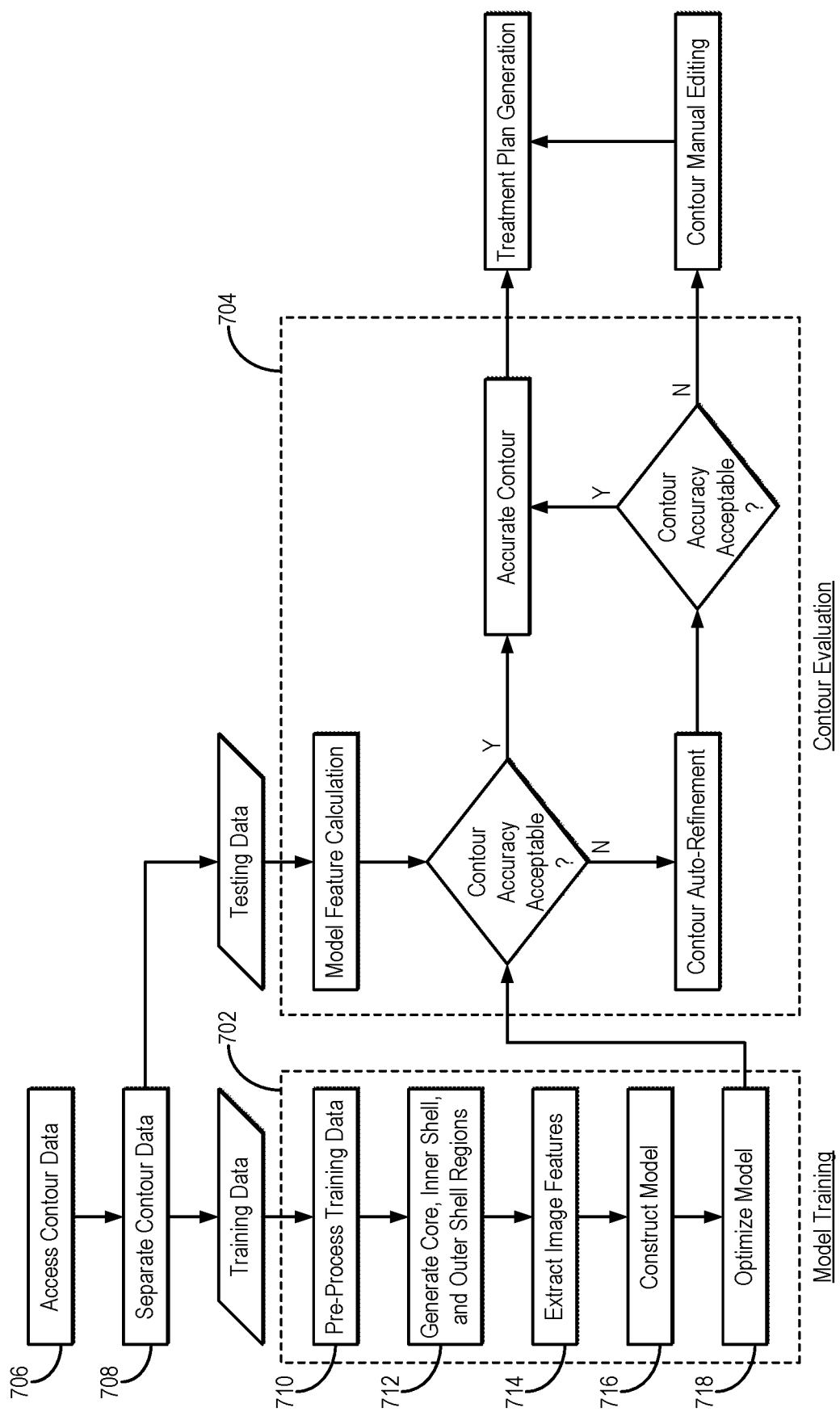
FIG. 7 is a flowchart of an example method for feature-based automated contour quality control and contour correction.

Referring now to FIG. 7, a flowchart is illustrated as setting forth the steps of an example method for automated contour validation. The method includes a model training stage 702, which may be an off-line model training stage, and a contour evaluation stage 704.

Contour data are accessed with a computer system, as indicated at step 706. The contour data generally include images of the subject and corresponding accurate contours and inaccurate contours. For instance, the contour data may include auto-generated organ contours as well as the manual generated ground truth contours. As an example, accurate contours can be identified based on multiple criterion, such as having Dice Similarity Coefficient ≥0.85, mean distance to agreement ≤1.5 mm, and 95 percent of distance to agreement ≤5 mm.

The contour data can be accessed with the computer system by retrieving these data from a memory or other storage device or medium. In some instances, accessing the contour data may include acquired images with a medical imaging system and communicating or otherwise transferring the images to the computer system. Additionally or alternatively, accessing the contour data may include generating contours from medical images and communicating or otherwise transferring those contours to the computer system.

The contour data are then separated into training data and testing data, as indicated at step 708. The training data will be used to train an AI-based model for evaluating the testing data. As an example, the contours in the contour data can be randomly separated such that a first percentage of the contour data are assigned as training data and a second percentage of the contour data are assigned as testing data. For instance, two-thirds of the contour data may be used as training data and one-third of the contour data may be used as testing data.

In the model training stage, 702 the input images and contours in the training data can be pre-processed at step 710 to facilitate the later texture feature calculations. The pre-processing step aims to prepare the input images and contours for texture extraction and to otherwise improve image quality and training efficiency of the AI-based model. Because texture is unique and uniform within a given organ, the components with known different textures should be excluded from the texture extraction to avoid deteriorating the final results.

As one example, CT images can be thresholded in the range [−200 HU, 300 HU] in order to include all soft tissue, but to exclude bone and air. Additionally or alternatively, for pancreatic patients, a threshold value of 100-150 HU can be used to exclude duodenal stent and calcifications from the pancreatic head, since the pancreatic tissue normally has CT numbers lower than 150 HU whereas the CT number for pancreatic stent usually are higher than this value. On the other hand, the gas contents within the organs may have severe effect on the calculated textures. A threshold of −30 HU can then be applied to all the chosen organs to exclude the gas areas. After setting the thresholds, the organ contours are further smoothed using morphological opening and closing filters. Additionally or alternatively, image intensity values can be rescaled, such as to reduce the number of gray levels. As an example, image intensity values can be rescaled to 250 gray levels (bin width 2 HU), 500 gray levels, or so on. MRI images can be similarly thresholded using suitable thresholding techniques.

Organ masks can be generated only considering voxels inside the contours to increase the calculation efficiency. As another example, to improve calculation efficiency, a bounding box can be defined as the minimum rectangular box that fully encloses all the contour points. The images can then be cropped by adding an expansion margin, such as a 25 mm expansion margin, to the bounding box.

To reduce image noise, bilateral filtering using two 3×3 Gaussian kernels can be applied to the cropped image. The standard deviations of the kernels in the spatial and intensity domains can be selected as 1 and 0.5, respectively. This filter-type was chosen due to its ability to preserve sharp edges. It will be appreciated that other noise reducing filters or other noise reducing algorithms could also be implemented.

A mask is then generated from each contour in the training data and the mask is subdivided into three subregions (e.g., core, inner shell, outer shell), as indicated at step 712. To obtain the core, or central, region for a given organ contour in the training data, a binary mask can be first constructed by assigning a value of 0 to any pixels inside the contour and a value of 1 to pixels outside of the contour. A distance map can then be generated using a distance metric, such as the Euclidean distance, between the pixel and nearest boundary pixel (e.g., the distance of each pixel contained within the mask to the surface of the contour). The central, core region can be determined based on a percent (e.g., 20%, 30%) of pixels with the highest values in the distance map. The inner and outer shells can be generated for each testing contour. As an example, the inner and outer shells can be generated by eroding and dilating the organ mask by a selected amount (e.g., 4 mm) on each 2D slice. A 4 mm shell thickness can be selected to identify contour errors larger than the typical clinical tolerance of 3 mm.

Image features (e.g., texture features, shape features) are then calculated, or otherwise extracted, from the core, inner shell, and outer shell regions, as indicated at step 714. As one non-limiting example, image features may include some or all of the following image features: intensity histogram-based image features, including mean, standard deviation, range, skewness, and kurtosis; gray-level co-occurrence (GLC) based image features; and gray-level run-length (GLR) based image features.

GLC and GLR matrices can be calculated by accumulating over a number of displacement angles on each slice to avoid direction dependency and then summing across all 2D slices. As one example, four angles (e.g., 0°, 45°, 90°, and 135°) can be used. As another example, nine angles (e.g., 0°, 45°, 90°, 135°, 180°, 235°, 270°, 315°, and 360°) can be used. Image features (e.g., texture features) can be extracted from each of the three subregions, separately. The distance between two pixels for calculating the GLC matrix can be chosen as 1.

The GLC-based features can be extracted from the GLC matrix ("GLCM"). The corresponding equations for some texture features are listed in Table 1 below. In an example study, three testing cases were randomly chosen and inner and outer shells were generated from the original contours with different intervals to include different amount of surrounding tissues into feature calculation. The appropriate features should have high variance between the organ and surrounding tissues. After that, during the model training procedure, inner and outer shells can be generated for each testing contour by eroding and expanding the contour by a set amount (e.g., 3 mm, 4 mm). The chosen texture features can then be calculated for both inner and outer shells and used for contour quality validation.

TABLE 1

Summary of GLCM-based texture features

| Feature Name | Equation |
|---|---|
| Cluster Tendency ($P_{CLT}$) | $P_{CLT}(\theta, d) = \sum_{i=0}^{N-1}\sum_{j=0}^{N-1}(i+j-\mu_x(\theta,d)-\mu_y(\theta,d))^2 p(i,j,\theta,d)$ |
| Variance ($P_{VAR}$) | $P_{VAR}(\theta, d) = \sum_{i=0}^{N-1}\sum_{j=0}^{N-1}(i-\mu_x)^2 p(i,j,\theta,d)$ |
| Sum Entropy ($P_{SEN}$) | $P_{SEN}(\theta, d) = -\sum_{k=0}^{2N-2} p_{x+y}(k,\theta,d)\cdot\log(p_{x+y}(k,\theta,d))$ |
| Cluster Prominence ($P_{CLP}$) | $P_{CLP}(\theta, d) = \sum_{i=0}^{N-1}\sum_{j=0}^{N-1}(i+j-\mu_x(\theta,d)-\mu_y(\theta,d))^4 p(i,j,\theta,d)$ |
| Contrast ($P_{CON}$) | $P_{CON}(\theta, d) = \sum_{i=0}^{N-1}\sum_{j=0}^{N-1}(i-j)^2 p(i,j,\theta,d)$ |
| Dissimilarity ($P_{DIS}$) | $P_{DIS}(\theta, d) = \sum_{i=0}^{N-1}\sum_{j=0}^{N-1}|i-j| p(i,j,\theta,d)$ |
| Difference Entropy ($P_{DEN}$) | $P_{DEN}(\theta, d) = -\sum_{k=0}^{N-1} p_{x-y}(k,\theta,d)\cdot\log(p_{x-y}(k,\theta,d))$ |
| Entropy ($P_{ENT}$) | $P_{ENT}(\theta, d) = -\sum_{i=0}^{N-1}\sum_{j=0}^{N-1} p(i,j,\theta)\cdot\log(p(i,j,\theta,d))$ |
| Kurtosis | $Kurtosis = \dfrac{\sum_{i=1}^{N}(Y_i-\overline{Y})^4/N}{s^4}$ |
| Skewness | $Skewness = \dfrac{\sum_{i=1}^{N}(Y_i-\overline{Y})^3/N}{s^3}$ |
| Cluster Shade ($P_{CLS}$) | $P_{CLS}(\theta, d) = \sum_{i=0}^{N-1}\sum_{j=0}^{N-1}(i+j-\mu_x(\theta,d)-\mu_y(\theta,d))^3 p(i,j,\theta,d)$ |
| Mean | $Mean = \dfrac{1}{N}\sum_{i=1}^{N} Y_i$ |
| Auto Correlation ($P_{AUC}$) | $P_{AUC}(\theta, d) = \sum_{i=0}^{N-1}\sum_{j=0}^{N-1}(i\times j)p(i,j,\theta,d)$ |
| Sum Variance ($P_{SVA}$) | $P_{SVA}(\theta, d) = \sum_{k=0}^{N-1} k^2 p_{x+y}(k,\theta,d)$ |
| Sum Average ($P_{SAV}$) | $P_{SAV}(\theta, d) = \sum_{k=0}^{2N-2} k p_{x+y}(k,\theta,d)$ |
| Informational Measure of Correlation 1 ($P_{IMC1}$) | $P_{IMC1} = \dfrac{HXY - HXY_1}{\max\{HX, HY\}}$ |
| | $HX = -\sum_{i} p_x(i,\theta,d)\log_2(p_x(i,\theta,d))$ |
| | $HX = -\sum_{j} p_y(j,\theta,d)\log_2(p_y(j,\theta,d))$ |
| | $HXY = -\sum_{i}\sum_{j} p(i,j,\theta,d)\log_2(p(i,j,\theta,d))$ |

TABLE 1-continued

Summary of GLCM-based texture features

| Feature Name | Equation |
|---|---|

$$HXY_1 = -\sum_i \sum_j p(i, j, \theta, d)\log_2(p_x(i, \theta, d) \cdot p_y(j, \theta, d))$$

Informational Measure of Correlation 2 ($P_{IMC2}$)

$$P_{IMC2} = \sqrt{1 - e^{-2(HYX_2 - HYX)}}$$

$$HXY = -\sum_i \sum_j p(i, j, \theta, d)\log_2(p(i, j, \theta, d))$$

$$HXY2 = -\sum_i \sum_j p_x(i, \theta, d) \cdot p_y(j, \theta, d) \cdot \log(p_x(i, \theta, d) \cdot p_y(j, \theta, d))$$

Correlation ($P_{COR}$)

$$P_{COR}(\theta, d) = \frac{\sum_{i=0}^{N-1}\sum_{j=0}^{N-1}(i - \mu_x(\theta, d))(j - \mu_y(\theta, d))p(i, j, \theta, d)}{\sigma_x(\theta, d)\sigma_y(\theta, d)}$$

Energy ($P_E$)

$$P_E(\theta, d) = \sum_{i=0}^{N-1}\sum_{j=0}^{N-1} p^2(i, j, \theta, d)$$

Maximum probability ($P_{MAP}$)

$$P_{MAP}(\theta, d) = \max(p(i, j, \theta, d))$$

Homogeneity ($P_{Hom}$)

$$P_{Hom} = \sum_{i=0}^{N-1}\sum_{j=0}^{N-1}\frac{P(i, j)}{1 + |i - j|}$$

Homogeneity2 ($P_{Hom2}$)

$$P_{Hom2} = \sum_{i=0}^{N-1}\sum_{j=0}^{N-1}\frac{P(i, j)}{1 + (i - j)^2}$$

Inverse Variance ($P_{IVA}$)

$$P_{IVA}(\theta, d) = \sum_{i=0}^{N-1}\sum_{j=0}^{N-1}\frac{p(i, j, \theta, d)}{(i - j)^2}$$

Inverse DiffMomentNorm ($P_{IDMN}$)

$$P_{IDMN} = \sum_{i=0}^{N-1}\sum_{j=0}^{N-1}\frac{P(i, j)}{1 + (i - j)^2}$$

Inverse Difference Norm ($P_{IDN}$)

$$P_{IDN} = \sum_{i=0}^{N-1}\sum_{j=0}^{N-1}\frac{p(i, j, \theta, d)}{1 + |i - j|}$$

$\overline{Y}$ is the mean, s is the standard deviation, and N is the number of data points on the histogram.

$$\mu_x(\theta, d) = \sum_{i=0}^{N-1} ip_x(i, \theta, d);$$

$$P_{x-y}(k, \theta, d) = \sum_{i=0}^{N-1}\sum_{j=0}^{N-1} p(i, j, \theta, d); \quad |i-j|=k$$

$$P_{x+y}(k, \theta, d) = \sum_{i=0}^{N-1}\sum_{j=0}^{N-1} p(i, j, \theta, d); \quad i+j=k$$

$$\mu_x(\theta, d) = \sum_{i=0}^{N-1} ip_x(i, \theta, d) = \sum_{i=0}^{N-1}\sum_{j=0}^{N-1} ip(i, j, \theta, d);$$

$$\mu_x(\theta, d) = \sum_{i=0}^{N-1} ip_x(i, \theta, d) = \sum_{i=0}^{N-1}\sum_{j=0}^{N-1} ip(i, j, \theta, d);$$

$$\mu_y(\theta, d) = \sum_{j=0}^{N-1} jp_y(j, \theta, d) = \sum_{i=0}^{N-1}\sum_{j=0}^{N-1} jp(i, j, \theta, d);$$

In most of texture analysis studies, in order to reduce bias and extract meaningful information during statistical analysis, subjects are usually chosen following same scan protocols, such as same scanning machine, same scanning tube voltage and current, and so on. However, in the systems and methods described in the present disclosure, a general organ contour quality check routine for practical use is provided, regardless of scanning protocols or even different organ status (e.g., normal or abnormal). These factors may affect the texture feature values, even for the same organ. To eliminate machine, scanning, and patient specific effects, feature values calculated from each shell can be normalized. As an example, feature values calculated from each shell can be normalized to the central core region (e.g., 20% in volume) in the corresponding contour.

Figure 8:
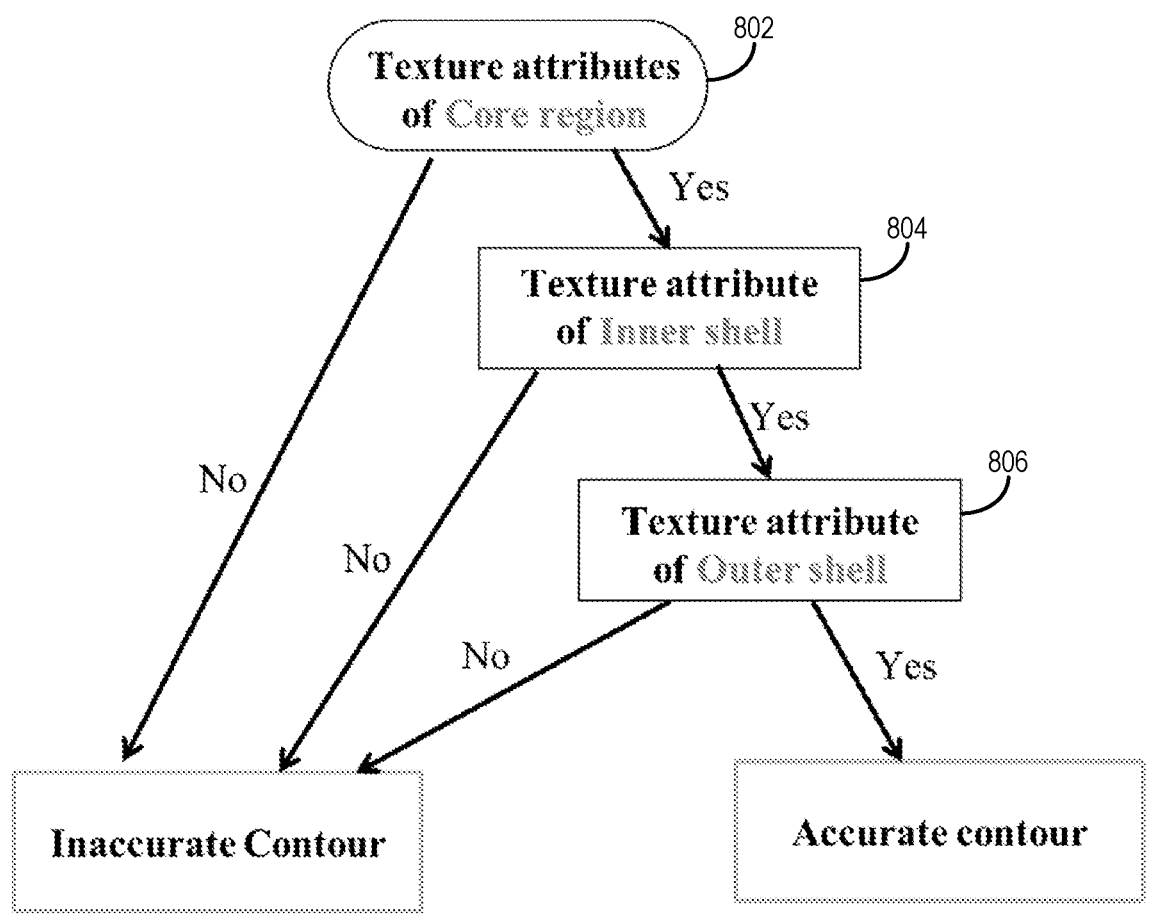
FIG. 8 is an example of a decision tree model that can be implemented for texture based contour quality validation using the methods described in the present disclosure.

An AI-based model is then constructed and used to evaluate the image feature attributes for the core, inner shell, and outer shell regions, as indicated at step 716. As noted above, in some instances the AI-based model may be a ML-based model that implements supervised learning. As one non-limiting example, the AI-based model is a decision tree model, which can be trained to access the texture attributes for core regions, inner shell regions, and outer shell regions. An example of a decision tree model is shown in FIG. 8. Decision tree models provide an effective method for data mining. In general, a decision tree model partitions data into subsets by posing a series of questions about the attributes associated with the data. Each node on the tree contains one question and has one "yes" and one "no" child node. In one example, shown in FIG. 8, a three-level decision tree is established to evaluate the texture feature attributes for core, inner shell, and outer shell regions. Contours that meet all of the attribute questions (i.e., "yes" nodes) from the three levels are identified as accurate; otherwise, the contour will be determined as inaccurate and reported for further verification.

The first level 802 of the example decision tree model shown in FIG. 8 validates the accuracy of the generated core region. The distributions of each feature from the core regions of ground truth contours can be analyzed to derive statistical confidence bounds for specific organs. As one example, to reduce feature dimensions, a correlation coefficient matrix, hierarchical clustering, or both, can be generated across all calculated texture features. Hierarchical clustering can be implemented, for instance, using Ward's Minimum Variance Clustering method. Independent, or weakly correlated, features can be identified and used for core region evaluation.

In examples where a correlation coefficient matrix is generated, the following equation can be used to compute correlation coefficients, $\rho$, $$\rho = \frac{Cov(X, Y)}{\sigma_x \sigma_y} = \frac{E[(X - \mu_x)(Y - \mu_y)]}{\sigma_x \sigma_y}; \quad (7)$$

where the operator, E, denotes the expected (mean) value of its argument; $\mu_x = E(x)$ and $\mu_y = E(y)$ are the mean of X and Y, respectively; and $\sigma_x$ and $\sigma_y$ are the standard deviation of X and Y, respectively. Each matrix element denotes the linear correlation between two variables. The correlation van vary from −1 (i.e., perfect negative correlation) through 0 (no correlation) to +1 (perfect positive correlation).

Figure 9A:
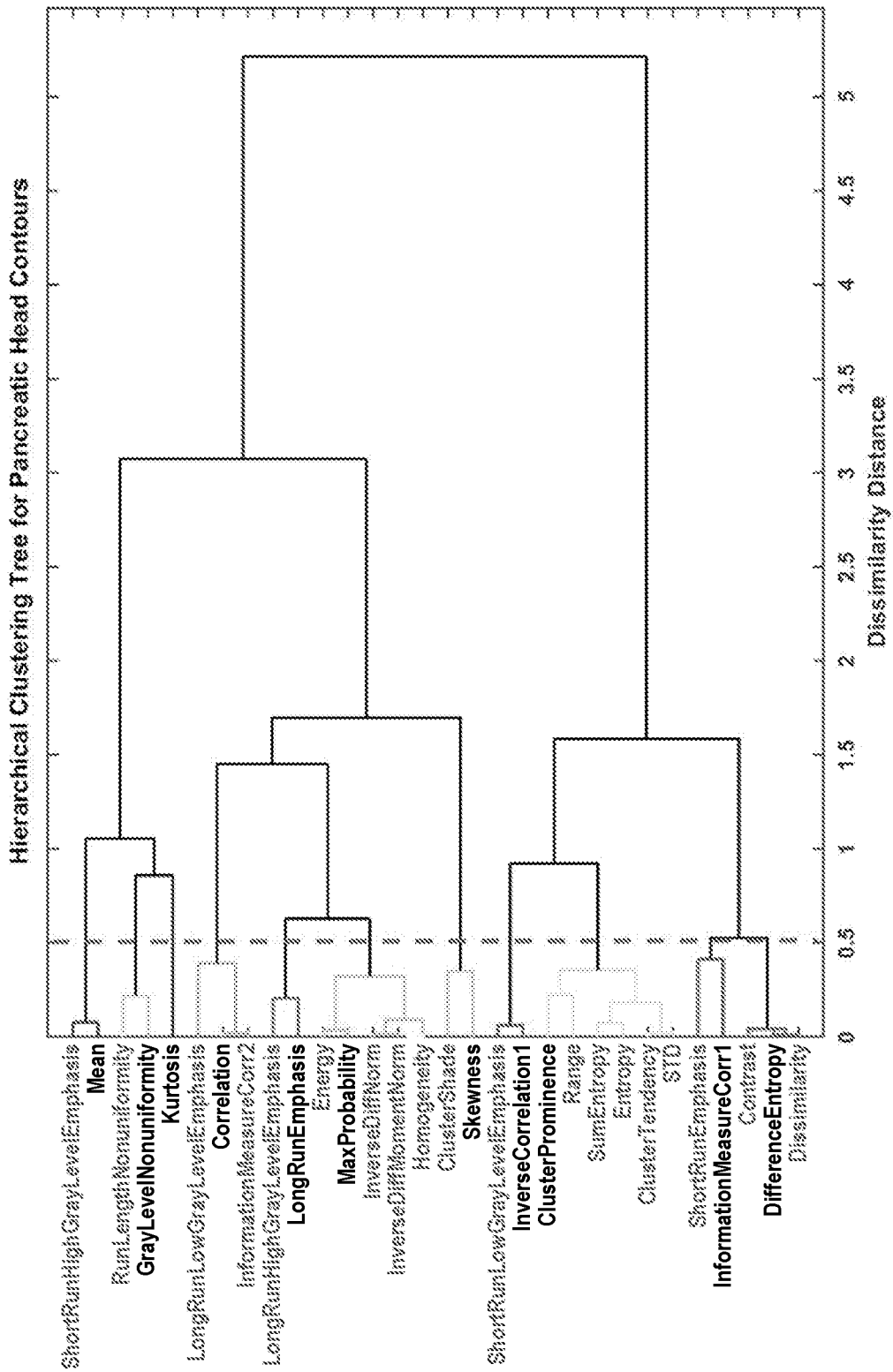
FIG. 9A is an example of a hierarchical clustering tree across the calculated texture features over core regions of ground truth pancreatic head contour. In this example, a dissimilarity distance of 0.5 was used to identify clusters. The chosen features are highlighted as yellow.
Figure 9B:
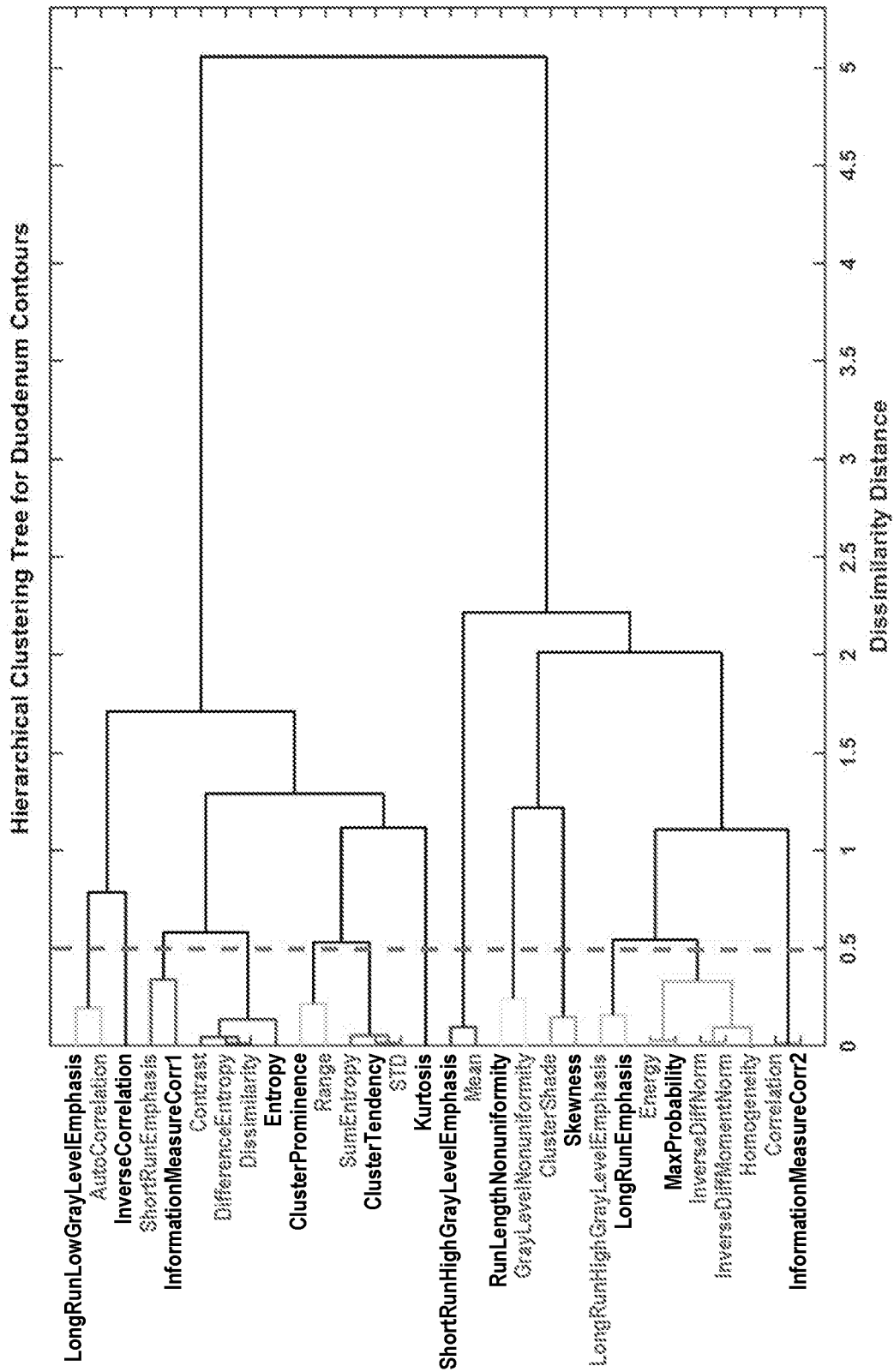
FIG. 9B is an example of a hierarchical clustering tree across the calculated texture features over core regions of ground truth duodenum contour. In this example, a dissimilarity distance of 0.5 was used to identify clusters. The chosen features are highlighted as yellow.

A dendrogram can be produced by hierarchical clustering the features using the correlation coefficients matrix. An example of dendrograms, or hierarchical clustering trees, for pancreatic head contours and duodenum contours are shown in FIGS. 9A and 9B, respectively. The x-axis in the clustering tree shows the linkage distance between two features. The smaller the distance is, the closer the two features are correlated.

As one non-limiting example, a dissimilarity distance of 0.5 can be used as a cutoff to identify clusters. Within each cluster, the feature with the minimum correlation criterion can be selected. To further reduce dimensionality, principal component analysis ("PCA") can be used on the reduced feature set to identify a set of principal components that describe 95% of the variance in the data. In these instances, the principal components are accepted as "principal features" that describe the texture properties of the core sub-regions of pancreas head and duodenum, respectively, with high reproducibility and without redundancy. The values of the principal features describing the core regions of the ground truth contours can be calculated and an accepted range of values defined for each feature based on the minimum and maximum values calculated. The model criterion can be set to require that for any new contour the model sees, the values of all principal features in the core region must fall within the corresponding accepted range for that principal feature. Contours with any principal feature values outside of the corresponding accepted range are flagged for further review.

As another non-limiting example, within one cluster on the dendrogram, the feature with smallest variance was chosen and a total of six independent (or weakly correlated) features were chosen, which in this example were Entropy, Kurtosis, Skewness, Mean, Information Measure Correlation, and Homogeneous. For a given contour, the criterion for a "correct" core region can be selected such that at least 5 out of the 6 chosen features should be within a corresponding 95% statistical distribution range derived from ground truth contours. The statistical probability (P) for the ground truth contours passing these criteria would be, $$P = \sum_{n=5}^{6} B(6, n) \times 0.95^{6-n} \times 0.05^n = 0.967; \quad (8)$$

where the operator B denotes the binomial coefficient. This means the criteria can describe 96.7% of the texture patterns of specific organ. Contours that fail to meet these criteria (i.e., at least 2 out of 6 features being outside the 95% statistical distribution range) will be identified as inaccurate.

The second level 804 and the third level 806 of the example decision tree shown in FIG. 8 identify features that can best discern the organs-of-interest and surrounding tissues. To do this, multiple shell volumes can be generated for the ground truth contours and texture features can be calculated for each shell. As a non-limiting example, a paired T-test can be used to compare feature values of the inner with the outer shell of all ground truth contours in order to identify those features that have a significant difference in value (e.g., p<0.01). The feature with the largest absolute difference between the inner and outer shells can be selected for the decision tree model, ensuring that the chosen feature has the highest sensitivity to distinguish mislabeled surrounding tissues (e.g. fat, or different organs).

It follows that the criteria for passing the second level 804 and the third level 806 of the decision tree is that the difference between the texture feature value of the inner shell with the core should be smaller than a defined threshold value (second level 804) and the difference between the texture feature value of the outer shell with the core should be larger than a defined value (third level 806). The difference in texture feature value ATF can be defined as:

$$\Delta TF = \frac{TF_{shell} - TF_{core}}{TF_{core}}; \quad (9)$$

Figure 10A:
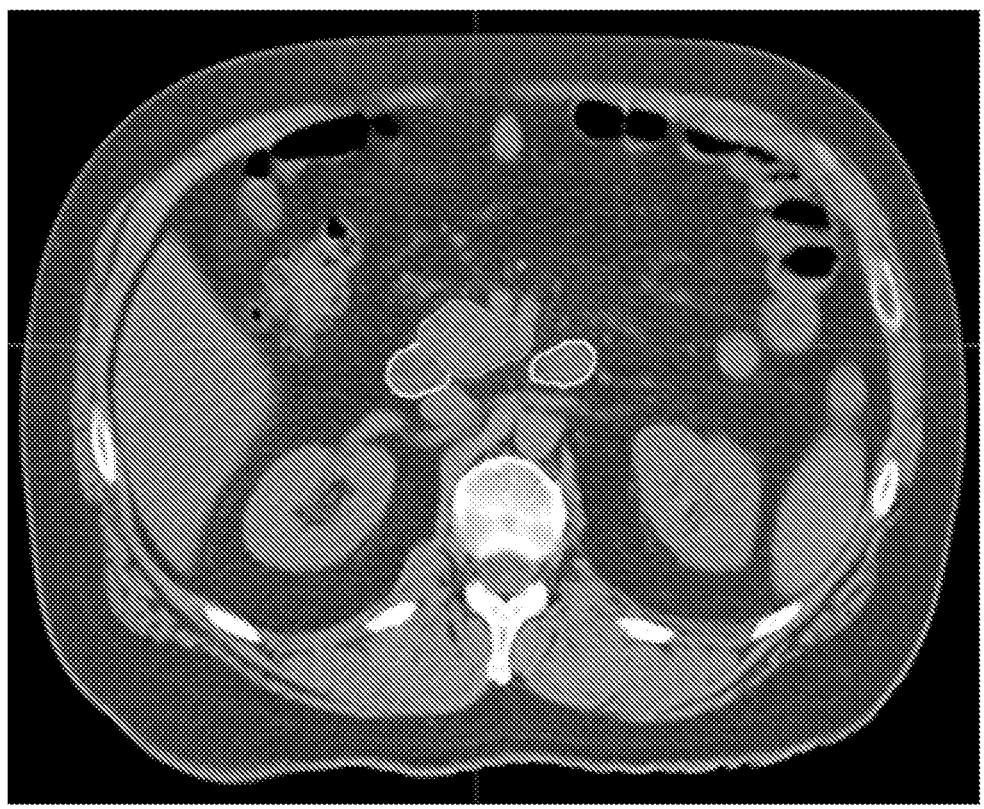
FIGS. 10A-10D show a representative case for texture feature selection.
Figure 10B:
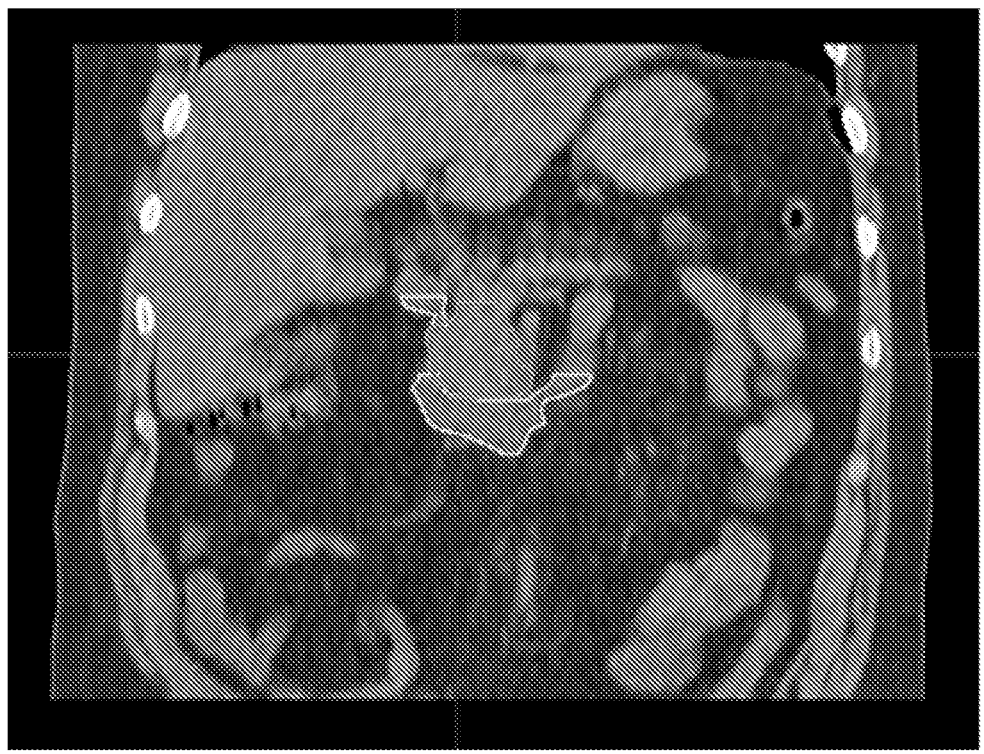
Figure 10C:
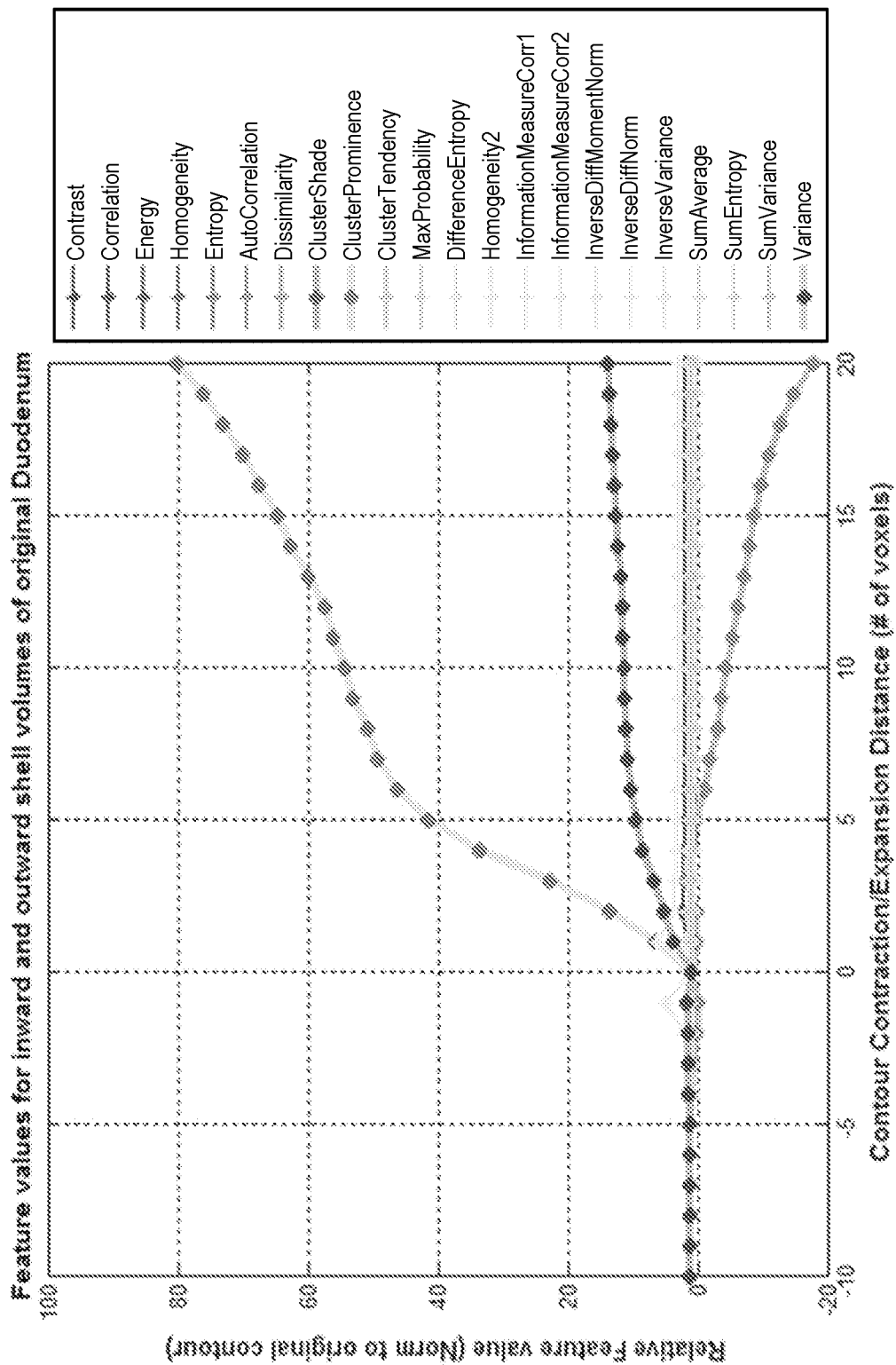
Figure 10D:
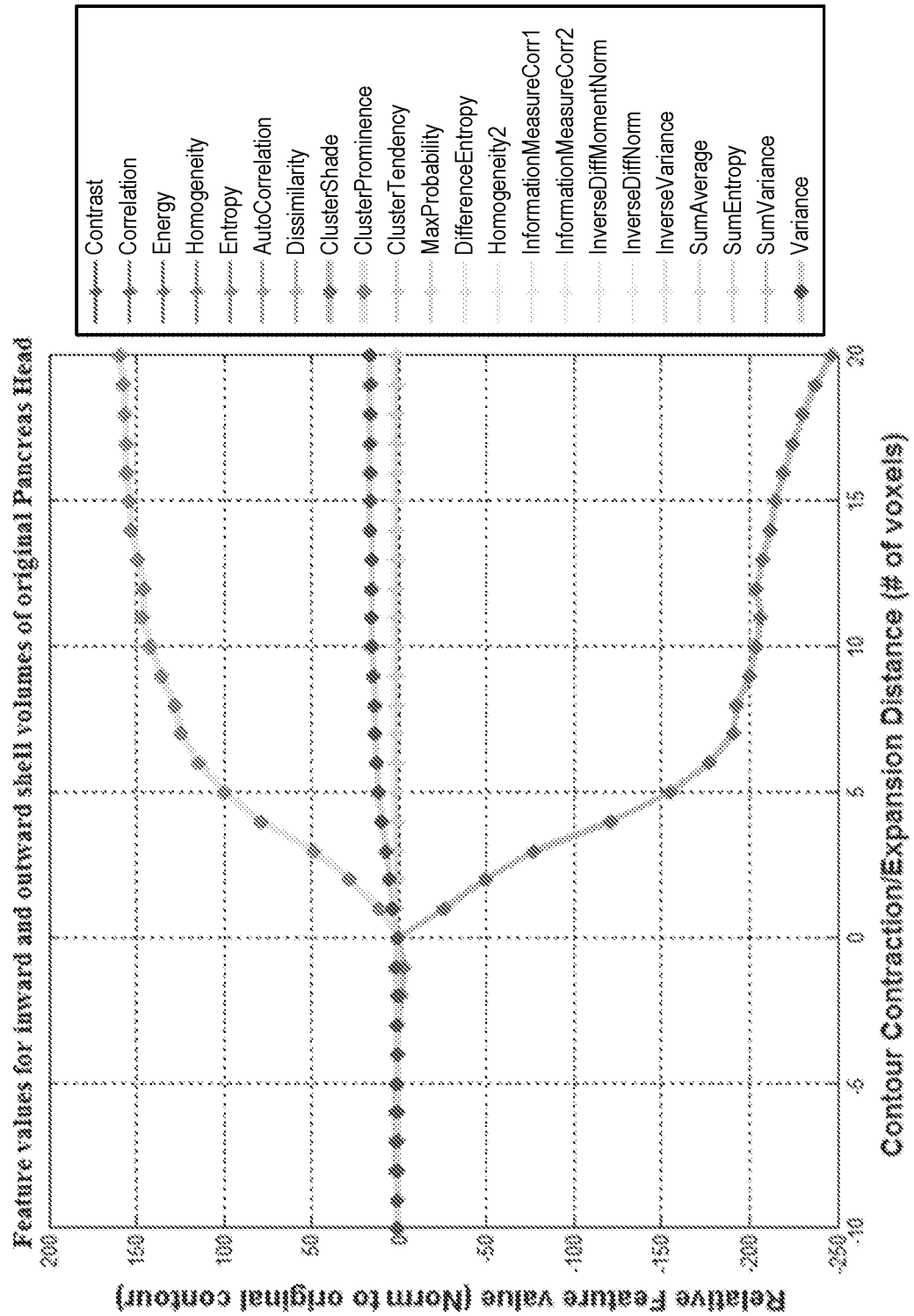

A representative testing case for texture feature selection is shown in FIGS. 10A-10D. For both pancreas head and duodenum contours, the shell volumes were contracted inward at intervals up to 10 mm, and expanded outward up to 20 mm. The X-axis of FIGS. 10C and 10D represents the interval of the expansion (positive) or contraction (negative) from original contours. All feature values were normalized to the one extracted from the original organ volume. For the inner shells, all the relative feature values are stable and close to 1. For outer shells, the GLCM-Cluster Prominence showed the most significant difference among all features. Even the 1 mm outer shell showed significant value variation compared with the initial organ volume.

The equation for GLCM-cluster prominence ("PCLP") calculation is shown above in Table 1. The GLCM-cluster prominence is the fourth power of the variation between the matrix values and the intensity weighted average value. Due to its mathematical characteristics, it is very sensitive to large deviant voxel pairs with high/low intensities, such as fat tissues around the pancreatic head. In some instances, the GLCM-cluster prominence can therefore be chosen as an appropriate feature for evaluating texture features in the inner and outer shells. For simplicity, the GLCM-cluster prominence for inner and outer shells can be referred to as InClusP and OutClusP, respectively.

Referring again to FIG. 7, parameters of the AI-based model are optimized, as indicated at step 718. For instance, ROC curve analysis can be employed to select optimal thresholds for the inner and outer shells. The ROC curve can be created by plotting the sensitivity against the (1-specificity) at various threshold settings of a selected texture feature, such as InClusP and OutClusP. The equations for Sensitivity and Specificity are as follows:

$$\text{Sensitivity} = \frac{TP}{TP + FN}; \quad (10)$$

$$\text{Specificity} = \frac{TN}{TN + FP}; \quad (11)$$

where TP, TN, FP, and FN are true positive, true negative, false positive, and false negative, respectively. Sensitivity is the ratio for a correct contour to be correctly identified as correct, while Specificity represents the ratio of an inaccurate contour to be correctly identified as inaccurate. To evaluate the model performance, False Negative Rate ("FNR"), False Positive Rate ("FPR") and Accuracy can also be calculated from the ROC curves, FNR=1−Sensitivity (12);

FPR=1−Specificity (13);

$$\text{Accuracy} = \frac{\text{Sensitivity} + \text{Specificity}}{2}. \quad (14)$$

After core region validation, ROC curves can be obtained to determine thresholds for each selected texture feature. A first ROC curve was generated by discretely increasing the threshold for the inner shell feature value from the minimum to the maximum value of the ground truth dataset. As the threshold increases, a greater number of accurate contours will be correctly identified (i.e. Sensitivity increases), and likewise, a greater number of inaccurate contours will be mislabeled (i.e. Specificity decreases). A peak can be observed in the plot of Accuracy (i.e. average of Sensitivity and Specificity) versus threshold value. This property can be used to automatically identify the optimal threshold, $T_{inner}$, which can be defined as the value of threshold for which Accuracy is maximum. With $T_{inner}$ fixed, the threshold for the outer shell can be incrementally increased, obtaining a second ROC curve. The optimal threshold, $T_{outer}$, can then be determined in the same way as for $T_{inner}$.

As another example, a first ROC curve can be generated by discretely increasing the threshold for the inner shell feature value. The optimal threshold can then be determined as the threshold value corresponding to the point with the highest achievable sensitivity and specificity of the test. The second ROC curve can be obtained by applying the pre-defined threshold and discretely increasing the threshold for the outer shell feature value. The optimal threshold for the outer shell feature value can be determined based on keeping specificity higher than a selected percentage (e.g., 90%, corresponding to a FPR smaller than 10%), and achieving a sensitivity as high as possible. The determined thresholds can then be used in the decision tree model to determine the accuracy of any new contours.

In the end, the model features are ready to be used for automatic contour quality assurance. At the contour evaluation stage 704, the identified clinically acceptable good contours can be used immediately for further re-planning and treatment, while reported inaccurate contours can be sent to physicians for manual modification, or corrected using the contour correction methods described in the present disclosure.

The above-described methods of using quantitative texture features to evaluate and validate quality of contour can rapidly identify accurate or inaccurate contours with high sensitivity and specificity. The methods can replace the time-consuming manual process of checking contours during online adaptation, facilitating the routine practice of OLAR.

Figure 11:
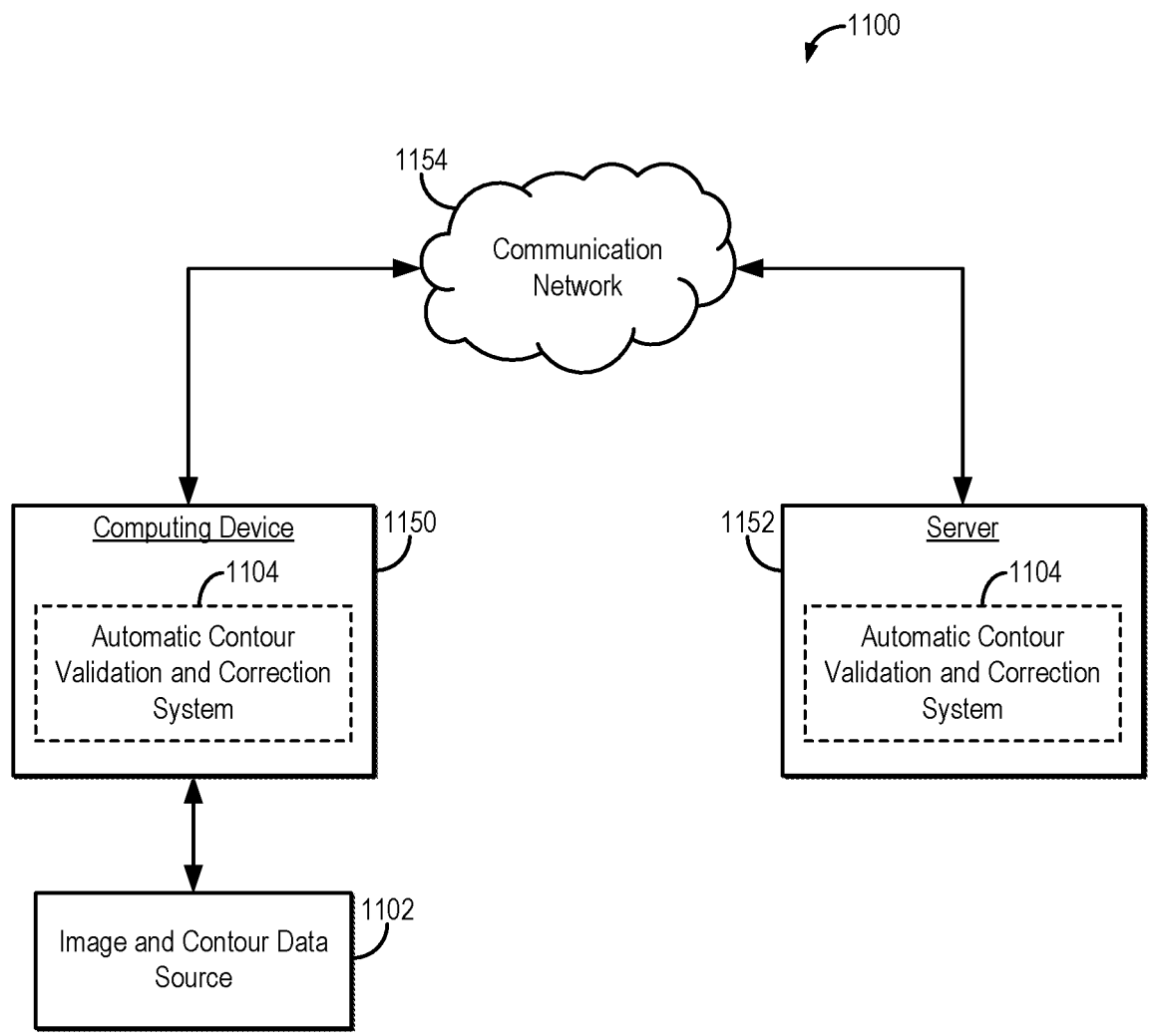
FIG. 11 is a block diagram of an example automatic contour correction and validation system that can implement embodiments described in the present disclosure.

Referring now to FIG. 11, an example of a system 1100 for automatic radiation treatment plan contour validation and correction in accordance with some embodiments of the systems and methods described in the present disclosure is shown. As shown in FIG. 11, a computing device 1150 can receive one or more types of data (e.g., image data, contour data) from image and contour data source 1102, which may include a source of CT images, magnetic resonance images, other medical images, or combinations thereof, and contours generated from such images. In some embodiments, computing device 1150 can execute at least a portion of an automatic contour validation and correction system 1104 to automatically validate contours, automatically correct contours, or both, based on data received from the image and contour data source 1102.

Additionally or alternatively, in some embodiments, the computing device 1150 can communicate information about data received from the image and contour data source 1102 to a server 1152 over a communication network 1154, which can execute at least a portion of the automatic contour validation and correction system 1104. In such embodiments, the server 1152 can return information to the computing device 1150 (and/or any other suitable computing device) indicative of an output of the automatic contour validation and correction system 1104.

In some embodiments, computing device 1150 and/or server 1152 can be any suitable computing device or combination of devices, such as a desktop computer, a laptop computer, a smartphone, a tablet computer, a wearable computer, a server computer, a virtual machine being executed by a physical computing device, and so on. The computing device 1150 and/or server 1152 can also reconstruct images from the data.

In some embodiments, image and contour data source 1102 can be any suitable source of image data (e.g., measurement data, images reconstructed from measurement data), such as a CT system, and MRI system, another computing device (e.g., a server storing image data), and so on. In some embodiments, image and contour data source 1102 can be local to computing device 1150. For example, image and contour data source 1102 can be incorporated with computing device 1150 (e.g., computing device 1150 can be configured as part of a device for capturing, scanning, and/or storing images). As another example, image and contour data source 1102 can be connected to computing device 1150 by a cable, a direct wireless link, and so on. Additionally or alternatively, in some embodiments, image and contour data source 1102 can be located locally and/or remotely from computing device 1150, and can communicate data to computing device 1150 (and/or server 1152) via a communication network (e.g., communication network 1154).

In some embodiments, communication network 1154 can be any suitable communication network or combination of communication networks. For example, communication network 1154 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 11 can each be any suitable communications link or combination of communications links, such as wired links, fiber optic links, Wi-Fi links, Bluetooth links, cellular links, and so on.

Figure 12:
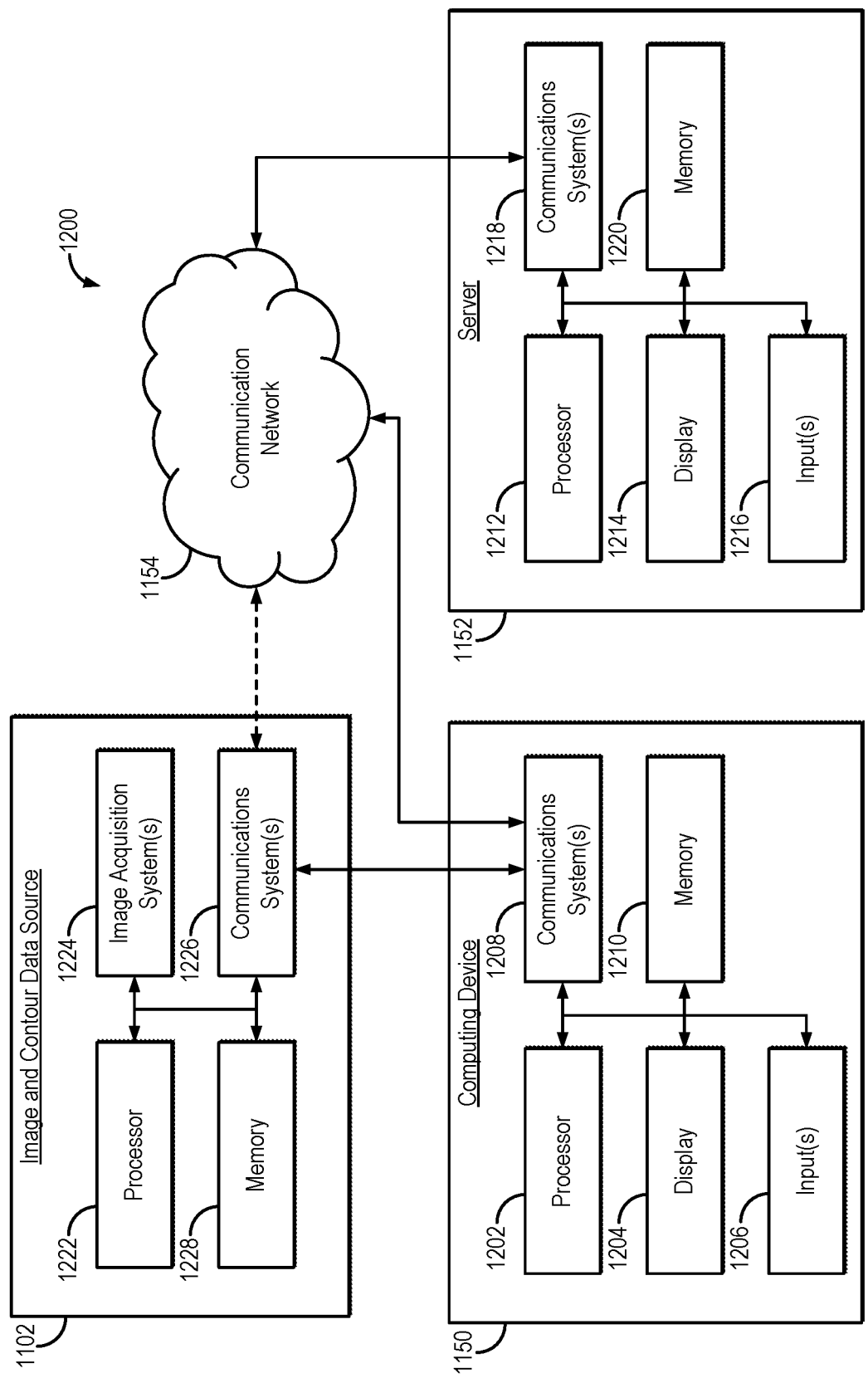
FIG. 12 is a block diagram of example components that can implement the automatic contour correction and validation system of FIG. 11.

Referring now to FIG. 12, an example of hardware 1200 that can be used to implement image and contour data source 1102, computing device 1150, and server 1154 in accordance with some embodiments of the systems and methods described in the present disclosure is shown. As shown in FIG. 12, in some embodiments, computing device 1150 can include a processor 1202, a display 1204, one or more inputs 1206, one or more communication systems 1208, and/or memory 1210. In some embodiments, processor 1202 can be any suitable hardware processor or combination of processors, such as a central processing unit ("CPU"), a graphics processing unit ("GPU"), and so on. In some embodiments, display 1204 can include any suitable display devices, such as a computer monitor, a touchscreen, a television, and so on. In some embodiments, inputs 1206 can include any suitable input devices and/or sensors that can be used to receive user input, such as a keyboard, a mouse, a touchscreen, a microphone, and so on.

In some embodiments, communications systems 1208 can include any suitable hardware, firmware, and/or software for communicating information over communication network 1154 and/or any other suitable communication networks. For example, communications systems 1208 can include one or more transceivers, one or more communication chips and/or chip sets, and so on. In a more particular example, communications systems 1208 can include hardware, firmware and/or software that can be used to establish a Wi-Fi connection, a Bluetooth connection, a cellular connection, an Ethernet connection, and so on.

In some embodiments, memory 1210 can include any suitable storage device or devices that can be used to store instructions, values, data, or the like, that can be used, for example, by processor 1202 to present content using display 1204, to communicate with server 1152 via communications system(s) 1208, and so on. Memory 1210 can include any suitable volatile memory, non-volatile memory, storage, or any suitable combination thereof. For example, memory 1210 can include RAM, ROM, EEPROM, one or more flash drives, one or more hard disks, one or more solid state drives, one or more optical drives, and so on. In some embodiments, memory 1210 can have encoded thereon, or otherwise stored therein, a computer program for controlling operation of computing device 1150. In such embodiments, processor 1202 can execute at least a portion of the computer program to present content (e.g., images, user interfaces, graphics, tables), receive content from server 1152, transmit information to server 1152, and so on.

In some embodiments, server 1152 can include a processor 1212, a display 1214, one or more inputs 1216, one or more communications systems 1218, and/or memory 1220. In some embodiments, processor 1212 can be any suitable hardware processor or combination of processors, such as a CPU, a GPU, and so on. In some embodiments, display 1214 can include any suitable display devices, such as a computer monitor, a touchscreen, a television, and so on. In some embodiments, inputs 1216 can include any suitable input devices and/or sensors that can be used to receive user input, such as a keyboard, a mouse, a touchscreen, a microphone, and so on.

In some embodiments, communications systems 1218 can include any suitable hardware, firmware, and/or software for communicating information over communication network 1154 and/or any other suitable communication networks. For example, communications systems 1218 can include one or more transceivers, one or more communication chips and/or chip sets, and so on. In a more particular example, communications systems 1218 can include hardware, firmware and/or software that can be used to establish a Wi-Fi connection, a Bluetooth connection, a cellular connection, an Ethernet connection, and so on.

In some embodiments, memory 1220 can include any suitable storage device or devices that can be used to store instructions, values, data, or the like, that can be used, for example, by processor 1212 to present content using display 1214, to communicate with one or more computing devices 1150, and so on. Memory 1220 can include any suitable volatile memory, non-volatile memory, storage, or any suitable combination thereof. For example, memory 1220 can include RAM, ROM, EEPROM, one or more flash drives, one or more hard disks, one or more solid state drives, one or more optical drives, and so on. In some embodiments, memory 1220 can have encoded thereon a server program for controlling operation of server 1152. In such embodiments, processor 1212 can execute at least a portion of the server program to transmit information and/or content (e.g., data, images, a user interface) to one or more computing devices 1150, receive information and/or content from one or more computing devices 1150, receive instructions from one or more devices (e.g., a personal computer, a laptop computer, a tablet computer, a smartphone), and so on.

In some embodiments, image and contour data source 1102 can include a processor 1222, one or more image acquisition systems 1224, one or more communications systems 1226, and/or memory 1228. In some embodiments, processor 1222 can be any suitable hardware processor or combination of processors, such as a CPU, a GPU, and so on. In some embodiments, the one or more image acquisition systems 1224 are generally configured to acquire data, images, or both, and can include a CT system, and MRI system, or both. Additionally or alternatively, in some embodiments, one or more image acquisition systems 1224 can include any suitable hardware, firmware, and/or software for coupling to and/or controlling operations of a CT system, and MRI system, or both. In some embodiments, one or more portions of the one or more image acquisition systems 1224 can be removable and/or replaceable.

Note that, although not shown, image and contour data source 1102 can include any suitable inputs and/or outputs. For example, image and contour data source 1102 can include input devices and/or sensors that can be used to receive user input, such as a keyboard, a mouse, a touchscreen, a microphone, a trackpad, a trackball, and so on. As another example, image and contour data source 1102 can include any suitable display devices, such as a computer monitor, a touchscreen, a television, etc., one or more speakers, and so on.

In some embodiments, communications systems 1226 can include any suitable hardware, firmware, and/or software for communicating information to computing device 1150 (and, in some embodiments, over communication network 1154 and/or any other suitable communication networks). For example, communications systems 1226 can include one or more transceivers, one or more communication chips and/or chip sets, and so on. In a more particular example, communications systems 1226 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 1228 can include any suitable storage device or devices that can be used to store instructions, values, data, or the like, that can be used, for example, by processor 1222 to control the one or more image acquisition systems 1224, and/or receive data from the one or more image acquisition systems 1224; to images from data; present content (e.g., images, a user interface) using a display; communicate with one or more computing devices 1150; and so on. Memory 1228 can include any suitable volatile memory, non-volatile memory, storage, or any suitable combination thereof. For example, memory 1228 can include RAM, ROM, EEPROM, one or more flash drives, one or more hard disks, one or more solid state drives, one or more optical drives, and so on. In some embodiments, memory 1228 can have encoded thereon, or otherwise stored therein, a program for controlling operation of image source 1102. In such embodiments, processor 1222 can execute at least a portion of the program to generate images, transmit information and/or content (e.g., data, images) to one or more computing devices 1150, receive information and/or content from one or more computing devices 1150, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

As mentioned above, the currently available methods of plan-quality evaluation by visual or automated examination of dose-volume metrics and visual inspection of 3D dose distribution can be time-consuming for OLAR. The conventional plan evaluation based on dose metrics from wish list and dose-volume histogram ("DVH") lacks spatial information; thus, physicians have to check the dose distribution slice-by-slice to conclude the plan quality with subjective decision. The systems and methods described in the present disclosure implement metrics (e.g., DVH metrics) and texture features based on dose spatial distributions to setup an objective method for plan quality auto-evaluation.

In general, the methods described in the present disclosure include calculating a number of texture features and metrics (e.g., DVH metrics) from each 3D dose distribution to be compared. Four categories of features calculated from the spatial dose distribution can be used in the methods described in the present disclosure. These features include dose level size zone matrix ("DLSZM") to emphasize large contiguous regions; dose level co-occurrence matrix ("DLCM"), which defines the dose level relationship between same spatial voxel of two plans; mutual objective function distance ("MOFD"), which evaluates the distance of plan dose distribution to the goal dose distribution in the treatment planning system; and neighbor level-dose difference matrix, which resembles the human perception of the image to indicate the local dose change. As one example, other metrics can be calculated from these features, including large cold spot ("LCS"), which can be calculated from the DLSZM, and hot contrast ("HC"), which can be calculated from the DLCM, and which evaluates hotness of one plan to another plan at the same spatial voxel. The superior, or otherwise optimal, plan is determined from the set of compared plans based on the differences of these metrics and features between the plans to be compared.

Online ART provides for optimal treatment dose delivery with inter-fractional change of organs. Compared to IGRT repositioning, OLAR provides superior adaptive plans by improving target coverage and/or OAR sparing. With current technology, OLAR is implemented with human interaction during the whole workflow. One part of these human operations is the plan evaluation. In the OLAR workflow, there are generally two plans from which the physician selects the superior plan. The first plan is the adaptive plan, which is a plan adjusted with or without full optimization on daily anatomical changes. The second plan is a repositioning plan, which is a recalculation of the reference plan based on the registration between the reference image and the daily image. The physician selects the superior plan to achieve the best dose benefit on daily fractions of the treatment.

Treatment plan evaluation is a clinically subjective decision-making problem that involves visual search and analysis in a contextually rich environment, including delineated structures and isodose lines superposed on CT data. This labor-intensive task is usually performed by oncologists and physicists, and is limited by the experience, skill, and capabilities of the oncologist or physicist.

Similar to a three-dimensional image, the dose level of each voxel resembles the intensity of each voxel in a spatial dose distribution, such as a dose map, which may be a 2D or 3D dose map. The dose texture features of a dose map can be defined and computed similar to that from an image.

As an example of a texture feature or metric that can be computed from a spatial distribution of dose, such as a 3D dose map, LCS can be computed as, $$LCS = \frac{1}{S^2} \cdot \frac{\sum_{i=1}^{N}\sum_{z=1}^{S} M(i,z)(i-N)^2 z^2}{\sum_{i=1}^{N}\sum_{z=1}^{S} M(i,z)}; \quad (15)$$

where M(i,z) is an N×S matrix having elements that are the frequency of contiguous voxels of size, z, and dose level, i.

As another example of a texture feature or metric that can be computed from a spatial distribution of dose, such as a 3D dose map, HC can be computed from the DLCM. The DLCM for a first plan ("plan 1") and a second plan ("plan 2") is, $$p(i,j) = \frac{F(i,j)}{\sum_{i,j}^{N} F(i,j)}; \quad (16)$$

where F(i,j) is an N×N matrix having elements that are the frequency of a first dose level, i, at the first plan and the frequency of a second dose level, j, at the second plan at the same voxel. The hot contrast for the first and second plan is, $$HC_{1\to 2} = \sum_{i=0}^{N-1}\sum_{j=0}^{i}(i-j)^2 p(i,j), \text{ for } i \in \text{plan 1 and } j \in \text{plan 2.} \quad (17)$$

As another example of a texture feature or metric that can be computed from a spatial distribution of dose, such as a 3D dose map, inverse covariance ("IC") can be computed as, $$IC_{1\to 2} \sum_{i=0}^{N-1}\sum_{j=0}^{i} \frac{p(i,j)}{(1+(i-j)^2)}, \text{ for } i \in \text{plan 1 and } j \in \text{plan 2.} \quad (18)$$

As another example of a texture feature or metric that can be computed from a spatial distribution of dose, such as a 3D dose map, the neighbor level dose difference matrix ("NLDDM") can be calculated based on defining the local difference between each voxel and their neighbor average, $$S_i = \left\| \sum_{i=0}^{N} i - \sum_{j}^{Z} D_j \right\|; \quad (19)$$

where Z is the set of all neighbors of dose level i voxel, and where $p_j$ is the probability of dose level, j.

As another example of a texture feature or metric that can be computed from a spatial distribution of dose, such as a 3D dose map, coarseness ("Co") can be defined as, $$Co = 1 \bigg/ \left( \varepsilon + \frac{\sum_{k=0}^{N-1} p_k S_k}{\sum_{k=0}^{n-1} p_k} \right). \quad (20)$$

As another example of a texture feature or metric that can be computed from a spatial distribution of dose, such as a 3D dose map, busyness ("Bu") can be defined as, $$Bu = \frac{\sum_{k=0}^{n-1} p_k}{\sum_{i=0}^{N-1}\sum_{j=0}^{i} \|ip_i - jp_j\|}. \quad (21)$$

As another example of a texture feature or metric that can be computed from a spatial distribution of dose, such as a 3D dose map, MOFD can be computed as follows. First, an objective function distance for a target is defined. For prescription dose greater than the goal dose (i.e., $p_j > g_j$), the objective function distance can be computed as, $$F_T(d) = \begin{cases} \beta_1 \sum_j (g_j - d_j)^2 + \beta_2 \sum_j (p_j - d_j)^2 & \text{for } g_j > d_j \\ \beta_2 \sum_j (p_j - d_j)^2 & \text{for } g_j \le d_j < p_j \\ \beta_3 \sum_j (p_j - d_j)^2 & \text{for } d_j \ge p_j \end{cases} \quad (22)$$

For prescription dose less than the goal dose (i.e., $p_j < g_j$), the objective function distance can be computed as, $$F_T(d) = \begin{cases} \beta_5 \sum_j (d_j - p_j)^2 + \beta_6 \sum_j (d_j - p_j)^2 & \text{for } d_j > g_j \\ \beta_5 \sum_j (d_j - p_j)^2 & \text{for } p_j \le d_j < g_j \\ \beta_4 \sum_j (d_j - p_j)^2 & \text{for } p_j \ge d_j \end{cases} \quad (23)$$

Next, an objective function for OARs in a first plan (e.g., an adaptive plan "A") and a second plan (e.g., a repositioning plan "R") can be defined as, $$MF_{OAR}^{A\to R}(d) = \begin{cases} \gamma \sum_j (R_j - A_j)^2 & \text{for } A_j > R_j \\ 0 & \text{for } A_j \le R_j \end{cases} \quad (24)$$

The parameters $\beta_1$-$\beta_6$ can be heuristically determined in the treatment planning system. The MOFD for the first and second plans can then be defined as, $$MOFD_{1\to 2} = \sum_k F_{1T}(d) - \sum_k F_{2T}(d) + \sum_s MF_{OAR}^{1\to 2}(d); \quad (25)$$

where k and s are the number of target and OAR.

Based on the texture features and metrics described above, and other texture features or metrics computed from a spatial distribution of dose (e.g., a 3D dose map), plan quality can be evaluated. To assist in this process, a general quality index ("GQI") can be defined as a quantitative metric for evaluating clinical decisions for a treatment plan:

$$GQI = \alpha_1 HC_{>2} + \alpha_2 IC_{1\to 2} + \alpha_3 LCS + \alpha_4 Co + \alpha_5 Bu + \alpha_6 MOFD_{1\to 2} \quad (26);$$

All coefficients can be determined from a ground truth dataset so that the plan with the lower GQI has the superior plan quality.

In some implementations, a machine learning algorithm implemented with a hardware processor and a memory can be used to evaluate radiation treatment plan quality based on one or more texture feature or metric computed from a 3D dose map. As one example, a boosted decision tree algorithm with a hyper-parameter optimization can be implemented to determine optimal dose texture features and the ranges of those feature values that can be used to identify a better quality plan between competing plans. In such implementations, a number of dose texture features obtained from sets of different radiation treatment plan types (e.g., adaptive plans, repositioning plans) can be initially used as predictive variables, along with more commonly used dose-volume parameters. Initial classifiers, including complex trees, discriminant analysis, support vector machines, logistic regression, nearest neighbors, ensemble classification, boosted decision trees, or combinations thereof, can be trained with all dose texture features and cross-validation (e.g., leave-one-out cross-validation).

Figure 13:
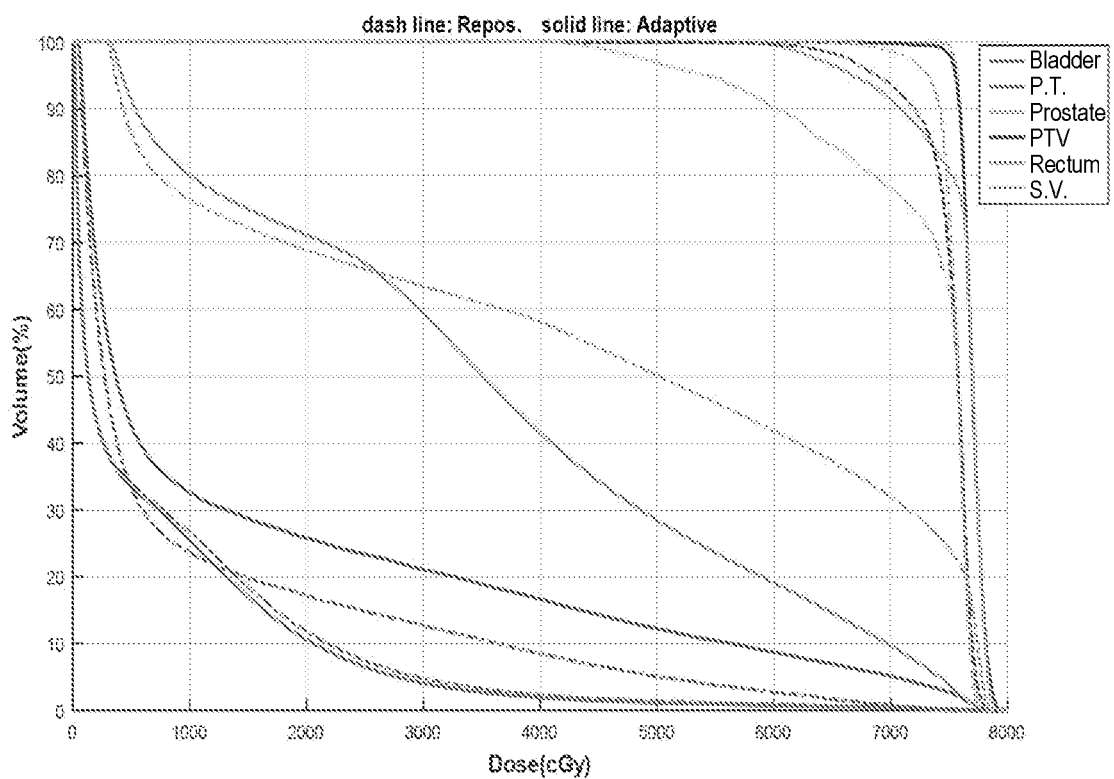
FIG. 13 shows a dose volume histogram ("DVH") comparison between an example adaptive plan and an example repositioning plan.
Figure 14:
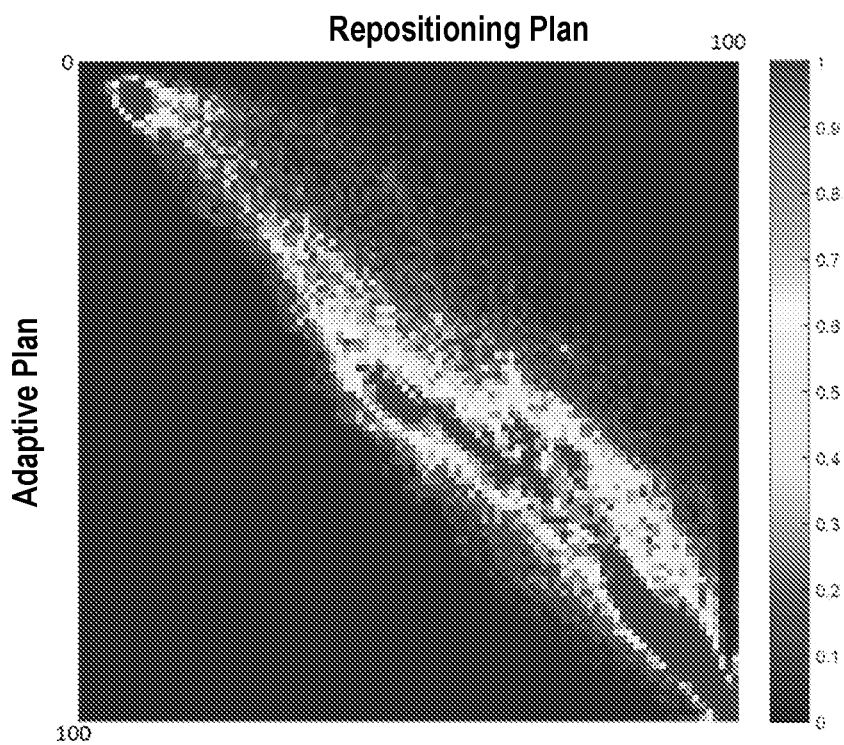
FIG. 14 shows a dose level co-occurrence matrix ("DLCM") hot contrast map of the example adaptive plan and the example repositioning plan.
Figure 15:
FIG. 15 shows a dose level size zone matrix ("DLSZM") map of a planning target volume ("PTV") in the example adaptive plan and the example repositioning plan.
Figure 15:

In an example study, planning and daily CTs were acquired during RT using a CT-on-Rails for prostate cancer patients. In this study, 11 fraction daily images were randomly selected in five patients. For each daily CT set, both IGRT repositioning and adaptive plans were generated. Daily contours were created and edited based on daily CT. The repositioning plans were recalculated from reference plan based on new structures positions. FIG. 13 shows an example of a dose volume histogram ("DVH") of two plans (adaptive and repositioning). FIG. 14 shows the DLCM of all OARs of these two plans. The co-occurrence frequency existed mostly in the upper right part, indicating that the repositioning plan had higher dose than the adaptive plan at the same position of the OARs. FIG. 15 shows a DLSZM of the planning target volume ("PTV") in the adaptive plan and the repositioning plan.

Each metric has its own physical meaning connected to plan quality. The LCS is an index that shows large connected regions with low doses. The larger LCS values indicate more, or larger, low dose connected regions in the structure. In PTV, a large LCS value will be related to inferior quality of the plan.

HC and IC show the accumulated difference in the same position of two different plans. The larger values indicate a plan is generally hotter than other plans in the same voxel. In OARs, this value indicates a lower quality plan. Due to direct comparison with the same position, there is no ambiguous interpretation of hotness of structures in a plan.

Coarseness and busyness indicate the local dose level change, and give a similar perception of human vision on an image. High values are correspondent to a coarser image in the vision. For the dose distribution, this can be interpreted as more island-like spatial distribution with inferior plan quality.

MOFD indicated a difficulty of plan evaluation when the quality of plan is varied in the space. If the quality of a first plan (e.g., "plan A") in a first location (e.g., "location 1") is superior to a second plan (e.g., "plan B"), but inferior in a second location (e.g., "location 2"), the MOFD can give an absolute quality value by measuring the distance between plan and optimal dose distribution.

The GQI provides a general index of plan quality. The GQI can be calculated from the GQI formula in Eqn. (26) with empirical coefficients. With regression analysis, accurate coefficients can be extracted from a ground truth dataset.

Figure 16:
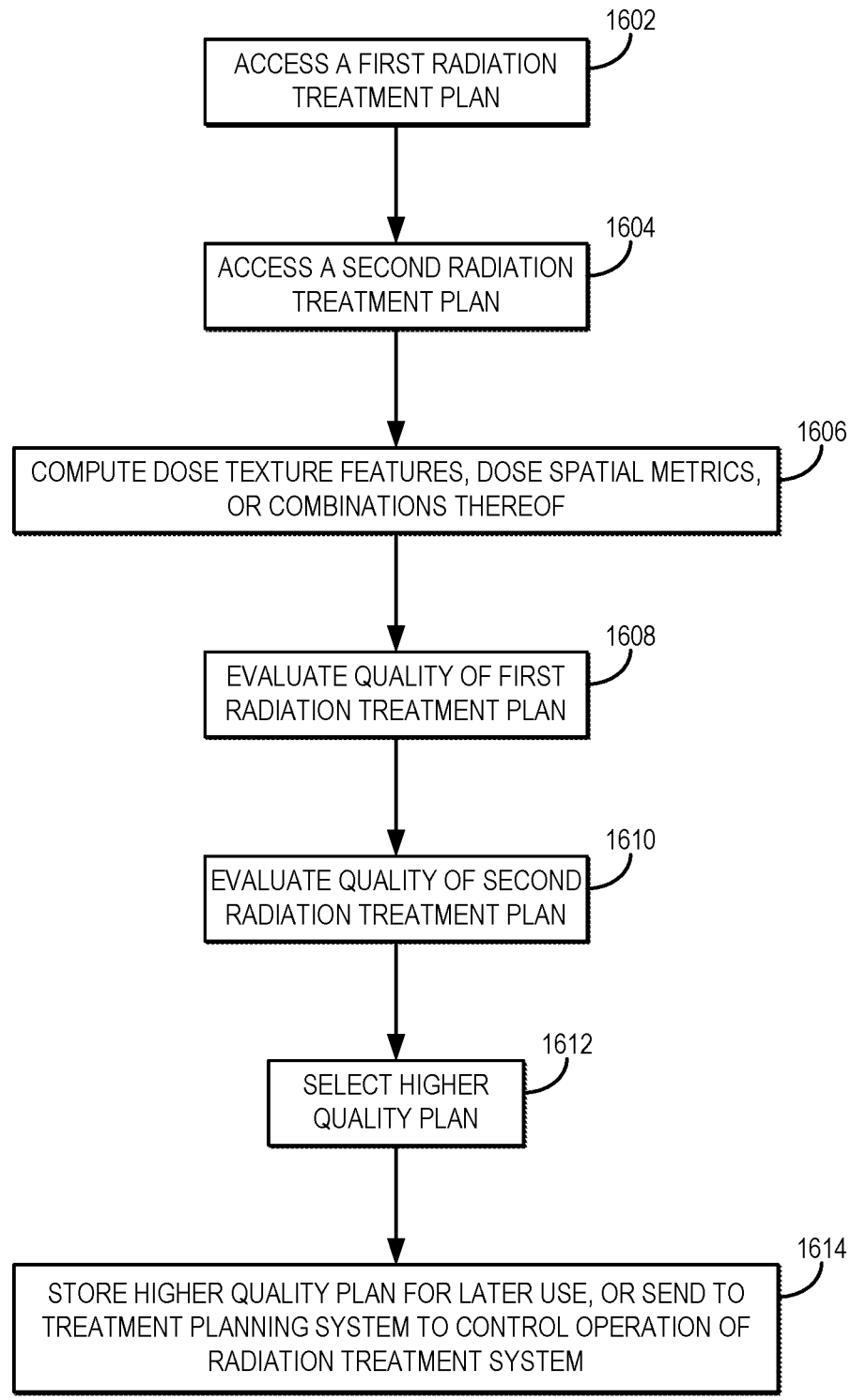
FIG. 16 is a flowchart of an example method for evaluating radiation treatment plan quality based on dose texture features, spatial dose metrics, or combinations thereof.

Referring now to FIG. 16, a flowchart is illustrated as setting forth the steps of an example method for evaluating the quality of different available radiation treatment plans based computing and comparing texture features, metrics, or both from spatial dose distributions associated with the plans. The method includes accessing a first radiation treatment plan with a computer system, as indicated at step 1602. A second radiation treatment plan is also accessed with the computer system, as indicated at step 1604. Accessing the radiation treatment plans can include, for instance, retrieving previously generated radiation treatment plans from a memory or other data storage.

One or more texture features, metrics, or both are then computed from spatial dose distributions contained in the first and second radiation treatment plans, as indicated generally at step 1606. As noted above, the texture features, metrics, or both, can include DLSZM-LCS, DLCM-HC, DLCM-IC, NLDDM-Co, MOFD, GQI, combinations thereof, or other texture features or metrics. The computed texture features, metrics, or both, are then analyzed to evaluate the quality of the first and second plans; thus, a quality of the first plan is evaluated at step 1608 and the quality of the second plan is evaluated at step 1610. In some implementations, the quality of both plans may be evaluated simultaneously.

Based on this evaluation, the plan with the higher quality is selected, as indicated at step 1612, and is stored for later use or provided to a radiation treatment planning system to control the operation of a radiation treatment system, as indicated at step 1614.

Methods of using dose texture metrics extracted from spatial dose distribution to automatically and objectively evaluate dosimetric plan quality have thus been described. Optimal dose texture features may be determined based on a machine learning algorithm. This dose texture based plan evaluation method can be implemented for OLAR to significantly reduce the time for plan evaluation.

Figure 17:
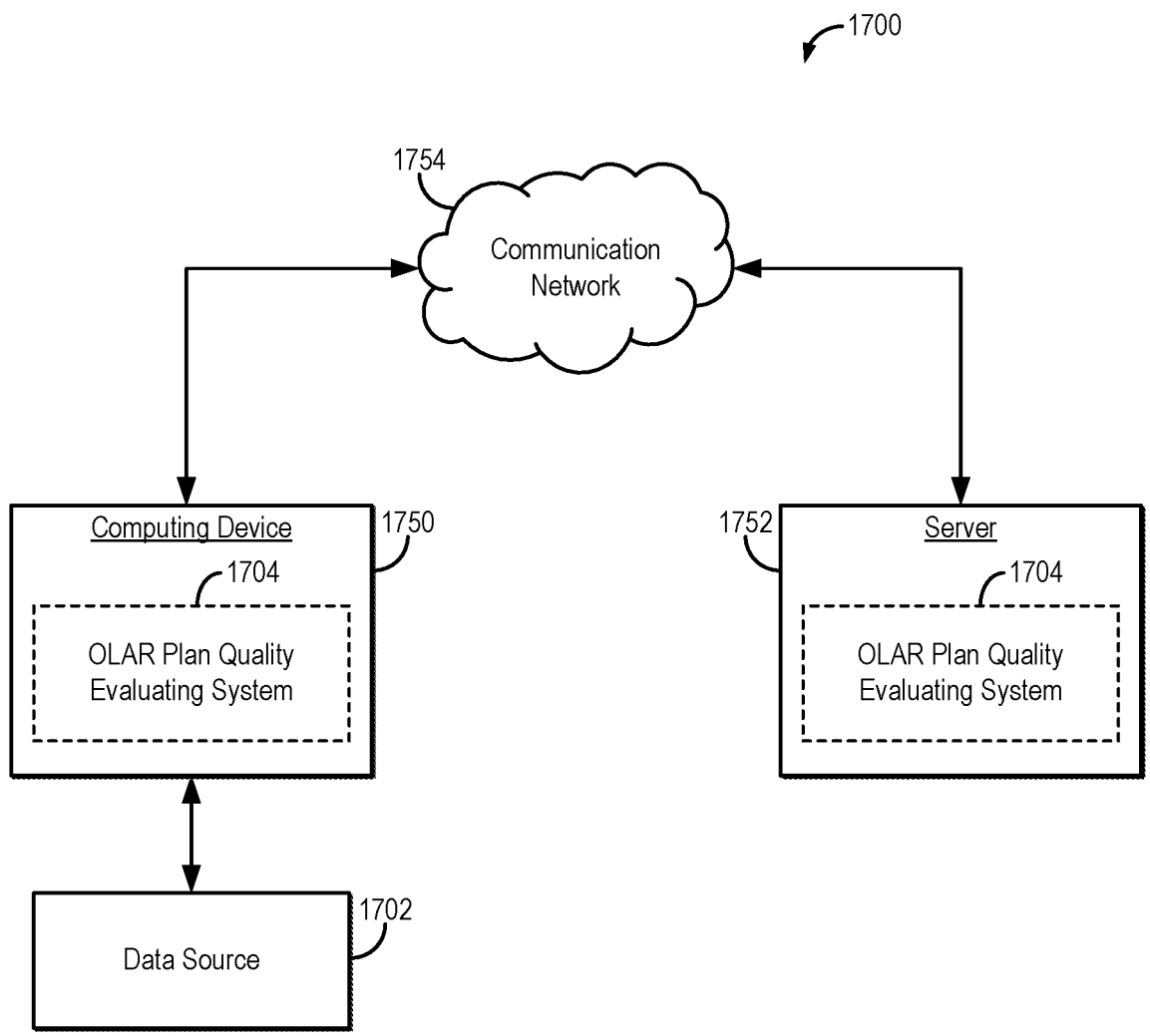
FIG. 17 is a block diagram of an example automatic OLAR plan quality evaluating system that can implement embodiments described in the present disclosure.

Referring now to FIG. 17, an example of a system 1700 for automatically evaluating an OLAR plan quality in accordance with some embodiments of the systems and methods described in the present disclosure is shown. As shown in FIG. 17, a computing device 1750 can receive one or more types of data (e.g., radiation treatment plan data, image data) from data source 1702, which may be a radiation treatment plan data source. In some embodiments, computing device 1750 can execute at least a portion of an OLAR plan quality evaluating system 1704 to automatically evaluate an OLR plan quality from data received from the data source 1702.

Additionally or alternatively, in some embodiments, the computing device 1750 can communicate information about data received from the data source 1702 to a server 1752 over a communication network 1754, which can execute at least a portion of the OLAR plan quality evaluating system 1704. In such embodiments, the server 1752 can return information to the computing device 1750 (and/or any other suitable computing device) indicative of an output of the OLAR plan quality evaluating system 1704.

In some embodiments, computing device 1750 and/or server 1752 can be any suitable computing device or combination of devices, such as a desktop computer, a laptop computer, a smartphone, a tablet computer, a wearable computer, a server computer, a virtual machine being executed by a physical computing device, and so on. The computing device 1750 and/or server 1752 can also reconstruct images from the data.

In some embodiments, data source 1702 can be any suitable source of radiation treatment plan data; image data (e.g., measurement data, images reconstructed from measurement data), such as a CT system, MRI system, or both; another computing device (e.g., a server storing radiation treatment plan data and/or image data); and so on. In some embodiments, data source 1702 can be local to computing device 1750. For example, data source 1702 can be incorporated with computing device 1750 (e.g., computing device 1750 can be configured as part of a device for capturing, scanning, and/or storing images). As another example, data source 1702 can be connected to computing device 1750 by a cable, a direct wireless link, and so on. Additionally or alternatively, in some embodiments, data source 1702 can be located locally and/or remotely from computing device 1750, and can communicate data to computing device 1750 (and/or server 1752) via a communication network (e.g., communication network 1754).

In some embodiments, communication network 1754 can be any suitable communication network or combination of communication networks. For example, communication network 1754 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 17 can each be any suitable communications link or combination of communications links, such as wired links, fiber optic links, Wi-Fi links, Bluetooth links, cellular links, and so on.

Figure 18:
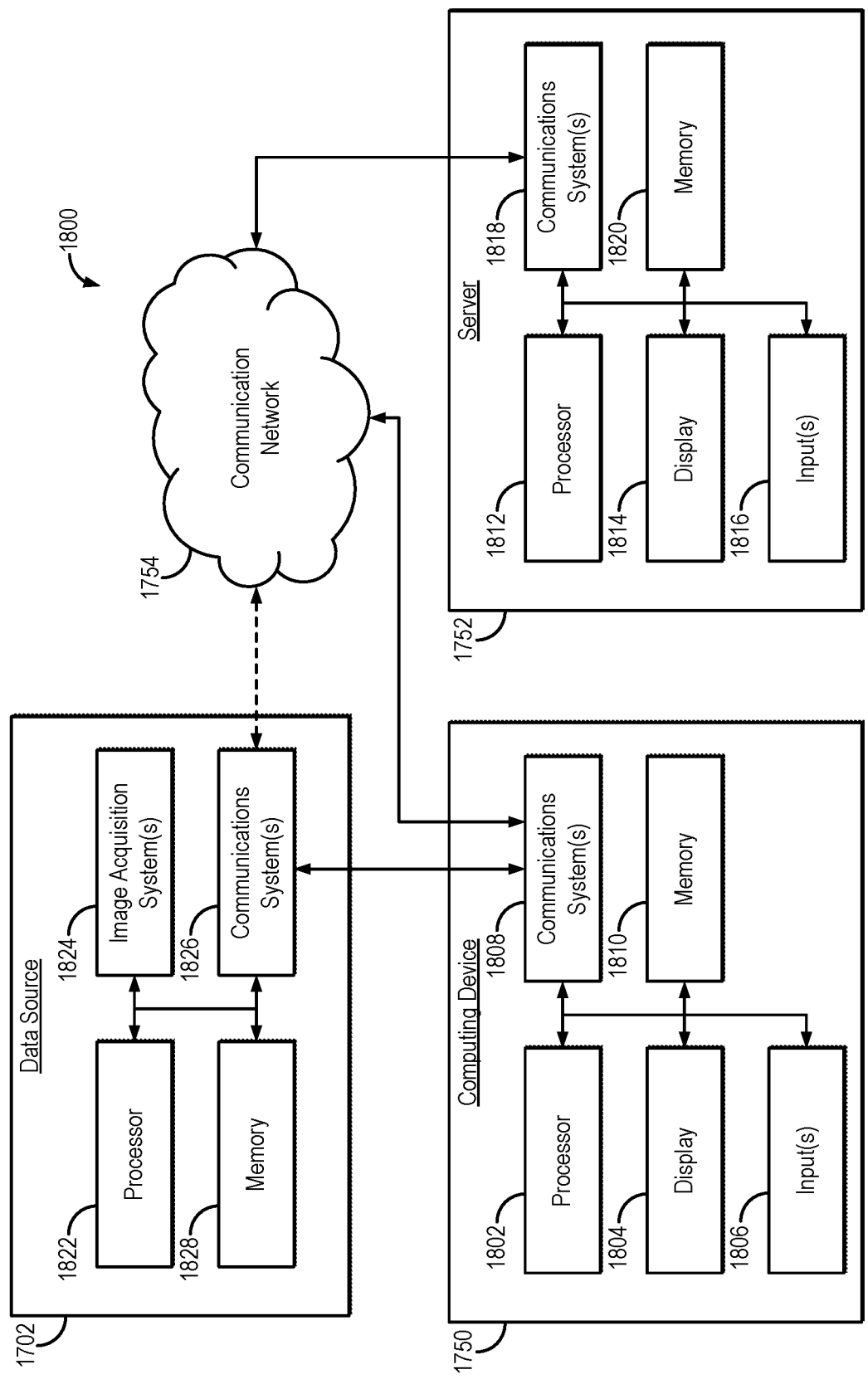
FIG. 18 is a block diagram of example components that can implement the automatic OLAR plan quality evaluating system of FIG. 17.

Referring now to FIG. 18, an example of hardware 1800 that can be used to implement image source 1702, computing device 1750, and server 1754 in accordance with some embodiments of the systems and methods described in the present disclosure is shown. As shown in FIG. 18, in some embodiments, computing device 1750 can include a processor 1802, a display 1804, one or more inputs 1806, one or more communication systems 1808, and/or memory 1810. In some embodiments, processor 1802 can be any suitable hardware processor or combination of processors, such as a central processing unit ("CPU"), a graphics processing unit ("GPU"), and so on. In some embodiments, display 1804 can include any suitable display devices, such as a computer monitor, a touchscreen, a television, and so on. In some embodiments, inputs 1806 can include any suitable input devices and/or sensors that can be used to receive user input, such as a keyboard, a mouse, a touchscreen, a microphone, and so on.

In some embodiments, communications systems 1808 can include any suitable hardware, firmware, and/or software for communicating information over communication network 1754 and/or any other suitable communication networks. For example, communications systems 1808 can include one or more transceivers, one or more communication chips and/or chip sets, and so on. In a more particular example, communications systems 1808 can include hardware, firmware and/or software that can be used to establish a Wi-Fi connection, a Bluetooth connection, a cellular connection, an Ethernet connection, and so on.

In some embodiments, memory 1810 can include any suitable storage device or devices that can be used to store instructions, values, data, or the like, that can be used, for example, by processor 1802 to present content using display 1804, to communicate with server 1752 via communications system(s) 1808, and so on. Memory 1810 can include any suitable volatile memory, non-volatile memory, storage, or any suitable combination thereof. For example, memory 1810 can include RAM, ROM, EEPROM, one or more flash drives, one or more hard disks, one or more solid state drives, one or more optical drives, and so on. In some embodiments, memory 1810 can have encoded thereon, or otherwise stored therein, a computer program for controlling operation of computing device 1750. In such embodiments, processor 1802 can execute at least a portion of the computer program to present content (e.g., images, user interfaces, graphics, tables), receive content from server 1752, transmit information to server 1752, and so on.

In some embodiments, server 1752 can include a processor 1812, a display 1814, one or more inputs 1816, one or more communications systems 1818, and/or memory 1820. In some embodiments, processor 1812 can be any suitable hardware processor or combination of processors, such as a CPU, a GPU, and so on. In some embodiments, display 1814 can include any suitable display devices, such as a computer monitor, a touchscreen, a television, and so on. In some embodiments, inputs 1816 can include any suitable input devices and/or sensors that can be used to receive user input, such as a keyboard, a mouse, a touchscreen, a microphone, and so on.

In some embodiments, communications systems 1818 can include any suitable hardware, firmware, and/or software for communicating information over communication network 1754 and/or any other suitable communication networks. For example, communications systems 1818 can include one or more transceivers, one or more communication chips and/or chip sets, and so on. In a more particular example, communications systems 1818 can include hardware, firmware and/or software that can be used to establish a Wi-Fi connection, a Bluetooth connection, a cellular connection, an Ethernet connection, and so on.

In some embodiments, memory 1820 can include any suitable storage device or devices that can be used to store instructions, values, data, or the like, that can be used, for example, by processor 1812 to present content using display 1814, to communicate with one or more computing devices 1750, and so on. Memory 1820 can include any suitable volatile memory, non-volatile memory, storage, or any suitable combination thereof. For example, memory 1820 can include RAM, ROM, EEPROM, one or more flash drives, one or more hard disks, one or more solid state drives, one or more optical drives, and so on. In some embodiments, memory 1820 can have encoded thereon a server program for controlling operation of server 1752. In such embodiments, processor 1812 can execute at least a portion of the server program to transmit information and/or content (e.g., data, images, a user interface) to one or more computing devices 1750, receive information and/or content from one or more computing devices 1750, receive instructions from one or more devices (e.g., a personal computer, a laptop computer, a tablet computer, a smartphone), and so on.

In some embodiments, data source 1702 can include a processor 1822, one or more image acquisition systems 1824, one or more communications systems 1826, and/or memory 1828. In some embodiments, processor 1822 can be any suitable hardware processor or combination of processors, such as a CPU, a GPU, and so on. In some embodiments, the one or more image acquisition systems 1824 are generally configured to acquire data, images, or both, and can include a CT system, an MRI system, or both. Additionally or alternatively, in some embodiments, one or more image acquisition systems 1824 can include any suitable hardware, firmware, and/or software for coupling to and/or controlling operations of a CT system, and MRI system, or both. In some embodiments, one or more portions of the one or more image acquisition systems 1824 can be removable and/or replaceable.

Note that, although not shown, data source 1702 can include any suitable inputs and/or outputs. For example, data source 1702 can include input devices and/or sensors that can be used to receive user input, such as a keyboard, a mouse, a touchscreen, a microphone, a trackpad, a trackball, and so on. As another example, data source 1702 can include any suitable display devices, such as a computer monitor, a touchscreen, a television, etc., one or more speakers, and so on.

In some embodiments, communications systems 1826 can include any suitable hardware, firmware, and/or software for communicating information to computing device 1750 (and, in some embodiments, over communication network 1754 and/or any other suitable communication networks). For example, communications systems 1826 can include one or more transceivers, one or more communication chips and/or chip sets, and so on. In a more particular example, communications systems 1826 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 1828 can include any suitable storage device or devices that can be used to store instructions, values, data, or the like, that can be used, for example, by processor 1822 to control the one or more image acquisition systems 1824, and/or receive data from the one or more image acquisition systems 1824; to images from data; present content (e.g., images, a user interface) using a display; communicate with one or more computing devices 1750; and so on. Memory 1828 can include any suitable volatile memory, non-volatile memory, storage, or any suitable combination thereof. For example, memory 1828 can include RAM, ROM, EEPROM, one or more flash drives, one or more hard disks, one or more solid state drives, one or more optical drives, and so on. In some embodiments, memory 1828 can have encoded thereon, or otherwise stored therein, a program for controlling operation of image source 1702. In such embodiments, processor 1822 can execute at least a portion of the program to generate images, transmit information and/or content (e.g., data, images) to one or more computing devices 1750, receive information and/or content from one or more computing devices 1750, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

As noted above, in magnetic resonance images it is generally difficult to automatically separate air from other low-signal regions (especially bone, liver, etc.) due to noise and artifacts, which can result in errors in synthetic CT ("sCT") generation for MRI-based RT-planning. This is problematic for the abdomen where air regions are random and therefore cannot be deformed from a reference CT. The systems and methods described in the present disclosure provide a technique that can accurately and automatically determine air-regions in MRI, which in turn enables more robust generation of synthetic CT images from magnetic resonance images.

MR-Linac technology is expected to improve RT by enhancing tumor targeting. The high contrast images capable of being acquired with MRI before and during each treatment delivery allow for online and real-time plan adaptation. However, the dose calculation on the patient anatomy uses a map of relative electron densities ("rED"), which are not directly available from daily MRI. As such, synthetic CT (sCT) images are generated based on the daily MRI.

The two main types of approaches for sCT generation are voxel-based, where only the MRI voxel data is utilized, and atlas-based, where the voxel's location information as well as the intensity information is utilized to generate the rED value.

Voxel-based approaches, where the rED data is directly obtained for each voxel based on the voxel's MR intensity, are useful for situations where no reference CT is available. However, since there is no direct relationship between MR and CT signals, the voxel-based approach requires multiple MR sequences to acquire images, which increases the online preparation time and is, therefore, not desirable for OLAR purposes.

The atlas-based approaches involve transferring the rED data directly from an existing CT of the same patient by either rigid or deformable registration. These approaches can be applied with any single MR sequence (i.e., multiple sequences are not required). Atlas-based methods are therefore more suitable for OLAR, where the reference CT can be acquired offline. Another advantage is that the atlas-based approaches use a patient's own CT and, thus, can be more accurate compared to the voxel-based approaches where generic population based rED, rather the patient specific rED, data are applied.

The Lorenz force from the magnetic field in MR-Linac requires accurate estimates of rED, especially in the lung where population based rED data can result in dose calculation errors. Atlas-based approaches for extra-cranial sites generally need deformable image registration ("DIR") to transfer the rED data, and there is a concern that DIR may be inaccurate for large deformations.

The systems and methods described in the present disclosure overcome these drawbacks and provide a fast atlas-based method to generate rED data, even for extra-cranial sites. The methods can be fully automated and, therefore, can be used for OLAR on an MR-Linac system.

In general, the methods described in the present disclosure transfer rED densities from a reference CT ("rCT") to the daily magnetic resonance image ("dMR") via DIR. The rCT is typically acquired at an earlier date, and is used for deforming the rED data. The dMRI is acquired on the day of treatment, and is used as the target image to which the rCT is deformed.

Figure 19:
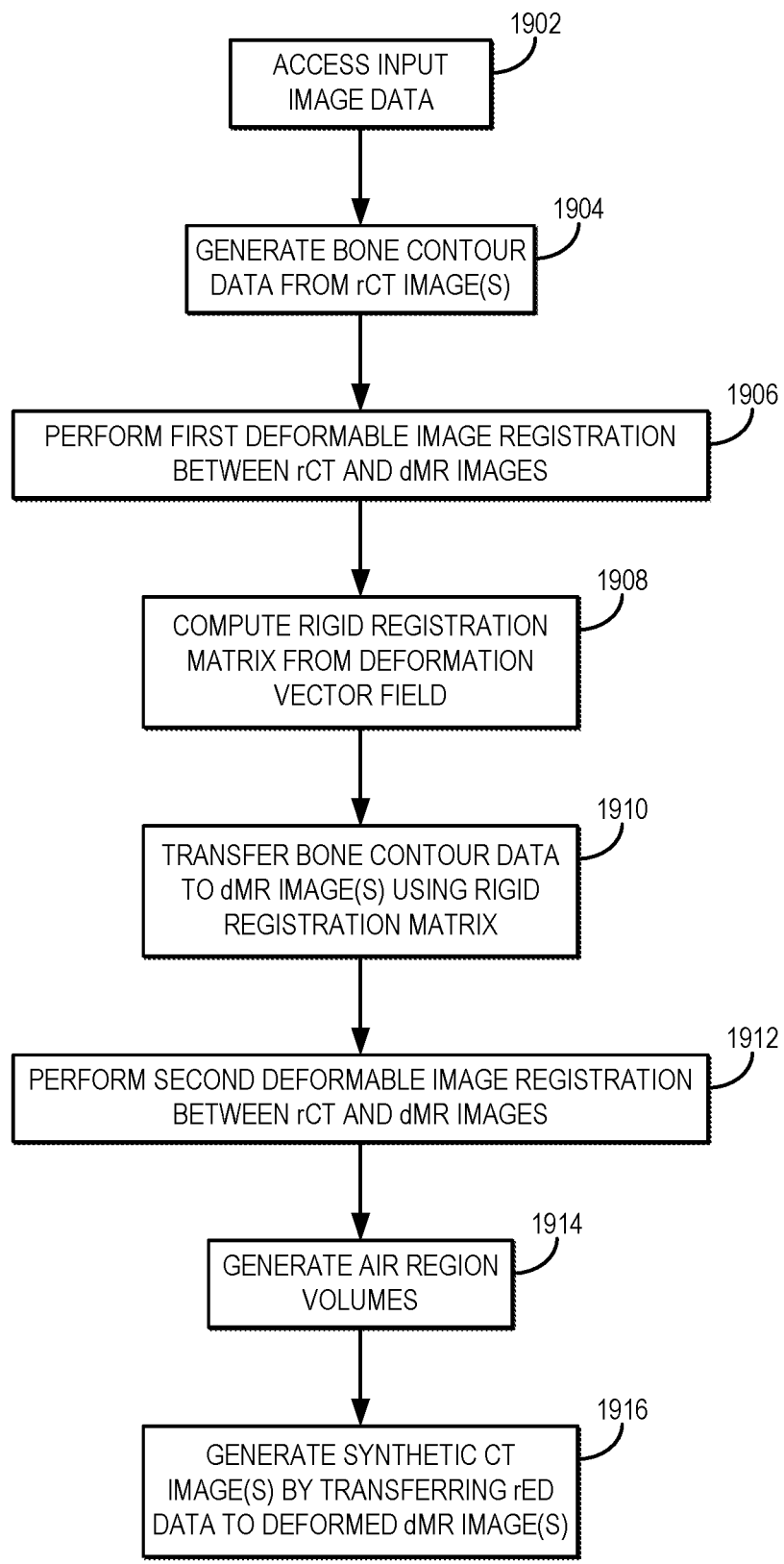
FIG. 19 is a flowchart setting forth the steps of an example method for generating synthetic computed tomography ("CT") images from magnetic resonance images.

Referring now to FIG. 19, a flowchart is illustrated as setting forth the steps of an example method for generating synthetic CT images from magnetic resonance images. The method includes accessing input image data with a computer system, as indicated at step 1902. In general, the input image data includes reference CT images and daily MR images of the patient. Accessing the input image data can include retrieving previously acquired input image data from a memory or other data storage device or medium. In some instances, accessing the input image data may include acquiring images (e.g., rCT images, dMR image) with the appropriate medical imaging system and communicating or otherwise transferring those images to the computer system, which may form a part of the respective medical imaging system(s).

The CT intensities (i.e., Houndsfield Units ("HU")), are transferred and converted to rED map in the following steps. Individual bones are separately delineated on the rCT image, as indicated at step 1904. In some embodiments, this step can be performed offline. In these instances, the bone contour data can be stored in a memory or other data storage and accessed with the computer system at step 1904.

The individual bone contours are then transferred from rCT to dMR. A first DIR is performed on the rCT and dMR images, as indicated at step 1906. As a result of this step, a deformation vector field ("DVF") is computed. For each individual bony volume (e.g., volumes encompassed by the bone contours), a rigid registration matrix, M (i.e., translation and rotation), is calculated from the DVF of the voxels inside each identified bony structure, as indicated at step 1908. This matrix, M, is the best fit to the DVF from all the points inside the bone volume, so that the cumulative error between the DVF and the rigid transfer, $$\int_{ROI} |(M \cdot r) - (DVF(r) + r)|; \tag{27}$$

is minimized over all the voxels. This matrix, M, can be independently calculated for each bony volume. The rigid registration matrices are then used to transform each of the bony contours rigidly from the rCT to the dMR image, as indicated at step 1910.

A second DIR is performed between the rCT and dMR images, this time using a DIR algorithm that constraints the DVF by the bony structures, as indicated at step 1912. All voxels inside one structure in the reference image are only allowed to deform to the voxels of the same structure in the target image; therefore, the structure is forced to deform to the shape delineated on the target image. This preserves the shapes of the bony structures; therefore, each individual bone retains its rigidity, minimizing errors from DIR of bones.

Random air regions in the dMR images (e.g., gas in the bowel) can have their volumes identified on dMR images by auto-thresholding, as indicated at step 1914. Formulas relating the MRI intensities of air (outside the phantoms/patients) and surrounding materials can be established and used to auto-threshold air-regions on MRI. These formulas can be further refined based on the patient MRI-data. As an example, the air containing regions in the abdomen (e.g., colon, bowels, stomach) transferred from a reference MRI to a daily MRI and expanded by 1 cm give a region that can be used for thresholding. Expansion accounts for possible inaccuracies in DIR. The air region determined inside this target region can be further refined using a texture based method. Quantitative image texture features from a gray level co-occurrence matrix ("GLCM"), including autocorrelation, contrast, sum-variance, or combinations thereof, can be extracted from the auto-thresholded regions and a machine learning algorithm (e.g., a naïve Bayesian classifier) implemented with a hardware processor and a memory can be trained with a leave one out cross validation technique to differentiate air from non-air voxels. The performance of the classifier can be judged using the area under the ROC curve ("AUC").

As one non-limiting example for generating the air region volumes, magnetic resonance images can be analyzed as follows. First, the images can be analyzed to grossly identify the regions encompassing the most probable air/gas organs, such as the stomach, duodenum, small bowel, large bowel, colon, and so on. Then, a thresholding equation can be developed based on reference data, such as phantom data. As an example, a threshold value can be computed or otherwise determined from phantom data, such as MR and CT images of one or more phantoms with imbedded air cavities. These air cavities in the phantoms were identified in both the CT images and MRI images. The air cavity contours defined from the CT images can be transferred to the MRI images by a rigid image registration to compare with the air cavity contours delineated on the MRI images. Dice coefficient ("DC") and Housdorff distance were used to measure the differences between the CT-based and MRI-based contours and used to derive the threshold value to identify air/tissue boundaries on patient MRI images.

As one example, the following formula was generated based on phantom studies and can be used to indicate air regions:

$$MR_{threshold1} = (STD_U) + (MAX_{OA}) \tag{28};$$

The low signal regions outside the expanded union structure can be discarded because they have very low likelihood of being air. In Eqn. (28), $STD_U$ is defined as the standard deviation of the intensity value of the union structure and $MAX_{OA}$ is the maximum intensity value of pure air drawn a selected distance (e.g., 2 cm) outside of a boundary, such as outside the patient's anterior boundary. Then, a second threshold formula can be used to fine tune the air regions. As an example, the following formula can be used, $$MR_{threshold2} = a \cdot (MAX) + b \cdot (Median) + c \cdot (STD) \tag{29};$$

The MR$_{threshold2}$ can be obtained from the best match of randomly picked magnetic resonance signals to contour air regions. Statistics can be obtained from reference data (e.g., data acquired from different patients) and used to solve for the coefficients a, b, and c. In some implementations, the coefficients can be solved for offline and stored for later use. The coefficients can be used to calculate the final threshold using Eqn. (29).

Figure 20:
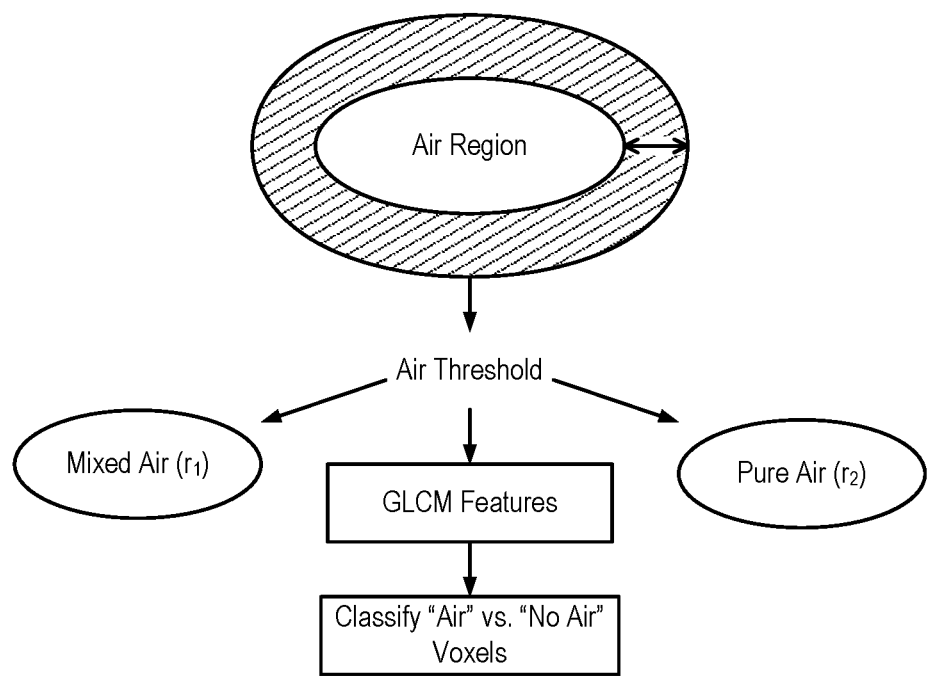
FIG. 20 depicts a schematic of a method for classifying air versus non-air voxels to generate air region volumes that can be used in synthetic CT generation.

To further refine the air boundary on MRI, image texture features in air and non-air regions can be extracted on a voxel-by-voxel basis. A number of different texture features of the GLCM can be extracted to identify the features values for air versus non-air regions. In one example, 23 such features were extracted and used for this purpose. The pure air and the non-air voxels can be identified by the thresholding methods described above. The way of extracting air/non-air voxels from the auto-thresholded air-regions is described in FIG. 20. Pure air-regions ($r_2$) can be identified within the picked up regions ($r_1$) to perform texture analysis.

In one example study, a Student T-test was used to identify features that differ significantly for air versus non-air regions. The combination of the most significant features was tested with a naïve Bayesian classifier and a leave one out cross validation technique to determine the features with highest impact upon distinguishing the air from the non-air regions. Data were divided into training set consisting of (5,000 air and 5,000 non-air voxels), and a testing set (from different patients data sets containing 1,000 voxels each for air/non-air). Classification was performed using the minimum distance to the centroid of the training class. The classifier performance was judged using the area under the ROC curve to identify features with highest impact on classification. All air regions determined by the thresholding methods and refined by the texture feature analysis on MRI were assigned air density for synthetic CT generation.

Referring still to FIG. 19, a synthetic CT image is then generated by transferring rED values from the rCT image to the deformed dMR image using the bone contours and air region volumes, as indicated at step 1916. In some implementations, the rED values are computed from HU data in the rCT image and then transferred to the deformed dMR image, and in other implementations the HU data are transferred from the rCT image to the deformed dMR image before being converted to rED data.

The air region volumes can be transferred to a sCT image, and the sCT values will be overridden by the air density (rED=0.01) in these volumes. The gas regions are randomly occurring; therefore, the dMR has the most accurate representation for them. The locations where these regions are roughly expected (e.g., bowel regions) are already known on sCT, and only the air regions from dMR in these expected locations will be overridden. In this way, the low signal regions (e.g., bone from dMR) will not be mistakenly identified as air regions. The rED for air regions on the sCT that are outside the air regions transferred from dMR will be overridden by tissue density (rED=0.92).

Figure 21:
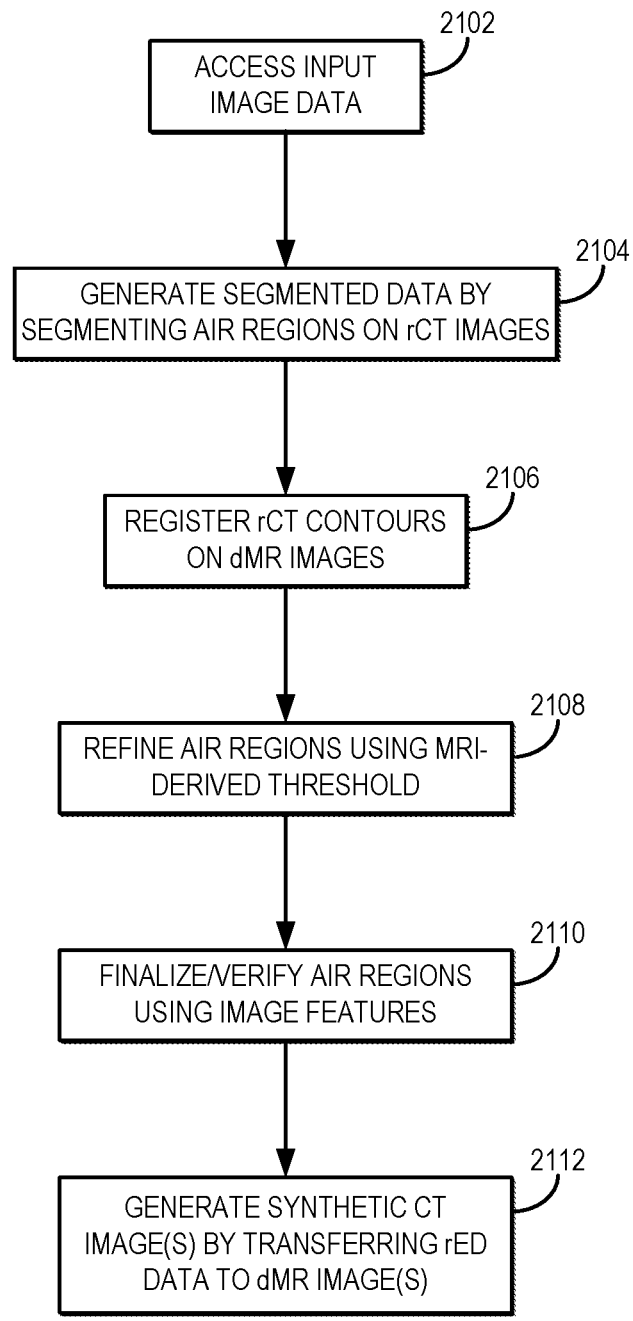
FIG. 21 is a flowchart setting forth the steps of another example method for generating sCT images from magnetic resonance images.

In some implementations, sCT images can be generated without separating and registering bone contours in the input image data. Referring now to FIG. 21, a flowchart is illustrated as setting forth the steps of another example method for generating sCT images from magnetic resonance images. The method includes accessing input image data with a computer system, as indicated at step 2102. In general, the input image data includes reference CT images and daily MR images of the patient. Accessing the input image data can include retrieving previously acquired input image data from a memory or other data storage device or medium. In some instances, accessing the input image data may include acquiring images (e.g., rCT images, dMR image) with the appropriate medical imaging system and communicating or otherwise transferring those images to the computer system, which may form a part of the respective medical imaging system(s).

Segmented data are generated from the input image data by segmenting air regions (e.g., air cavities, gross air regions) and all organs in the input image data, as indicated at process block 2104. These segmented data can be generated, for instance, by manually drawing air containing regions on the rCT images. The manually drawn contours can be drawn with an expansion, such as a 1 cm expansion. In some instances, generating the segmented data can include retrieving previously generated segmented data that are stored in a memory or other data storage device or medium.

The CT contours are then registered on the dMR images in the input image data, as indicated at step 2106. The segmented air regions can then be refined using an MRI-derived threshold, as indicated at step 2108. Methods for determining and refining this MRI-derived threshold are described above with respect to FIG. 19. The refined air regions are then finalize and/or verified based on image feature (e.g., texture feature) analysis, as indicated at step 2110. Methods for finalizing and verifying air regions based on image feature (e.g., texture feature) analysis are also described above with respect to FIG. 19.

Synthetic CT images are then generated by transferring rED values from the rCT images to the dMR images using the air region volumes, as indicated at step 2112. In some implementations, the rED values are computed from HU data in the rCT image and then transferred to the dMR image, and in other implementations the HU data are transferred from the rCT image to the dMR image before being converted to rED data.

Methods for quickly creating sCT images by transferring rED from a patient's own CT based on deformable registration of CT and MRI with special consideration of bone and air regions has been described. The sCT generated is more accurate than that from the common-used bulk density assignment, but without the need for multiple MR sequences.

Using the methods described in the present disclosure, air-tissue boundaries can be identified on magnetic resonance images within 1 mm accuracy, as compared to those on CT images using an auto-thresholding method. The air cavity delineation is improved using the MRI texture differences between air and tissues. As one example, autocorrelation, sum variance, and contrast can be used to evaluate texture differences between air and tissues. The systems and methods described in the present disclosure generally include using intensity-based auto-thresholding and image texture based voxel classification to automatically and accurately segment air regions in magnetic resonance images, which enables synthetic CT images to be generated quickly and precisely for MRI-based RT-planning, especially for OLAR.

Figure 22:
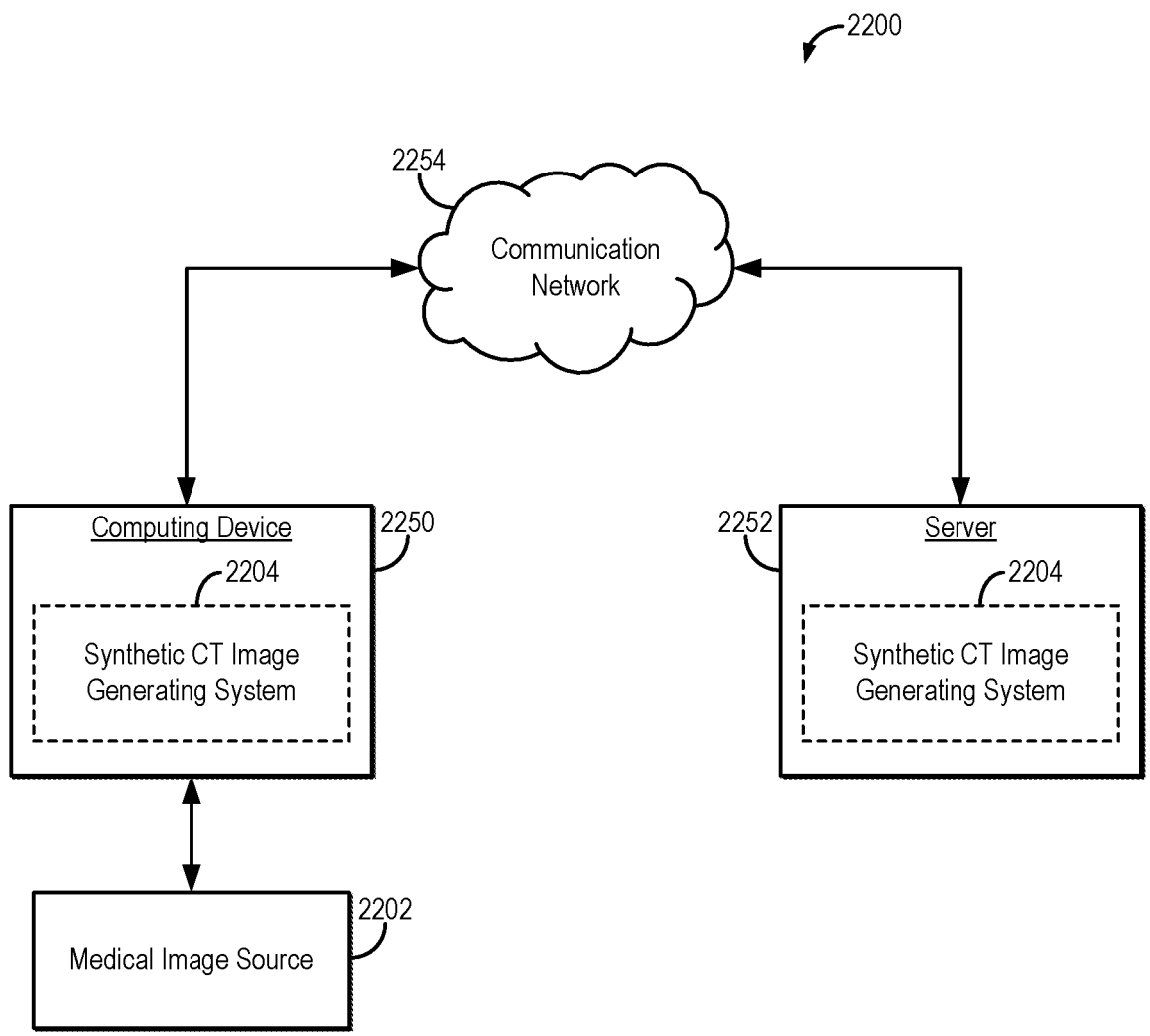
FIG. 22 is a block diagram of an example synthetic CT image generating system that can implement embodiments described in the present disclosure.

Referring now to FIG. 22, an example of a system 2200 for generating synthetic CT images in accordance with some embodiments of the systems and methods described in the present disclosure is shown. As shown in FIG. 22, a computing device 2250 can receive one or more types of data (e.g., rCT image data, dMR image data) from medical image source 2202, which may be an rCT image and dMR image source. In some embodiments, computing device 2250 can execute at least a portion of a synthetic CT image generating system 2204 to generating synthetic CT images from rCT image and dMR image data received from the medical image source 2202.

Additionally or alternatively, in some embodiments, the computing device 2250 can communicate information about data received from the medical image source 2202 to a server 2252 over a communication network 2254, which can execute at least a portion of the synthetic CT image generating system 2204. In such embodiments, the server 2252 can return information to the computing device 2250 (and/or any other suitable computing device) indicative of an output of the synthetic CT image generating system 2204.

In some embodiments, computing device 2250 and/or server 2252 can be any suitable computing device or combination of devices, such as a desktop computer, a laptop computer, a smartphone, a tablet computer, a wearable computer, a server computer, a virtual machine being executed by a physical computing device, and so on. The computing device 2250 and/or server 2252 can also reconstruct images from the data.

In some embodiments, medical image source 2202 can be any suitable source of medical image data (e.g., rCT image data, dMR image data), such as a CT system, an MRI system, another computing device (e.g., a server storing image data), and so on. In some embodiments, medical image source 2202 can be local to computing device 2250. For example, medical image source 2202 can be incorporated with computing device 2250 (e.g., computing device 2250 can be configured as part of a device for capturing, scanning, and/or storing images). As another example, medical image source 2202 can be connected to computing device 2250 by a cable, a direct wireless link, and so on. Additionally or alternatively, in some embodiments, medical image source 2202 can be located locally and/or remotely from computing device 2250, and can communicate data to computing device 2250 (and/or server 2252) via a communication network (e.g., communication network 2254).

In some embodiments, communication network 2254 can be any suitable communication network or combination of communication networks. For example, communication network 2254 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 22 can each be any suitable communications link or combination of communications links, such as wired links, fiber optic links, Wi-Fi links, Bluetooth links, cellular links, and so on.

Figure 23:
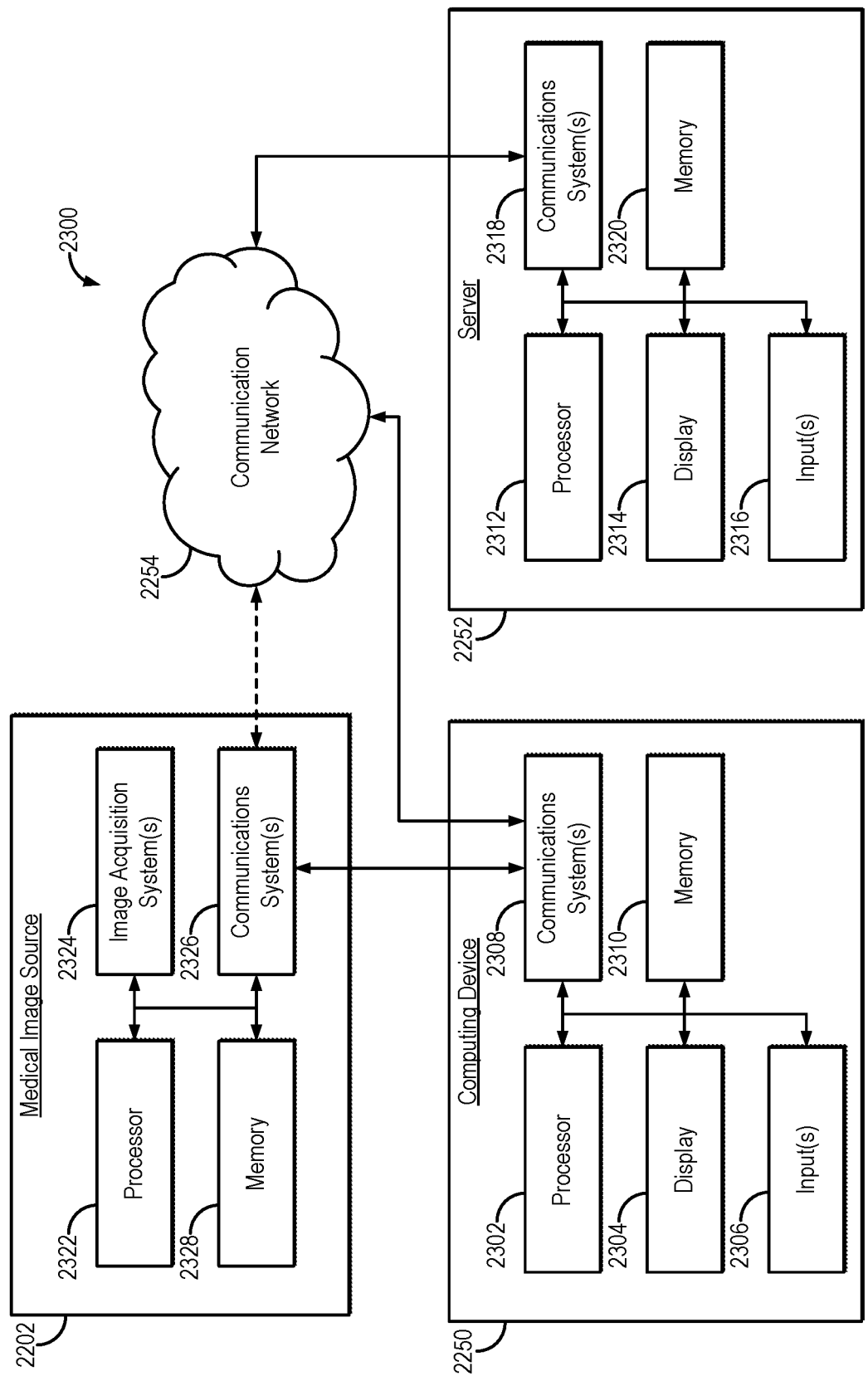
FIG. 23 is a block diagram of example components that can implement the synthetic CT image generating system of FIG. 22.

Referring now to FIG. 23, an example of hardware 2300 that can be used to implement medical image source 2202, computing device 2250, and server 2254 in accordance with some embodiments of the systems and methods described in the present disclosure is shown. As shown in FIG. 23, in some embodiments, computing device 2250 can include a processor 2302, a display 2304, one or more inputs 2306, one or more communication systems 2308, and/or memory 2310. In some embodiments, processor 2302 can be any suitable hardware processor or combination of processors, such as a central processing unit ("CPU"), a graphics processing unit ("GPU"), and so on. In some embodiments, display 2304 can include any suitable display devices, such as a computer monitor, a touchscreen, a television, and so on. In some embodiments, inputs 2306 can include any suitable input devices and/or sensors that can be used to receive user input, such as a keyboard, a mouse, a touchscreen, a microphone, and so on.

In some embodiments, communications systems 2308 can include any suitable hardware, firmware, and/or software for communicating information over communication network 2254 and/or any other suitable communication networks. For example, communications systems 2308 can include one or more transceivers, one or more communication chips and/or chip sets, and so on. In a more particular example, communications systems 2308 can include hardware, firmware and/or software that can be used to establish a Wi-Fi connection, a Bluetooth connection, a cellular connection, an Ethernet connection, and so on.

In some embodiments, memory 2310 can include any suitable storage device or devices that can be used to store instructions, values, data, or the like, that can be used, for example, by processor 2302 to present content using display 2304, to communicate with server 2252 via communications system(s) 2308, and so on. Memory 2310 can include any suitable volatile memory, non-volatile memory, storage, or any suitable combination thereof. For example, memory 2310 can include RAM, ROM, EEPROM, one or more flash drives, one or more hard disks, one or more solid state drives, one or more optical drives, and so on. In some embodiments, memory 2310 can have encoded thereon, or otherwise stored therein, a computer program for controlling operation of computing device 2250. In such embodiments, processor 2302 can execute at least a portion of the computer program to present content (e.g., images, user interfaces, graphics, tables), receive content from server 2252, transmit information to server 2252, and so on.

In some embodiments, server 2252 can include a processor 2312, a display 2314, one or more inputs 2316, one or more communications systems 2318, and/or memory 2320. In some embodiments, processor 2312 can be any suitable hardware processor or combination of processors, such as a CPU, a GPU, and so on. In some embodiments, display 2314 can include any suitable display devices, such as a computer monitor, a touchscreen, a television, and so on. In some embodiments, inputs 2316 can include any suitable input devices and/or sensors that can be used to receive user input, such as a keyboard, a mouse, a touchscreen, a microphone, and so on.

In some embodiments, communications systems 2318 can include any suitable hardware, firmware, and/or software for communicating information over communication network 2254 and/or any other suitable communication networks. For example, communications systems 2318 can include one or more transceivers, one or more communication chips and/or chip sets, and so on. In a more particular example, communications systems 2318 can include hardware, firmware and/or software that can be used to establish a Wi-Fi connection, a Bluetooth connection, a cellular connection, an Ethernet connection, and so on.

In some embodiments, memory 2320 can include any suitable storage device or devices that can be used to store instructions, values, data, or the like, that can be used, for example, by processor 2312 to present content using display 2314, to communicate with one or more computing devices 2250, and so on. Memory 2320 can include any suitable volatile memory, non-volatile memory, storage, or any suitable combination thereof. For example, memory 2320 can include RAM, ROM, EEPROM, one or more flash drives, one or more hard disks, one or more solid state drives, one or more optical drives, and so on. In some embodiments, memory 2320 can have encoded thereon a server program for controlling operation of server 2252. In such embodiments, processor 2312 can execute at least a portion of the server program to transmit information and/or content (e.g., data, images, a user interface) to one or more computing devices 2250, receive information and/or content from one or more computing devices 2250, receive instructions from one or more devices (e.g., a personal computer, a laptop computer, a tablet computer, a smartphone), and so on.

In some embodiments, medical image source 2202 can include a processor 2322, one or more image acquisition systems 2324, one or more communications systems 2326, and/or memory 2328. In some embodiments, processor 2322 can be any suitable hardware processor or combination of processors, such as a CPU, a GPU, and so on. In some embodiments, the one or more image acquisition systems 2324 are generally configured to acquire data, images, or both, and can include a CT system, and MRI system, or both. Additionally or alternatively, in some embodiments, one or more image acquisition systems 2324 can include any suitable hardware, firmware, and/or software for coupling to and/or controlling operations of a CT system, and MRI system, or both. In some embodiments, one or more portions of the one or more image acquisition systems 2324 can be removable and/or replaceable.

Note that, although not shown, medical image source 2202 can include any suitable inputs and/or outputs. For example, medical image source 2202 can include input devices and/or sensors that can be used to receive user input, such as a keyboard, a mouse, a touchscreen, a microphone, a trackpad, a trackball, and so on. As another example, medical image source 2202 can include any suitable display devices, such as a computer monitor, a touchscreen, a television, etc., one or more speakers, and so on.

In some embodiments, communications systems 2326 can include any suitable hardware, firmware, and/or software for communicating information to computing device 2250 (and, in some embodiments, over communication network 2254 and/or any other suitable communication networks). For example, communications systems 2326 can include one or more transceivers, one or more communication chips and/or chip sets, and so on. In a more particular example, communications systems 2326 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 2328 can include any suitable storage device or devices that can be used to store instructions, values, data, or the like, that can be used, for example, by processor 2322 to control the one or more image acquisition systems 2324, and/or receive data from the one or more image acquisition systems 2324; to images from data; present content (e.g., images, a user interface) using a display; communicate with one or more computing devices 2250; and so on. Memory 2328 can include any suitable volatile memory, non-volatile memory, storage, or any suitable combination thereof. For example, memory 2328 can include RAM, ROM, EEPROM, one or more flash drives, one or more hard disks, one or more solid state drives, one or more optical drives, and so on. In some embodiments, memory 2328 can have encoded thereon, or otherwise stored therein, a program for controlling operation of image source 2202. In such embodiments, processor 2322 can execute at least a portion of the program to generate images, transmit information and/or content (e.g., data, images) to one or more computing devices 2250, receive information and/or content from one or more computing devices 2250, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 24:
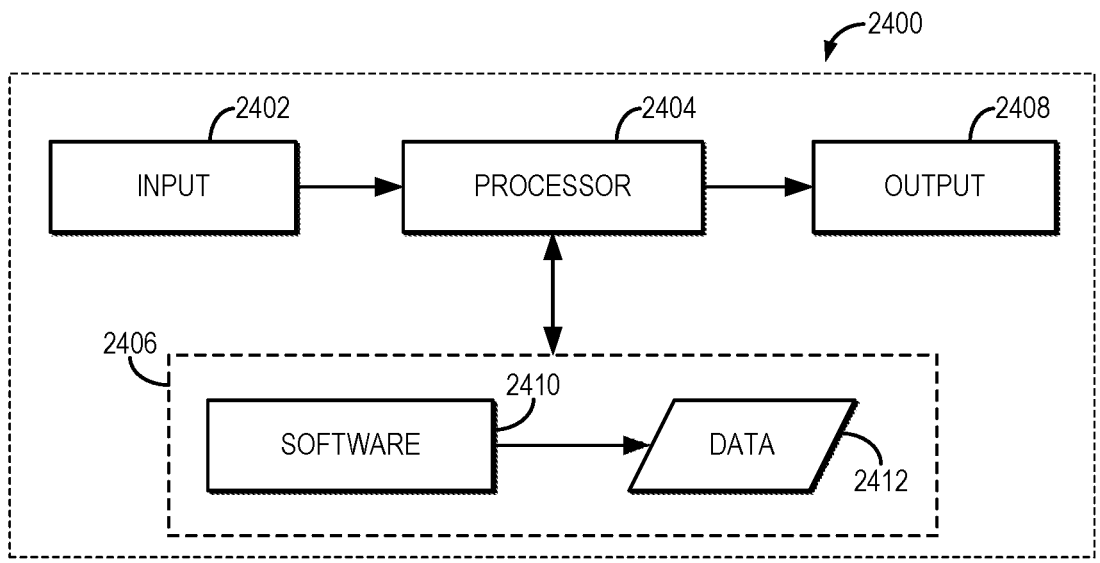
FIG. 24 is a block diagram of an example computer system that can implement the methods described in the present disclosure.

Referring now to FIG. 24, a block diagram of an example of a computer system 2400 that can perform the methods described in the present disclosure is shown. The computer system 2400 generally includes an input 2402, at least one hardware processor 2404, a memory 2406, and an output 2408. Thus, the computer system 2400 is generally implemented with a hardware processor 2404 and a memory 2406.

In some embodiments, the computer system 2400 can be a radiation treatment planning system ("TPS"). The computer system 2400 may also be implemented, in some examples, by a workstation, a notebook computer, a tablet device, a mobile device, a multimedia device, a network server, a mainframe, one or more controllers, one or more microcontrollers, or any other general-purpose or application-specific computing device.

The computer system 2400 may operate autonomously or semi-autonomously, or may read executable software instructions from the memory 2406 or a computer-readable medium (e.g., a hard drive, a CD-ROM, flash memory), or may receive instructions via the input 2402 from a user, or any another source logically connected to a computer or device, such as another networked computer or server. Thus, in some embodiments, the computer system 2400 can also include any suitable device for reading computer-readable storage media.

In general, the computer system 2400 is programmed or otherwise configured to implement the methods and algorithms described in the present disclosure. For instance, the computer system 2400 can be programmed to generate an indication of whether to initiate OLAR based on an analysis of Jacobian determinant histogram metrics, automatically correct contours in a radiation treatment plan, validate contours for OLAR, evaluate radiation treatment plan quality automatically based on texture features and spatial dose metrics, generate synthetic CT images from magnetic resonance images, or combinations thereof.

The input 2402 may take any suitable shape or form, as desired, for operation of the computer system 2400, including the ability for selecting, entering, or otherwise specifying parameters consistent with performing tasks, processing data, or operating the computer system 2400. In some aspects, the input 2402 may be configured to receive data, such as data acquired with a medical imaging system, previously generated radiation treatment plans, and so on. Such data may be processed as described above to generate an indication of whether to initiate OLAR based on an analysis of Jacobian determinant histogram metrics, automatically correct contours in a radiation treatment plan, validate contours for OLAR, evaluate radiation treatment plan quality automatically based on texture features and spatial dose metrics, generate synthetic CT images from magnetic resonance images, or combinations thereof. In addition, the input 2402 may also be configured to receive any other data or information considered useful for implementing the methods described above.

Among the processing tasks for operating the computer system 2400, the one or more hardware processors 2404 may also be configured to carry out any number of post-processing steps on data received by way of the input 2402.

The memory 2406 may contain software 2410 and data 2412, such as data acquired with a medical image system or previously generated radiation treatment plans, and may be configured for storage and retrieval of processed information, instructions, and data to be processed by the one or more hardware processors 2404. In some aspects, the software 2410 may contain instructions directed to implementing the methods described above.

In addition, the output 2408 may take any shape or form, as desired, and may be configured for displaying medical images, radiation treatment plans, and other data computed, derived, or otherwise obtained from such images or plans, in addition to other desired information.

Figure 25:
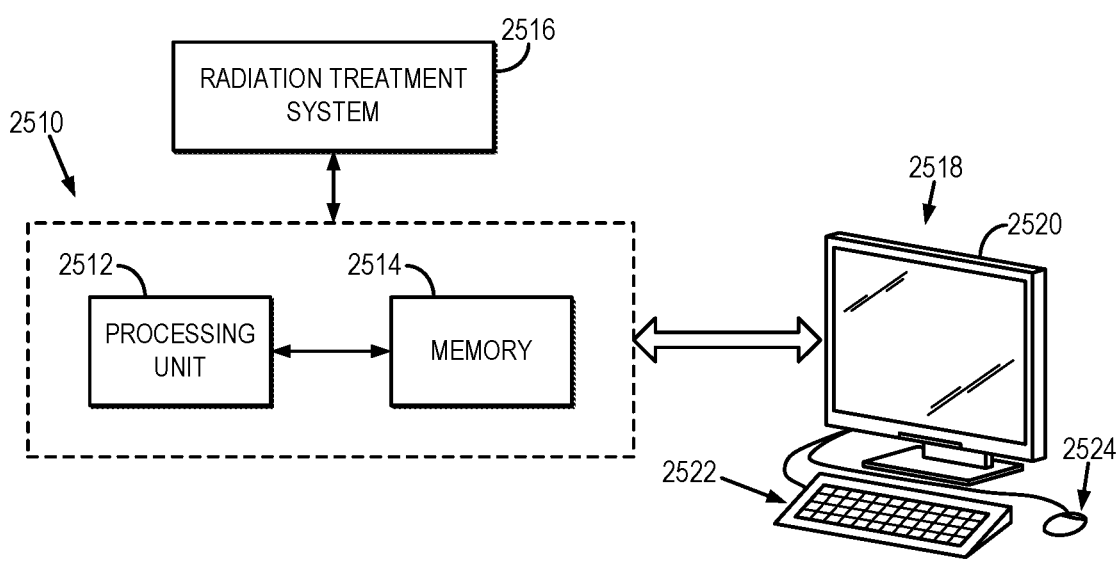
FIG. 25 is a block diagram of an example radiation treatment planning system that can implement the methods described in the present disclosure.

As noted, the systems and methods described in the present disclosure can be implemented using a radiation treatment planning system. Referring now to FIG. 25, an example of such a radiation treatment planning system 2510 is illustrated. The radiation treatment planning system 2510 is preferably in communication with one or more radiation treatment systems 2512, which may include any suitable radiation treatment system.

The radiation treatment planning system 2510 generally includes a memory 2514 that is operably coupled to a processor unit 2516. As an example, the processor unit 2516 can be a commercially available computer processor, such as those described above. The processor unit 2516 is configured to carry out one or more of the steps of the methods described above.

As an example, the memory 2514 can include a plurality of memory elements, or can include a single memory element. In general, the memory 2514 is configured to store information regarding patient data, a treatment target (e.g., a tumor located within a patient), imaging beam model data, treatment beam model data, dose matrices, and so on.

Preferably, the radiation treatment planning system 2510 includes, or is otherwise in communication with, a user interface 2518. As an example, the user interface 2518 provides information to a user, such as a medical physicist. For example, the user interface 2518 can include a display 2520 and one or more input devices, such as a keyboard 2522 and mouse 2524.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for validating an accuracy of radiation treatment plan contour data, the method comprising:
   (a) accessing with a computer system, previously generated contour data comprising contours associated with a radiation treatment plan for a subject;
   (b) accessing with the computer system, an image of the subject;
   (c) generating with the computer system, inner shell data by eroding contours in the contour data by a first margin;
   (d) generating with the computer system, outer shell data by expanding contours in the contour data by a second margin;
   (e) computing with the computer system, image feature data from the image;
   (f) generating with the computer system, an inner shell image feature map from the image feature data over contours in the inner shell data;
   (g) generating with the computer system, an outer shell image feature map from the image feature data over contours in the outer shell data;
   (h) validating the contour data by inputting the inner shell image feature map and the outer shell image feature map to a machine learning algorithm, generating output as labeled contour data, wherein the labeled contour data labels contour data that are validated as accurate contour data contour data that are not validated as inaccurate contour data;
   (i) generating a binary mask for a given contour in the contour data by assigning a first binary value to pixels within the contour and assigning a second binary value to pixels outside the contour, and wherein the inner shell data are generated by eroding the binary mask by the first margin and the outer shell data are generated by dilating the binary mask by the second margin; and
   (j) generating core region data from the binary mask, wherein the core region data are generated by:
      generating a distance map by computing a distance metric between each pixel in the binary mask and a boundary pixel nearest to that pixel in the binary mask; and
      defining the core region based on a percent of pixels having highest distance metric values in the distance map.

2. The method as recited in claim 1, wherein the distance metric is a Euclidean distance metric.

3. The method as recited in claim 1, wherein the percent is 20 percent.

4. The method as recited in claim 1, wherein the percent is 30 percent.

5. The method as recited in claim 1, further comprising generating with the computer system, a core region image feature map from the image feature data over the outer core region.

6. The method as recited in claim 5, wherein the machine learning algorithm implements a decision tree model that takes as inputs the core region image feature data, the inner shell image feature data, and the outer shell image feature data.

7. The method as recited in claim 6, wherein the decision tree model comprises:
   a first level in which the core region image feature data are evaluated relative to ground truth data;
   a second level in which the inner shell image feature data are evaluated relative to ground truth data; and
   a third level in which the outer shell image feature data are evaluated relative to ground truth data.

8. The method as recited in claim 7, wherein the first level of the decision tree model evaluates a selected set of image features in the core region image feature data to similar image features in the ground truth data.

9. The method as recited in claim 8, wherein the set of image features is selected based on a hierarchical clustering of the image feature data contained in the core region.

10. The method as recited in claim 7, wherein a contour is validated when its corresponding image feature data pass the first level, the second level, and the third level of the decision tree model.

11. The method as recited in claim 1, wherein the inner shell image feature map and the outer shell image feature map are each normalized based on image feature data contained in the core region.

12. The method as recited in claim 1, wherein the first margin and the second margin have a same margin value.

13. The method as recited in claim 12, wherein the margin value is 4 mm.

14. The method as recited in claim 1, wherein the image feature data comprise intensity histogram-based image features.

15. The method as recited in claim 14, wherein the intensity histogram-based image features comprise at least one of mean, standard deviation, range, skewness, and kurtosis.

16. The method as recited in claim 1, wherein the image feature data comprise texture features computed based on a gray-level co-occurrence matrix.

17. The method as recited in claim 1, wherein the image feature data comprise texture features computed based on a gray-level run-length matrix.

18. The method as recited in claim 1, wherein the machine learning algorithm implements a recursive random forest classification to select a set of image features against which the inner shell image feature map and the outer shell image feature map are compared to validate the contour data.

19. The method as recited in claim 1, further comprising:
   inputting the inaccurate contour data in the labeled contour data to a contour correction algorithm, generating output as corrected contour data.

20. The method as recited in claim 19, wherein the corrected contour data are further validated by repeating steps (c)-(h) using the corrected contour data as input contour data.

21. The method as recited in claim 19, wherein the contour correction algorithm comprises:
   computing with the computer system, second image feature data for a region-of-interest (ROI) in the image, wherein the ROI is defined by a contour in the inaccurate contour data;
   generating with the computer system, an image feature map from the second image feature data, wherein the image feature map depicts image feature values in the ROI;
   generating corrected contour data by inputting the image feature map and the inaccurate contour data to an active contour algorithm, generating output as the corrected contour data;
   wherein the image feature map is used by the active contour algorithm as an external force that guides an active curve to find a corrected boundary for the inaccurate contour data.

22. A method for validating an accuracy of radiation treatment plan contour data, the method comprising:
   (a) accessing with a computer system, previously generated contour data comprising contours associated with a radiation treatment plan for a subject;
   (b) accessing with the computer system, an image of the subject;
   (c) generating with the computer system, inner shell data by eroding contours in the contour data by a first margin;
   (d) generating with the computer system, outer shell data by expanding contours in the contour data by a second margin, wherein the first margin and the second margin have a same margin value;
   (e) computing with the computer system, image feature data from the image;
   (f) generating with the computer system, an inner shell image feature map from the image feature data over contours in the inner shell data;
   (g) generating with the computer system, an outer shell image feature map from the image feature data over contours in the outer shell data; and
   (h) validating the contour data by inputting the inner shell image feature map and the outer shell image feature map to a machine learning algorithm, generating output as labeled contour data, wherein the labeled contour data labels contour data that are validated as accurate contour data contour data that are not validated as inaccurate contour data.

23. The method as recited in claim 22, wherein the margin value is 4 mm.

24. A method for validating an accuracy of radiation treatment plan contour data, the method comprising:
   (a) accessing with a computer system, previously generated contour data comprising contours associated with a radiation treatment plan for a subject;
   (b) accessing with the computer system, an image of the subject;
   (c) generating with the computer system, inner shell data by eroding contours in the contour data by a first margin;
   (d) generating with the computer system, outer shell data by expanding contours in the contour data by a second margin;
   (e) computing with the computer system, image feature data from the image;
   (f) generating with the computer system, an inner shell image feature map from the image feature data over contours in the inner shell data;

(g) generating with the computer system, an outer shell image feature map from the image feature data over contours in the outer shell data; and (h) validating the contour data by inputting the inner shell image feature map and the outer shell image feature map to a machine learning algorithm, generating output as labeled contour data, wherein the labeled contour data labels contour data that are validated as accurate contour data contour data that are not validated as inaccurate contour data;

wherein the machine learning algorithm implements a recursive random forest classification to select a set of image features against which the inner shell image feature map and the outer shell image feature map are compared to validate the contour data.

25. A method for validating an accuracy of radiation treatment plan contour data, the method comprising:

(a) accessing with a computer system, previously generated contour data comprising contours associated with a radiation treatment plan for a subject;

(b) accessing with the computer system, an image of the subject;

(c) generating with the computer system, inner shell data by eroding contours in the contour data by a first margin;

(d) generating with the computer system, outer shell data by expanding contours in the contour data by a second margin;

(e) computing with the computer system, image feature data from the image;

(f) generating with the computer system, an inner shell image feature map from the image feature data over contours in the inner shell data;

(g) generating with the computer system, an outer shell image feature map from the image feature data over contours in the outer shell data;

(h) validating the contour data by inputting the inner shell image feature map and the outer shell image feature map to a machine learning algorithm, generating output as labeled contour data, wherein the labeled contour data labels contour data that are validated as accurate contour data contour data that are not validated as inaccurate contour data; and (i) inputting the inaccurate contour data in the labeled contour data to a contour correction algorithm, generating output as corrected contour data.

26. The method as recited in claim 25, wherein the corrected contour data are further validated by repeating steps (c)-(h) using the corrected contour data as input contour data.

27. The method as recited in claim 25, wherein the contour correction algorithm comprises:

computing with the computer system, second image feature data for a region-of-interest (ROI) in the image, wherein the ROI is defined by a contour in the inaccurate contour data;

generating with the computer system, an image feature map from the second image feature data, wherein the image feature map depicts image feature values in the ROI;

generating corrected contour data by inputting the image feature map and the inaccurate contour data to an active contour algorithm, generating output as the corrected contour data;

wherein the image feature map is used by the active contour algorithm as an external force that guides an active curve to find a corrected boundary for the inaccurate contour data.

* * * * *